(12) United States Patent
Muratoglu et al.

(10) Patent No.: US 10,213,313 B2
(45) Date of Patent: *Feb. 26, 2019

(54) FEMORAL HEADS, MOBILE INSERTS, ACETABULAR COMPONENTS, AND MODULAR JUNCTIONS FOR ORTHOPEDIC IMPLANTS AND METHODS OF USING FEMORAL HEADS, MOBILE INSETS, ACETABULAR COMPONENTS, AND MODULAR JUNCTIONS FOR ORTHOPEDIC IMPLANTS

(71) Applicant: The General Hospital Corporation, Boston, MA (US)

(72) Inventors: Orhun K. Muratoglu, Cambridge, MA (US); Kartik Mangudi Varadarajan, Belmont, MA (US); Henrik Malchau, Boston, MA (US); Harry E. Rubash, Weston, MA (US); Andrew A. Freiberg, Weston, MA (US); Michael Patrick Duffy, Boston, MA (US); Thomas Zumbrunn, Somerville, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/269,622

(22) Filed: Sep. 19, 2016

(65) Prior Publication Data
US 2017/0135820 A1 May 18, 2017

Related U.S. Application Data

(63) Continuation of application No. 14/039,287, filed on Sep. 27, 2013, now Pat. No. 9,445,905.
(Continued)

(51) Int. Cl.
*A61F 2/36* (2006.01)
*A61F 2/30* (2006.01)
(Continued)

(52) U.S. Cl.
CPC ............ *A61F 2/3609* (2013.01); *A61F 2/30* (2013.01); *A61F 2/30771* (2013.01); *A61F 2/32* (2013.01);
(Continued)

(58) Field of Classification Search
CPC .. A61F 2/36; A61F 2/3609; A61F 2002/3609; A61F 2002/3611;
(Continued)

(56) References Cited

U.S. PATENT DOCUMENTS 3,510,883 A * 5/1970 Cathcart .................. A61F 2/36
623/22.4
4,135,517 A 1/1979 Reale
(Continued)

FOREIGN PATENT DOCUMENTS

EP 0963740 A1 12/1999
EP 2489333 A1 8/2012
(Continued)

OTHER PUBLICATIONS

Bergmann, et al., Hip Contact Forces and Gait Patterns from Routine Activities, Journal of Biomechanics, 2001, 34:859-871.
(Continued)

*Primary Examiner* — Alvin Stewart
(74) *Attorney, Agent, or Firm* — Quarles & Brady LLP

(57) ABSTRACT

Femoral heads, mobile inserts, acetabular components, and modular junctions for orthopedic implants, e.g., hip replacement implants, and methods of using femoral heads, mobile inserts, acetabular components, and modular junctions for orthopedic implants are provided. Prosthetic femoral heads, mobile inserts, and acetabular components are provided that can alleviate soft tissue impingement, reduce implant wear, and/or reduce frictional torque. Modular junctions are provided that can minimize the incidence of loosening and micromotion that can occur at modular junctions of orthopedic implants.

12 Claims, 67 Drawing Sheets

Related U.S. Application Data

(60) Provisional application No. 61/784,272, filed on Mar. 14, 2013, provisional application No. 61/706,426, filed on Sep. 27, 2012, provisional application No. 61/706,439, filed on Sep. 27, 2012, provisional application No. 61/706,449, filed on Sep. 27, 2012.

(51) Int. Cl.
  *A61F 2/32* (2006.01)
  *A61F 2/46* (2006.01)
  *A61F 2/28* (2006.01)

(52) U.S. Cl.
  CPC .............. *A61F 2/36* (2013.01); *A61F 2/3603* (2013.01); *A61F 2/468* (2013.01); *A61F 2002/2828* (2013.01); *A61F 2002/3082* (2013.01); *A61F 2002/30092* (2013.01); *A61F 2002/30299* (2013.01); *A61F 2002/30347* (2013.01); *A61F 2002/30474* (2013.01); *A61F 2002/30688* (2013.01); *A61F 2002/30937* (2013.01); *A61F 2002/3208* (2013.01); *A61F 2002/365* (2013.01); *A61F 2002/3611* (2013.01); *A61F 2002/3615* (2013.01); *A61F 2002/3617* (2013.01); *A61F 2002/3623* (2013.01)

(58) Field of Classification Search
  CPC ...... A61F 2002/3613; A61F 2002/3617; A61F 2002/3619; A61F 2002/3621; A61F 2002/3623; A61F 2/40; A61F 2002/4018
  USPC ...................................................... 623/22.24
  See application file for complete search history.

(56) References Cited

U.S. PATENT DOCUMENTS

| | | | |
|---|---|---|---|
| 4,221,623 A * | 9/1980 | Heissler | A61F 2/36 156/169 |
| 4,279,042 A | 7/1981 | Andriacchi et al. | |
| 4,528,702 A | 7/1985 | Frey | |
| 4,530,114 A | 7/1985 | Tepic | |
| 4,532,660 A * | 8/1985 | Field | A61F 2/3601 606/60 |
| 4,770,659 A | 9/1988 | Kendall | |
| 4,784,662 A | 11/1988 | Muller | |
| 4,792,337 A | 12/1988 | Muller | |
| 4,911,723 A * | 3/1990 | Menschik | A61F 2/32 623/22.15 |
| 4,936,859 A | 6/1990 | Morscher et al. | |
| 4,944,762 A | 7/1990 | Link et al. | |
| 4,997,444 A | 3/1991 | Farling | |
| 5,037,442 A | 8/1991 | Wintermantel et al. | |
| 5,078,746 A | 1/1992 | Garner | |
| 5,219,363 A | 6/1993 | Crowninshield et al. | |
| 5,405,403 A | 4/1995 | Mikhail | |
| 5,735,905 A * | 4/1998 | Parr | A61F 2/3609 623/23.11 |
| 5,879,400 A | 3/1999 | Merrill et al. | |
| 5,879,406 A | 3/1999 | Lilley | |
| 6,042,612 A | 3/2000 | Voydeville | |
| 6,059,830 A * | 5/2000 | Lippincott, III | A61F 2/32 623/18.11 |
| 6,126,695 A * | 10/2000 | Semlitsch | A61F 2/30767 623/18.11 |
| 6,136,036 A | 10/2000 | Scholz | |
| 6,214,053 B1 | 4/2001 | Ling et al. | |
| 6,379,390 B1 | 4/2002 | Advani et al. | |
| 6,413,280 B1 * | 7/2002 | Feiler | A61F 2/32 623/22.15 |
| 6,425,922 B1 | 7/2002 | Pope et al. | |
| 6,508,840 B1 * | 1/2003 | Rockwood, Jr. | A61F 2/40 128/898 |
| 6,547,824 B1 | 4/2003 | Price | |
| 6,607,560 B1 * | 8/2003 | Pfaff | A61F 2/30965 623/22.45 |
| 6,800,095 B1 | 10/2004 | Pope et al. | |
| 7,166,650 B2 | 1/2007 | Muratoglu et al. | |
| 7,169,186 B2 | 1/2007 | Harris et al. | |
| 7,879,106 B2 * | 2/2011 | McMinn | A61F 2/3859 623/22.44 |
| 7,906,064 B2 | 3/2011 | Muratoglu et al. | |
| 7,985,262 B2 | 7/2011 | Frazee et al. | |
| 8,293,811 B2 | 10/2012 | Muratoglu et al. | |
| 8,439,978 B2 | 5/2013 | Ebbitt | |
| 8,579,985 B2 * | 11/2013 | Podolsky | A61F 2/4609 623/22.42 |
| 8,702,804 B2 | 4/2014 | Smith et al. | |
| 8,974,540 B2 * | 3/2015 | Podolsky | A61F 2/4637 623/22.4 |
| 9,211,188 B2 * | 12/2015 | McMinn | A61F 2/3609 |
| 9,445,905 B2 * | 9/2016 | Muratoglu | A61F 2/30 |
| 2002/0193882 A1 * | 12/2002 | Koller | A61F 2/4684 623/23.12 |
| 2003/0114935 A1 | 6/2003 | Chan et al. | |
| 2003/0187512 A1 | 10/2003 | Frederick et al. | |
| 2003/0187514 A1 * | 10/2003 | McMinn | A61F 2/3859 623/22.44 |
| 2004/0054418 A1 | 3/2004 | McLean et al. | |
| 2004/0059429 A1 * | 3/2004 | Amin | A61F 2/3609 623/23.51 |
| 2005/0060040 A1 | 3/2005 | Auxepaules et al. | |
| 2005/0187638 A1 | 8/2005 | Glien et al. | |
| 2005/0256584 A1 | 11/2005 | Farrar | |
| 2005/0261776 A1 | 11/2005 | Taylor | |
| 2006/0106463 A1 | 5/2006 | Bigsby et al. | |
| 2006/0188845 A1 * | 8/2006 | Serafin, Jr. | A61C 8/0048 433/173 |
| 2006/0217815 A1 | 9/2006 | Gibbs et al. | |
| 2006/0259148 A1 | 11/2006 | Bar-Ziv | |
| 2007/0073410 A1 | 3/2007 | Raugel | |
| 2007/0270975 A1 | 11/2007 | Taylor et al. | |
| 2008/0109081 A1 | 5/2008 | Bao et al. | |
| 2008/0114459 A1 | 5/2008 | Scott et al. | |
| 2008/0154369 A1 | 6/2008 | Barr et al. | |
| 2008/0188944 A1 | 8/2008 | Ernsberger | |
| 2008/0215142 A1 | 9/2008 | Muratoglu et al. | |
| 2009/0105364 A1 | 4/2009 | Merrill et al. | |
| 2009/0112330 A1 | 4/2009 | Grundei | |
| 2009/0192620 A1 * | 7/2009 | Ebbitt | A61F 2/3603 623/18.11 |
| 2009/0299484 A1 * | 12/2009 | Dietrich | A61F 2/0095 623/22.4 |
| 2010/0063589 A1 | 3/2010 | Tepic | |
| 2010/0161069 A1 * | 6/2010 | Ragbir | A61F 2/4684 623/22.11 |
| 2010/0211180 A1 | 8/2010 | Helmuth et al. | |
| 2011/0118848 A1 * | 5/2011 | Faccioli | A61F 2/36 623/22.11 |
| 2011/0160867 A1 * | 6/2011 | Meridew | A61F 2/3609 623/20.36 |
| 2011/0301654 A1 | 12/2011 | Wozencroft et al. | |
| 2012/0109334 A1 | 5/2012 | Forsell | |
| 2012/0116530 A1 | 5/2012 | Forsell | |
| 2012/0130504 A1 * | 5/2012 | Forsell | A61F 2/3601 623/23.11 |
| 2012/0165951 A1 | 6/2012 | Forsell | |
| 2012/0232667 A1 * | 9/2012 | Katrana | A61F 2/4014 623/19.12 |
| 2012/0239160 A1 | 9/2012 | Belew et al. | |
| 2013/0060347 A1 * | 3/2013 | McMinn | A61F 2/3603 623/23.23 |
| 2013/0310947 A1 * | 11/2013 | Cremascoli | A61F 2/3609 623/23.35 |
| 2014/0094927 A1 * | 4/2014 | Weeden | A61F 2/32 623/22.21 |
| 2014/0128988 A1 * | 5/2014 | Muratoglu | A61F 2/30 623/23.11 |
| 2014/0200675 A1 * | 7/2014 | Termanini | A61F 2/32 623/23.13 |

(56) References Cited

U.S. PATENT DOCUMENTS

| | | |
|---|---|---|
| 2014/0257512 A1 | 9/2014 | Liu |
| 2014/0371868 A1 | 12/2014 | Anapliotis |
| 2015/0013469 A1* | 1/2015 | Flohr ............... A61F 2/468 73/826 |
| 2015/0039094 A1* | 2/2015 | Kuntz ............... A61F 2/3603 623/23.14 |
| 2015/0094822 A1* | 4/2015 | Vogt ............... A61F 2/32 623/23.39 |
| 2015/0272740 A1* | 10/2015 | Wakiyama ............ A61F 2/3609 623/23.11 |
| 2016/0193050 A1* | 7/2016 | Cappelletti ........... A61F 2/3609 623/18.11 |
| 2016/0262896 A1* | 9/2016 | Bal ............... A61F 2/3859 |

FOREIGN PATENT DOCUMENTS

| | | |
|---|---|---|
| FR | 2551655 A1 | 3/1985 |
| FR | 2951071 A1 | 4/2011 |
| WO | 2009118673 A1 | 10/2009 |

OTHER PUBLICATIONS

Browne, et al., Failure of Larger-Diameter Metal-on-Metal Total Hip Arthroplasty Resulting from Anterior Iliopsoas Impingement, Journal of Arthroplasty, 2011, 26(6):978.e5-978.e8.

Burroughs, et al., Range of Motion and Stability in Total Hip Arthroplasty With 28-, 32-, 38-, and 44-mm Femoral Head Sizes, Journal of Arthroplasty, 2005, 20(1):11-19.

Cobb, et al., Why Large-Head Metal-on-Metal Hip Replacements are Painful, Journal of Bone and Joint Surgery, 2011, 93-B(7):881-885.

Luchiewicz, et al., Femoral Head Size and Wear of Highly Cross-Linked Polyethylene at 5 to 8 Years, Clinical Orthopaedics and Related Research, 2009, 467:3290-3296.

Langton, et al., Taper Junction Failure in Large-Diameter Metal-on-Metal Bearings, Bone & Joint Research, 2012, 1(4):56-63.

Lieberman, et al., An Analysis of the Head-Neck Taper Interface in Retrieved Hip Prostheses, Clinical Orthopaedics and Related Research, 1994, 300:162-167.

Livermore, et al., Effect of Femoral Head Size on Wear of the Polyethylene Acetabular Component, Journal of Bone and Joint Surgery, 1990, 72-A(4):518-528.

Meyer, et al., Corrosion at the Cone/Taper Interface Leads to Failure of Large-Diameter Metal-on-Metal Total Hip Arthroplasties, Clinical Orthopaedics and Related Research, 2012, 470:3101-3108.

Philippot, et al., The Use of a Dual-Articulation Acetabular Cup System to Prevent Dislocation After Primary Total Hip Arthroplasty: Analysis of 384 Cases at a Mean Follow-Up of 15 Years, International Orthopaedics (SICOT), 2009, 33:927-932.

Rehmer, et al., Influence of Assembly Procedure and Material Combination on the Strength of the Taper Connection at the Head-Neck Junction of Modular Hip Endoprostheses, Clinical Biomechanics, 2012, 27:77-83.

Yoshio, et al., The Function of the Psoas Major Muscle: Passive Kinetics and Morphological Studies Using Donated Cadavers, Journal of Orthopaedic Science, 2002, 7:199-207.

PCT International Search Report and Written Opinion, PCT/US2013/062203, dated Mar. 3, 2014.

European Patent Office, Extended European Search Report, Application No. 13842034.4, dated Nov. 18, 2016.

* cited by examiner

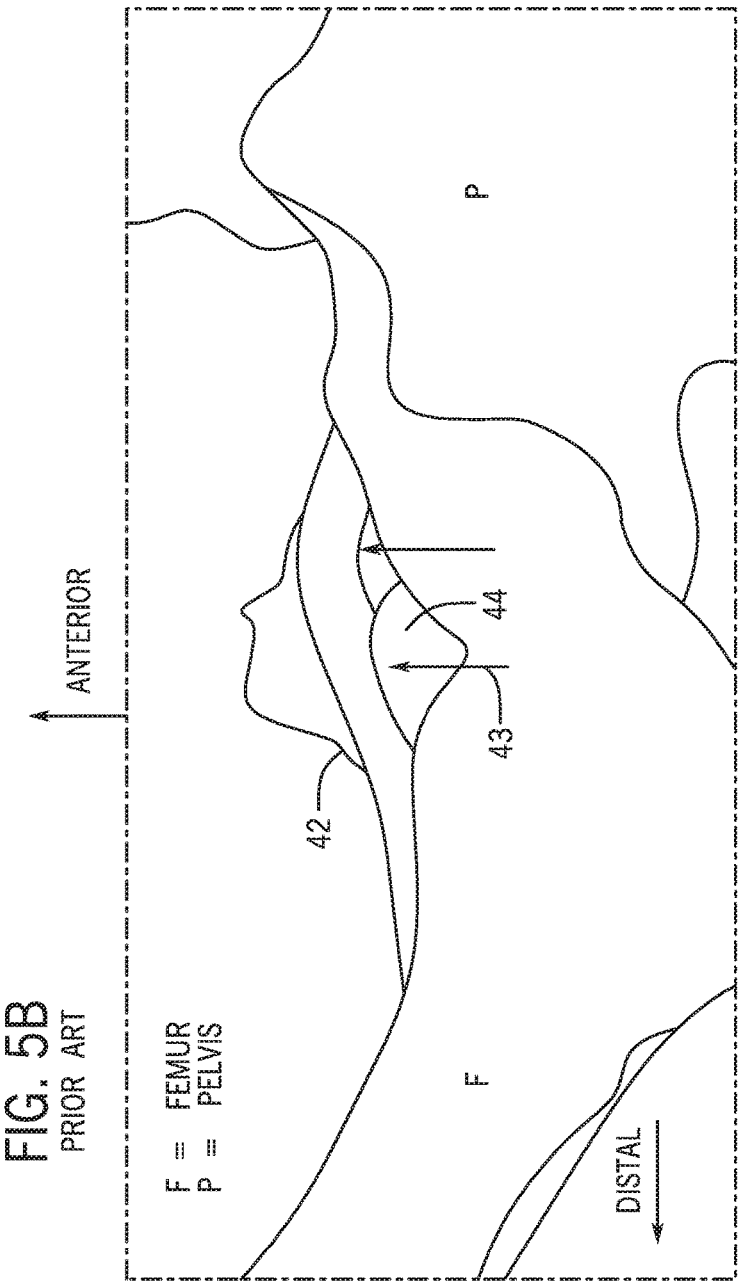

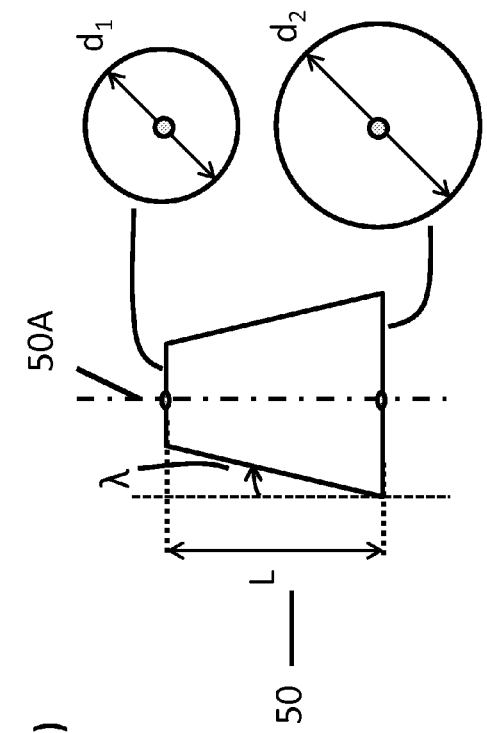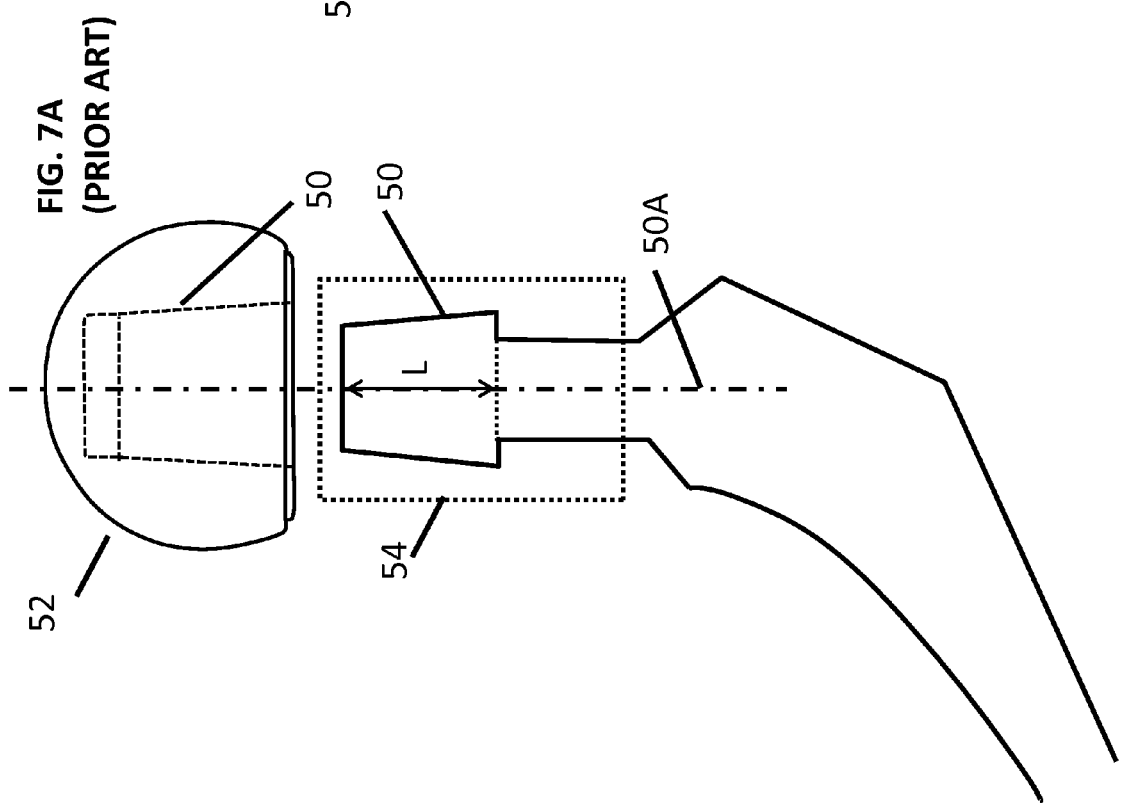

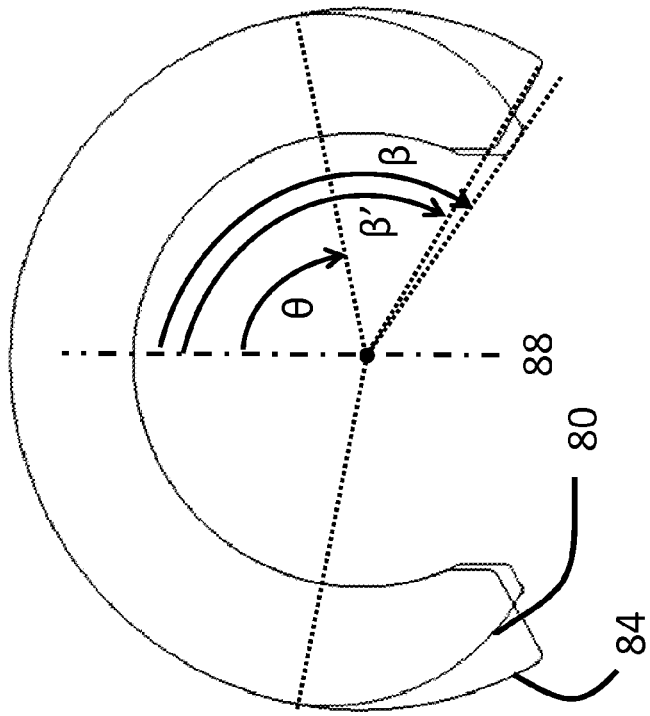
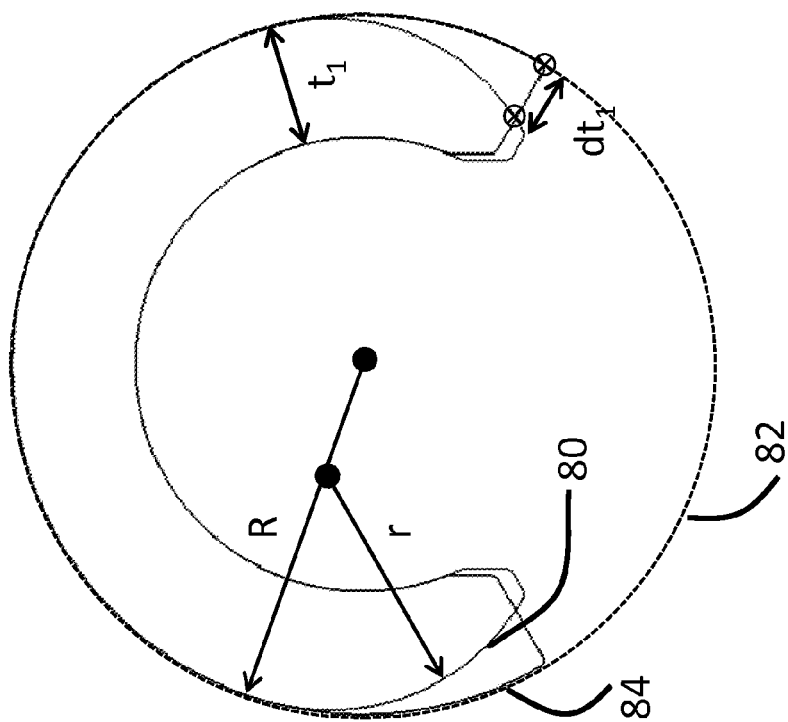
FIG. 12A
FIG. 12B

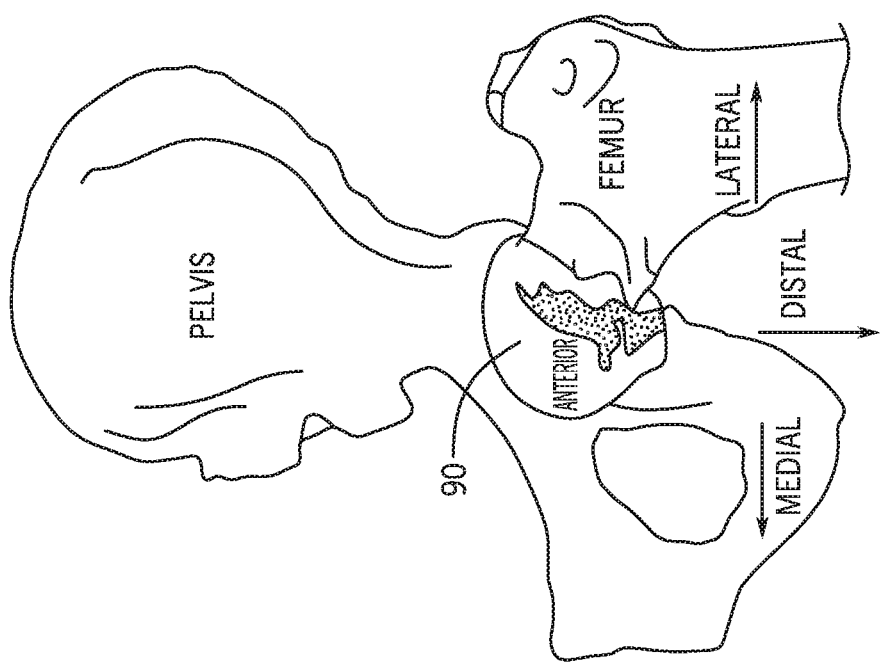

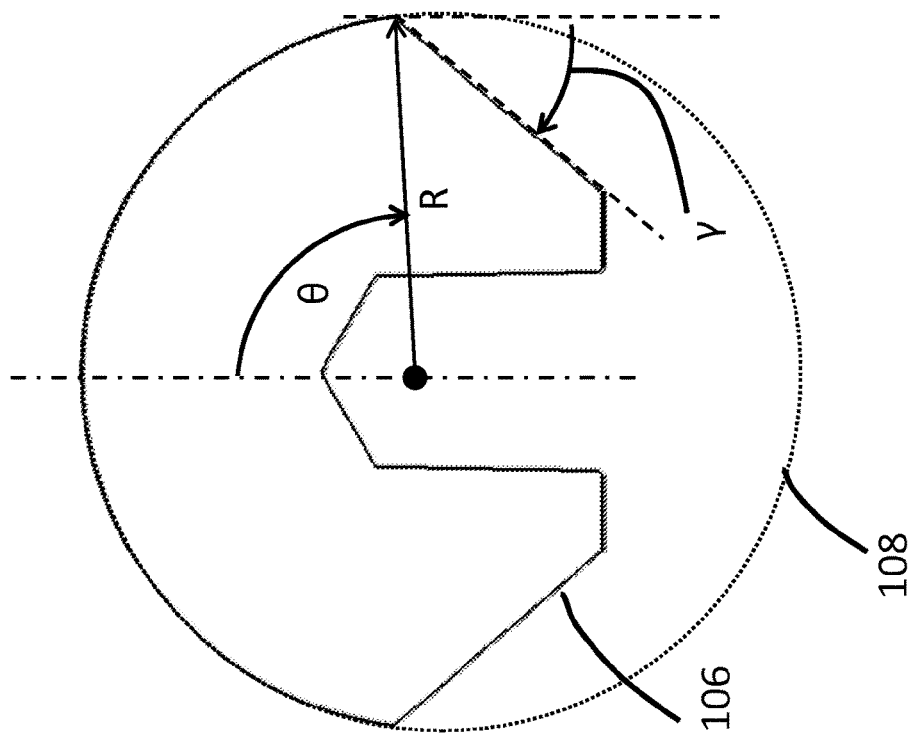
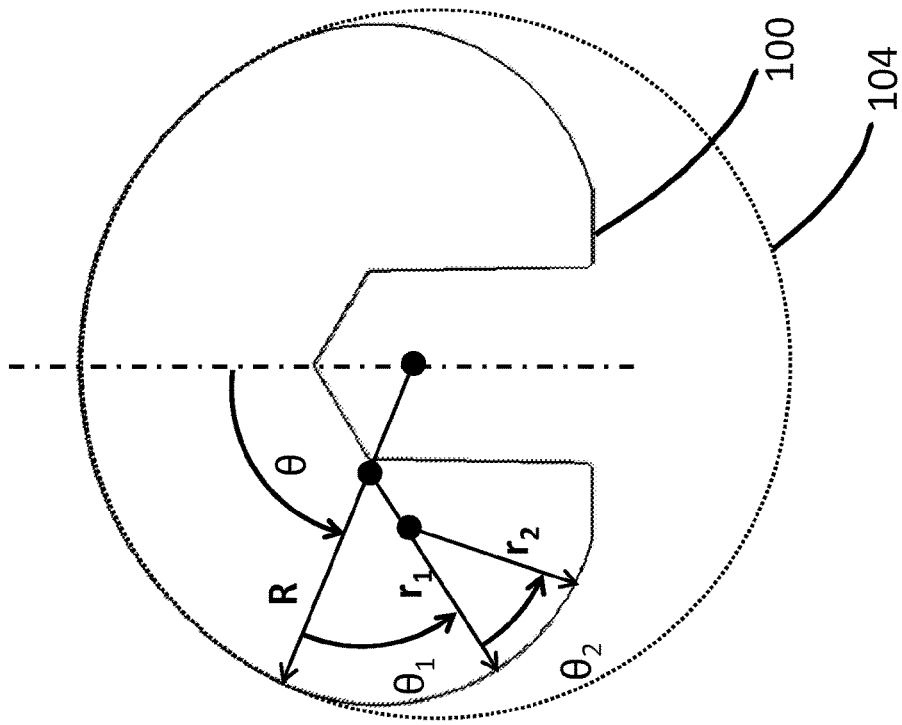
FIG. 16A
FIG. 16B

Contact area between femoral head and acetabular liner under peak loads corresponding to different activities of daily living

| In vivo Activity | Conventional femoral head 152 (R =18mm) | First femoral head 150 (R=18mm, θ = 90deg) | Femoral head 148 (R=18mm, θ = 80deg) |
|---|---|---|---|
| Walking | 1583 mm² | 1583 mm² [0%] | 1459 mm² [-8%] |
| Deep Knee Bend | 1894 mm² | 1894 mm² [0%] | 1610 mm² [-15%] |
| Chair sit-stand | 1569 mm² | 1569 mm² [0%] | 1316 mm² [-16%] |

FIG. 25

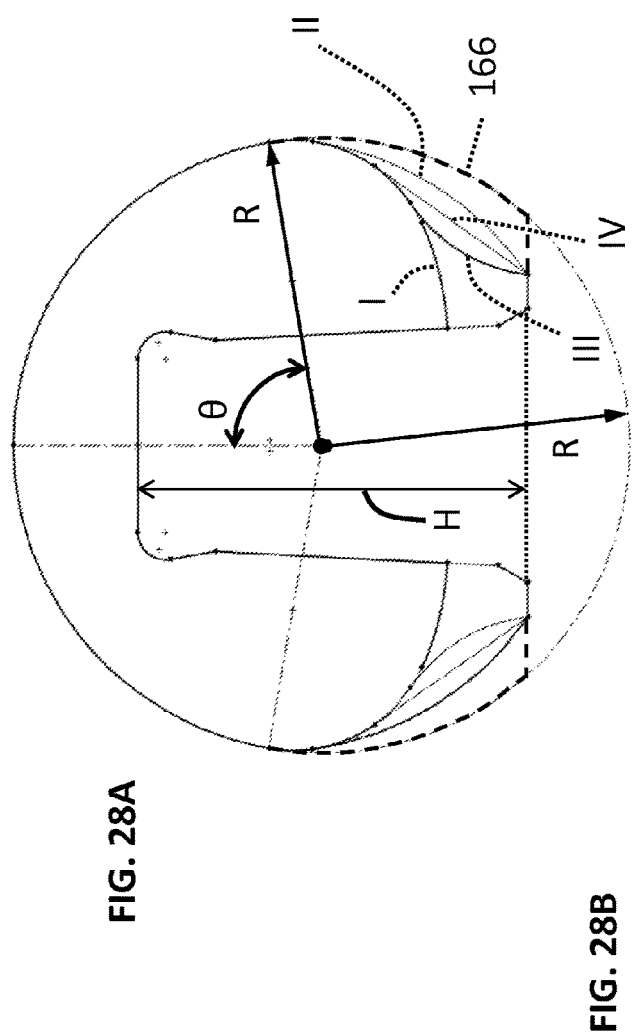
FIG. 28A
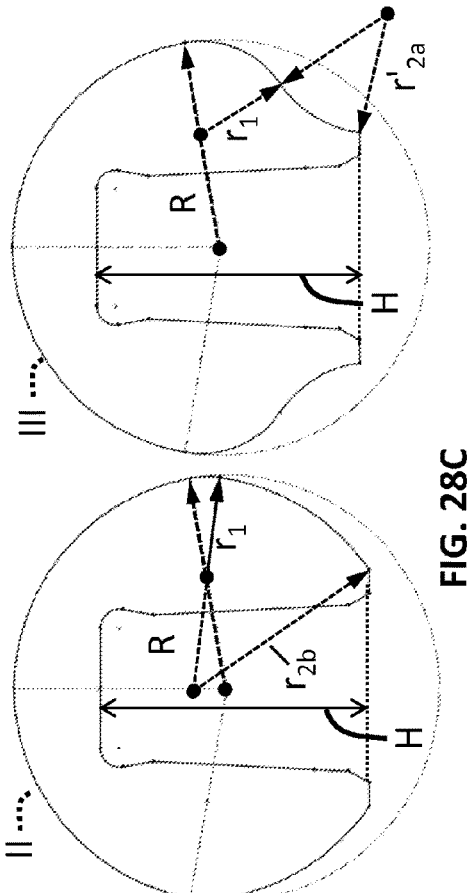
FIG. 28D
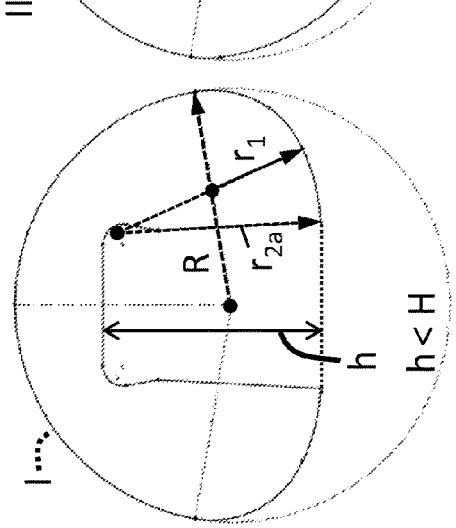
FIG. 28C
FIG. 28B

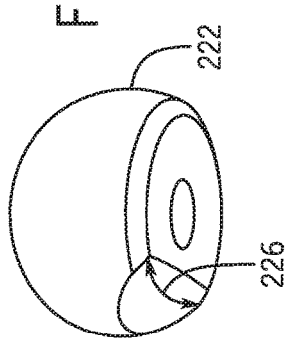
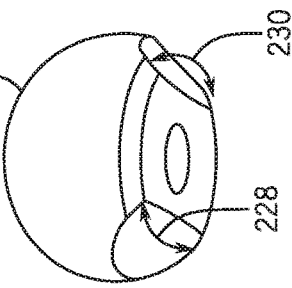
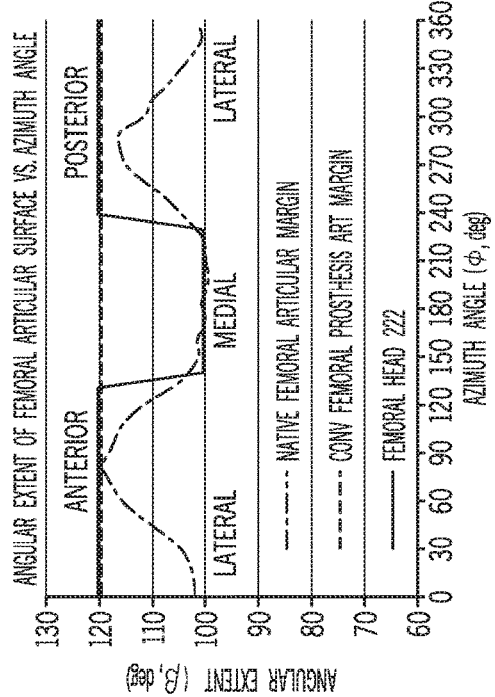
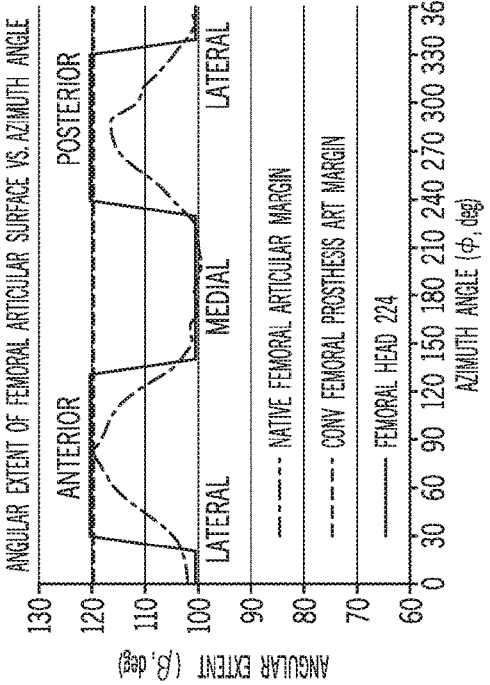

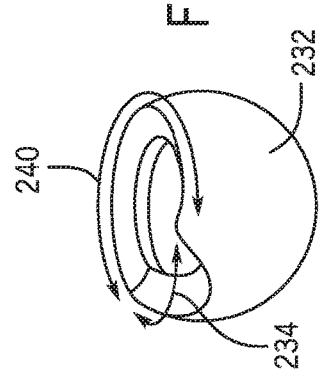
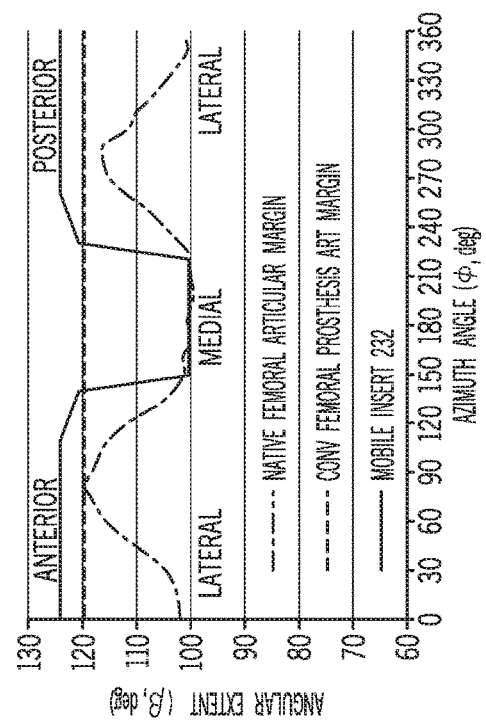
FIG. 33A
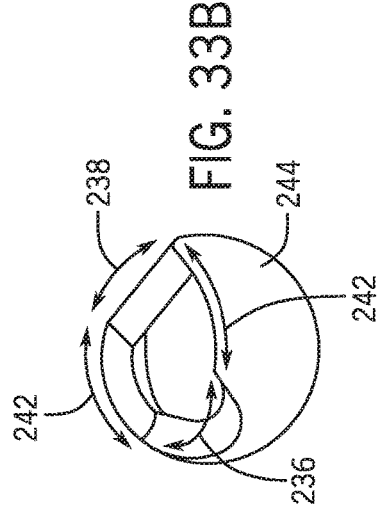
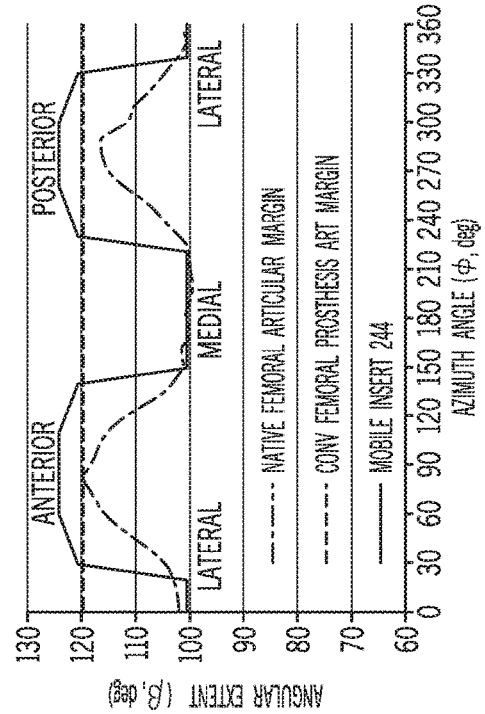
FIG. 33B

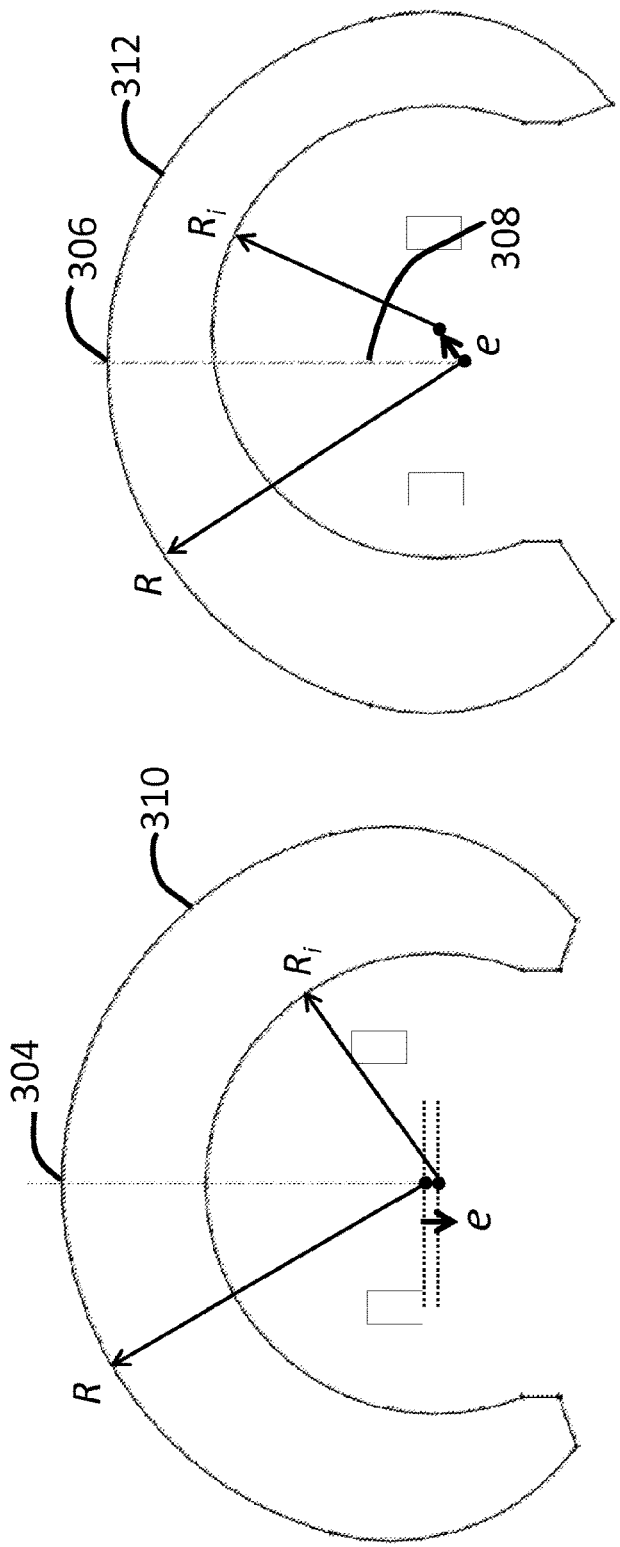

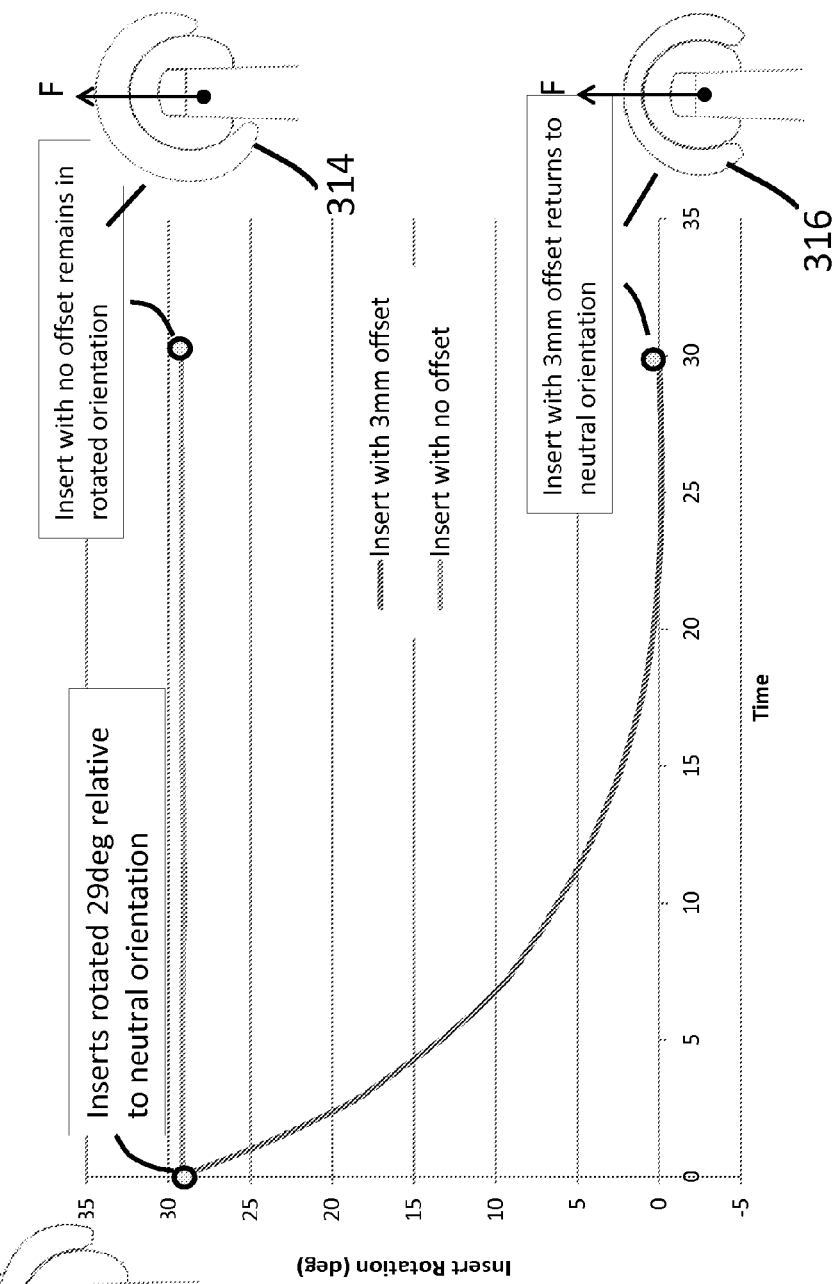
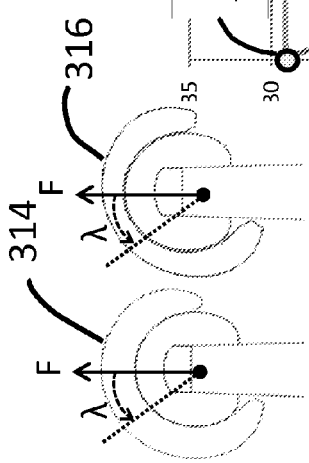
FIG. 39A
FIG. 39B
Mobile Insert Rotation (deg) vs. Time (sec)

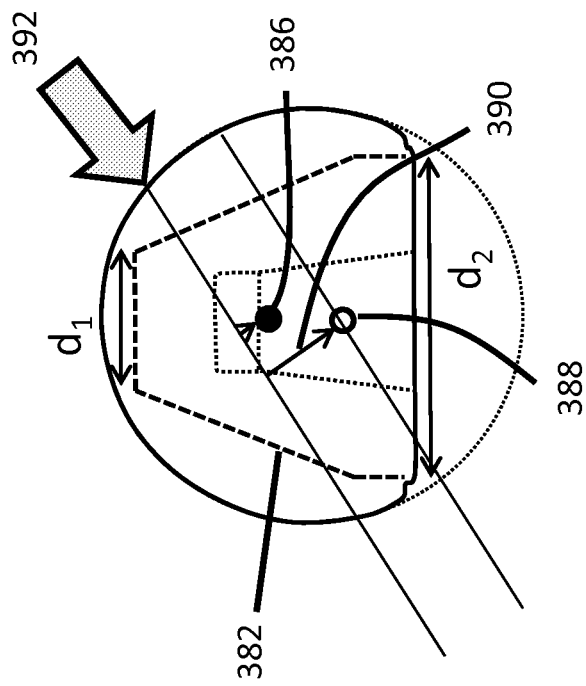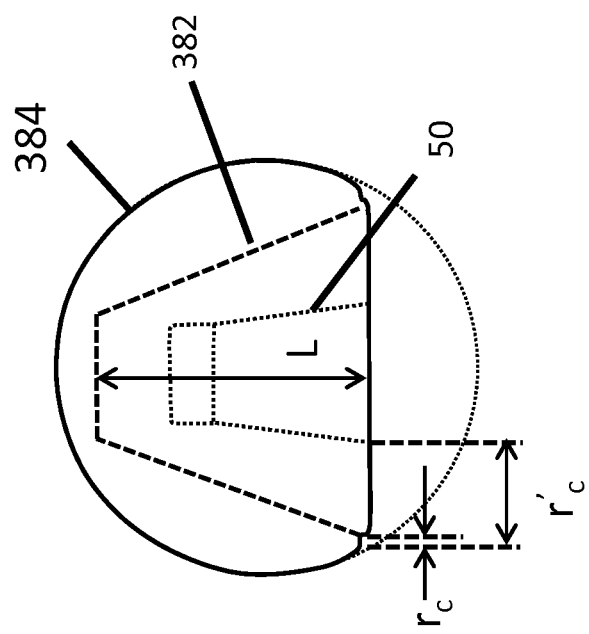
FIG. 50A
FIG. 50B

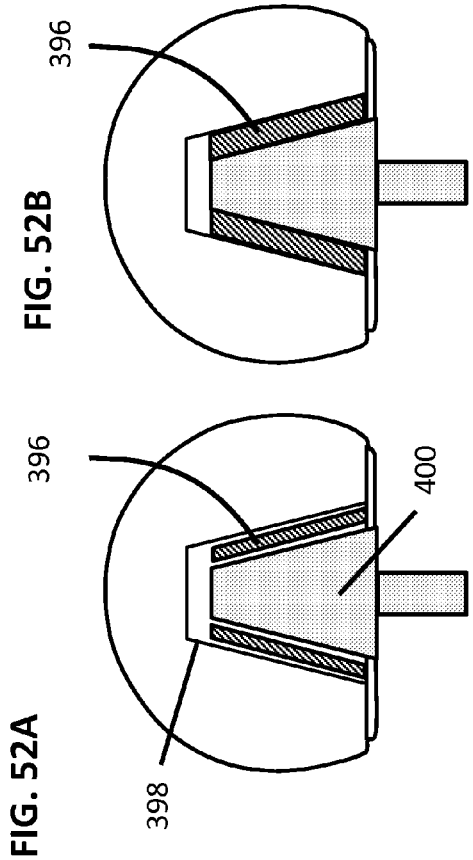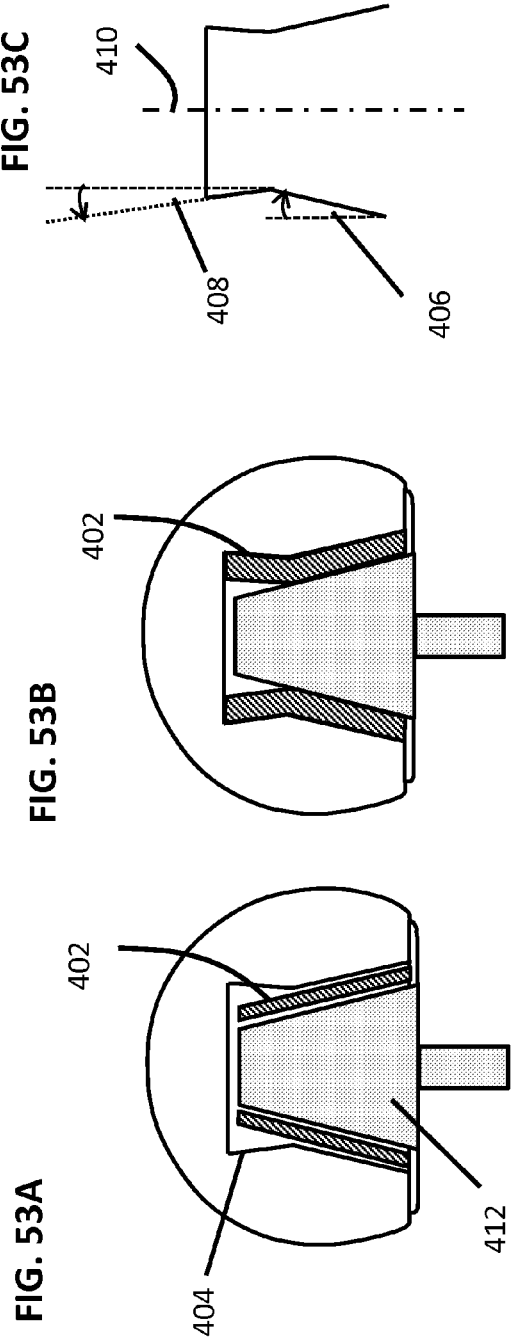

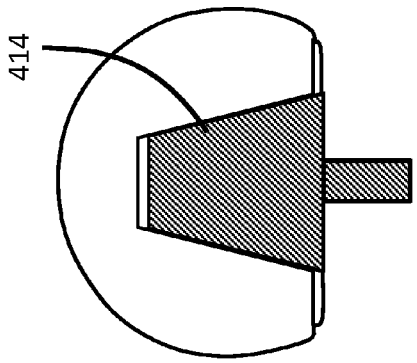
FIG. 54A  FIG. 54B
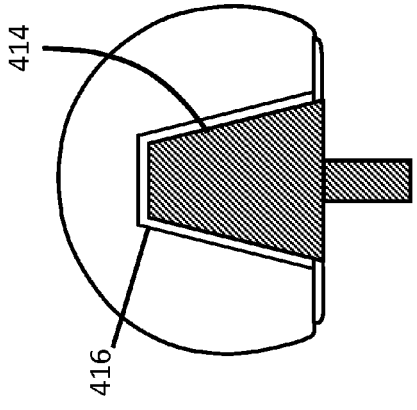
FIG. 55A  FIG. 55B
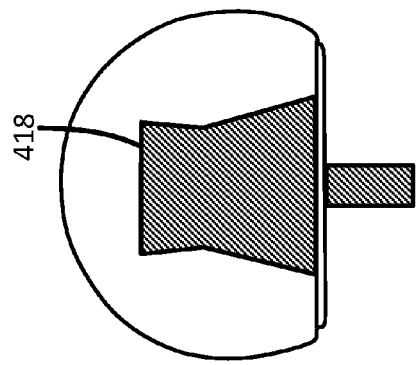
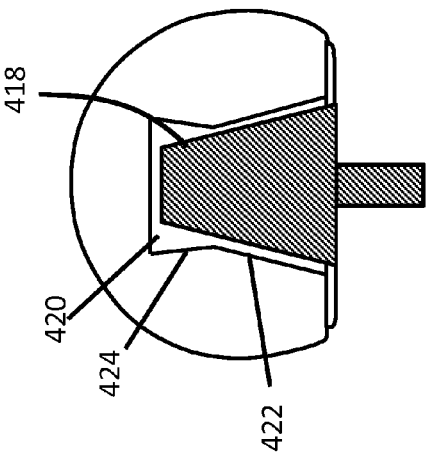

ized in the Korean

FEMORAL HEADS, MOBILE INSERTS, ACETABULAR COMPONENTS, AND MODULAR JUNCTIONS FOR ORTHOPEDIC IMPLANTS AND METHODS OF USING FEMORAL HEADS, MOBILE INSETS, ACETABULAR COMPONENTS, AND MODULAR JUNCTIONS FOR ORTHOPEDIC IMPLANTS

CROSS REFERENCE TO RELATED APPLICATIONS

The present application is a continuation application of U.S. patent application Ser. No. 14/039,287 filed Sep. 27, 2013 which claims priority to U.S. Prov. Pat. App. No. 61/706,439 entitled "Dual Mobility Hip Replacement Implants And Methods Of Using Dual Mobility Hip Replacement Implants" filed Sep. 27, 2012, U.S. Prov. Pat. App. No. 61/706,449 entitled "Modular Junctions For Orthopedic Implants And Methods Of Using Modular Junctions For Orthopedic Implants" filed Sep. 27, 2012, U.S. Prov. Pat. App. No. 61/706,426 entitled "Femoral Heads For Hip Replacement Implants And Methods Of Using Femoral Heads For Hip Replacement Implants" filed Sep. 27, 2012, and U.S. Prov. Pat. App. No. 61/784,272 entitled "Femoral Heads And Modular Junctions For Hip Replacement Implants And Methods Of Using Femoral Heads And Modular Junctions For Hip Replacement Implants" filed Mar. 14, 2013, which are hereby incorporated by reference in their entireties.

FIELD OF THE INVENTION

The present invention relates to femoral heads, mobile inserts, acetabular components, and modular junctions for orthopedic implants and methods of using femoral heads, mobile inserts, acetabular components, and modular junctions for orthopedic implants.

BACKGROUND OF THE INVENTION

Dislocation of the hip joint is a major cause of failure in hip arthroplasty. The reported incidences of hip dislocations range from 0.5% to 5.8% for primary surgeries and from 4.8% to 13% for revision surgeries. (See Burroughs et al. "Range Of Motion And Stability In Total Hip Arthroplasty With 28-, 32-, 38-, and 44-mm Femoral Head Sizes," *J Arthroplasty* 2005 January, 20(1):11-9.) Additionally, a large proportion (30% to 65%) of these dislocations become recurrent. (See previously mentioned Burroughs et al.) To reduce the risk against hip dislocations, large diameter (greater than about 32 mm) femoral heads and mating acetabular components are used in a variety of hip arthroplasty implants such as total hip implants, resurfacing hip implants, and dual mobility (DM) hip implants.

As shown in FIG. 1, a conventional total hip implant is generally composed of an acetabular shell 10 that mounts on the native pelvic bone and replaces the native acetabulum, an acetabular liner 12 affixed immovably to the acetabular shell 10, a prosthetic femoral head 14 that replaces the native femoral head, and a femoral stem 16 that attaches to the prosthetic femoral head 14 via a femoral neck 18. Some hip arthroplasty implants, such as metal-on-metal implants and resurfacing implants, do not have an acetabular liner, and the femoral head articulates directly with the acetabular shell. FIGS. 2A and 2B illustrate conventional large diameter femoral heads used in hip resurfacing (FIG. 2A) and total hip implants (FIG. 2B). The femoral head diameter equals 2*R, where R is a radius of an overall spherical geometry 22 of the femoral heads. Prosthetic femoral heads with diameters of about 32 mm or greater are defined as large diameter, and this diameter is close to that of the patient's native femoral head. In contrast, femoral heads with diameters of about 28 mm or less are defined as small diameter, and this diameter is smaller than that of the native femoral head.

As shown in FIGS. 3A and 3B, a conventional dual mobility hip implant is generally composed of an acetabular shell 24, a mobile insert 26, and a small diameter femoral head 28 attached to a femoral stem 30. The acetabular shell 24 mounts on the native pelvic bone and replaces the native acetabulum, and the femoral stem 30 attaches to the femoral head 28 via a femoral neck 32. An outer surface of the mobile insert 26 articulates with the acetabular shell 24 to form an outer articulation. An inner surface of the mobile insert 26 articulates with the small diameter head 28 retained within the insert 26 to form an inner articulation. An outer diameter of the mobile insert 26 is typically about 36 mm or greater. In contrast, the femoral head 28 retained within the mobile insert 26 typically has a diameter of about 28 mm or less. The larger diameter (2*R) outer articulation between the acetabular shell 24 and the mobile insert 26 provides stability against dislocation and provides large range of motion. The small diameter (2*R$_i$) inner articulation between the mobile insert 26 and the femoral head 28 provides a low wear articulation. Extraction or dislocation of the small diameter head 28 from the inner articulation is prevented by retention of the head 28 within the mobile insert 26. This retention is achieved by having the inner articular surface of the mobile insert 26 designed to cover and capture more than a hemispherical portion of the femoral head. Parameter β in FIGS. 2A and 2B characterizes an angular extent of an outer articular surface 30 of a femoral head, and parameter β in FIG. 4 characterizes an angular extent of an outer articular surface 32 of a mobile insert.

While large diameter femoral heads and mobile inserts provide increased resistance to hip dislocation, one of the concerns with conventional designs is the potential impingement against native soft tissues, such as the hip capsule and the iliopsoas muscle/tendon (see FIGS. 5A, 5B, 6A, and 6B). Impingement of these soft tissues can lead to severe groin pain. FIG. 5A shows that the iliopsoas tendon 34 in the native hip passes over the native femoral head 36 and femoral neck 38 to insert into the lesser trochanter 40. FIG. 5B shows that the iliopsoas tendon 42 articulating against the native femoral head 44 in a cadaver human hip joint (see Yoshio et. al. "The Function Of The Psoas Major Muscle: Passive Kinetics And Morphological Studies Using Donated Cadavers," J Orthop Sci. 2002, 7:199-207). Arrow 43 indicates a location of iliopsoas articulation against the native femoral head 44. FIGS. 6A and 6B show a conventional large diameter femoral head or mobile insert 46 mounted on a computer tomography (CT) based bone model of a cadaver specimen including a femur 47 and a pelvis 49. The articular surface of the prosthetic femoral head or mobile insert can be seen in FIGS. 6A and 6B to overhang 48 the articular surface of the native femoral head, particularly in the anterior-distal/anterior-medial and posterior-distal/posterior-medial regions. Acetabular shells and acetabular liners have been proposed to address potential soft tissue impingement. (See US Pat. Pub. No. 2005/0060040 filed Sep. 9, 2004 entitled "Prosthetic Acetabular Cup And Prosthetic Femoral Joint Incorporating Such A Cup," Intl. Pat. No. WO 2009118673 filed Mar. 20, 2009 entitled "Cotyloidal Prosthesis Of The So-Called 'Dual Mobility' Type," US Pat. Pub.

No. 2011/0301654 filed Jul. 29, 2011 entitled "Hip Resurfacing," and U.S. Pat. No. 7,169,186 filed May 15, 2002 entitled "Monopolar Constrained Acetabular Component.")

Another complication relating to use of large diameter femoral heads and mobile inserts is increased wear and/or frictional torque at the femoral head-acetabular articulation or mobile insert-acetabular articulation. (See Lachiewicz et al. "Femoral Head Size and Wear of Highly Cross-linked Polyethylene at 5 to 8 Years," *Clin Orthop Relat Res.* 2009 December, 467(12): 3290-3296; Livermore et al. "Effect of Femoral Head Size on Wear of the Polyethylene Acetabular Component," *J Bone Joint Surg Am.* 1990 April, 72-A: 518-528.)

Yet another complication of using large diameter femoral heads and mobile inserts is increased risk of failure of the modular junctions used in many modern hip implants. Such modular junctions are used for increased flexibility in matching a patient's anatomy and achieving optimal component positioning (see, e.g., a modular taper junction 20 of FIG. 1). A modular femoral head-neck junction, for example, implies that the femoral head is a separate component that is assembled onto the femoral neck. As shown in FIGS. 7A and 7B, conventional modular junctions of a femoral head 52 and a femoral neck 54 are typically conical taper junctions 50, with a small diameter circular profile d1 at one end of the taper junction 50 that increases in size to a circular profile of diameter d2 at an opposite end of the taper junction 50. A parameter L represents a length of the taper junction 50 measured along a taper junction axis 50A, and a parameter $\lambda$ represents a conical angle of mating surfaces of the taper junction 50. In a conventional femoral head-neck taper junction, the taper junction axis is generally also parallel to the prosthetic femoral neck axis, as in FIGS. 7A and 7B.

Recent studies have shown that taper junctions are susceptible to corrosion due to micromotion at the mating surfaces. (See Lieberman et al. "An Analysis Of The Head-Neck Taper Interface In Retrieved Hip Prostheses," *Clin Orthop Relat Res.* 1994 March, (300):162-7; Rehmer et al. "Influence Of Assembly Procedure And Material Combination On The Strength Of The Taper Connection At The Head-Neck Junction Of Modular Hip Endoprostheses," *Clin Biomech.* 2012 January, 27(1):77-83.) This in turn can lead to loosening of the modular junction and create undesirable metal debris. Hip implants with large diameter femoral heads and mobile inserts are particularly susceptible to this due to the increased lever arm and implant diameter, which can lead to greater frictional torque and moment loads at the junction. (See Meyer et al. "Corrosion at the Cone/Taper Interface Leads to Failure of Large-diameter Metal-on-metal Total Hip Arthroplasties," *Clin Orthop Relat Res.* 2012 Aug. 3. [Epub ahead of print]; Langton et al. "Taper Junction Failure In Large-Diameter Metal-On-Metal Bearings". *Bone Joint Res.* 2012 September, 1(4): 56-63.)

Accordingly, there remains a need for improved orthopedic implants.

SUMMARY OF THE INVENTION

The present invention relates to femoral heads, mobile inserts, acetabular components, and modular junctions for orthopedic implants and methods of using femoral heads, mobile inserts, acetabular components, and modular junctions for orthopedic implants.

In one aspect, an orthopedic implant is provided that in one embodiment includes a femoral head implant that includes a peripheral portion of an outer surface thereof that is contoured so as to achieve an inward shift of the outer surface relative to an overall spherical geometry of the femoral head implant. The inward shift is achieved through a change in radius of curvature, the radius of curvature being one or more convex radii. The inward shift is axisymmetric around a femoral head axis of the femoral head implant and occurs at an angle greater than about 80° and less than about 115°. The inward shift is at least about 1 mm at a location of maximum inward shift.

In another embodiment, an orthopedic implant includes a femoral head implant having a portion of an outer surface thereof that is contoured so as to achieve an inward shift of the outer surface relative to an overall spherical geometry of the femoral head implant. The inward shift reduces at least one of soft tissue impingement and frictional torque.

The orthopedic implant can vary in any number of ways. For example, the inward shift of the outer surface relative to an overall spherical geometry of the femoral head implant can be achieved through a change in radius of curvature, the radius of curvature including one or more of convex radii, concave radii, and chamfers. For another example, the inward shift of the outer surface relative to an overall spherical geometry of the femoral head implant can be achieved through a change in center of curvature. For yet another example, the inward shift of the outer surface relative to an overall spherical geometry of the femoral head implant can be achieved through creation of grooves, cut-outs, or recesses. For still another example, the inward shift of the outer surface relative to an overall spherical geometry of the femoral head implant can be axisymmetric around a femoral head axis of the femoral head implant. The portion can be a peripheral portion, and the inward shift of the outer surface relative to an overall spherical geometry of the femoral head implant can be at least about 1 mm at a location of maximum inward shift, the inward shift of the outer surface relative to an overall spherical geometry of the femoral head implant can occur at the angle, the inward shift of the outer surface relative to an overall spherical geometry of the femoral head implant can be achieved using one or more of convex radii, concave radii, and chamfers, the inward shift of the outer surface can be achieved using a convex radius or convex radii that immediately follow a non-contoured surface, the inward shift of the outer surface can be configured to approach edges of a taper junction, and/or the inward shift of the outer surface can be configured to merge with an extended portion of a taper junction. The convex radius or convex radii can be followed by concave radii or chamfers, or a combination of one or more concave radii and chamfers. For another example, the inward shift of the outer surface relative to an overall spherical geometry of the femoral head implant can be non-axisymmetric around a femoral head axis of the femoral head implant. The inward shift of the outer surface can be configured to occur over a limited range of azimuth angle measured around a femoral head axis of the femoral head implant, thereby leading to creation of at least one of localized cut-outs and localized recesses. The inward shift of the outer surface can be axisymmetric about another axis that is at not coincident with the femoral head axis. The inward shift of the outer surface relative to an overall spherical geometry of the femoral head implant can be achieved using one or more of convex radii, concave radii, and chamfers.

In another embodiment, an orthopedic implant includes a femoral head implant having a portion of an outer surface that has varying angular extent as a function of azimuth angle measured around a femoral head axis of the femoral head implant.

In another embodiment, an orthopedic implant includes a femoral head implant having portions of an outer surface that are removed so as to reduce a contact area with a mating surface, the mating surface including an articular surface of an acetabular component.

In another embodiment, an orthopedic implant includes a femoral head implant has portions of an outer surface that are removed by texturing so as to reduce a contact area with a mating surface. The mating surface can include an articular surface of an acetabular component.

The orthopedic implant can vary in any number of ways. For example, the outer surface can be textured so as to reduce the contact area with the mating surface.

In another embodiment, an orthopedic implant includes a mobile insert that includes a portion of an inner or outer surface thereof that is contoured so as to achieve an inward shift of the inner or outer surface relative to an overall spherical geometry of the mobile insert, thereby reducing at least one of soft tissue impingement and frictional torque.

The orthopedic implant can vary in any number of ways. For example, the inward shift of the inner or outer surface relative to the overall spherical geometry of the mobile insert can be achieved through a change in radius of curvature. The radius of curvature can include one or more of convex radii, concave radii, and chamfers. For another example, the inward shift of the inner or outer surface relative to the overall spherical geometry of the mobile insert can be achieved through a change in center of curvature. For yet another example, the inward shift of the inner or outer surface relative to the overall spherical geometry of the mobile insert can be achieved through creation of grooves, cut-outs or recesses.

In another embodiment, an orthopedic implant includes a mobile insert having a portion of an inner or outer surface thereof that has varying angular extent as a function of azimuth angle measured around a mobile insert axis of the mobile insert.

In another embodiment, an orthopedic implant includes a mobile insert, A range of permissible motion between the mobile insert and one of an acetabular component and a femoral head is different along one direction compared to a range of permissible motion in another direction.

In another embodiment, an orthopedic implant includes a mobile insert in which portions of an inner or outer surface of the mobile insert are removed sp as to reduce a contact area with a mating surface. The mating surface includes an articular surface of a femoral head or of an acetabular component.

The orthopedic implant can vary in any number of ways. For example, the inner or outer surface can be textured so as to reduce contact area with the mating surface.

In another aspect, a modular taper junction is provided that in one embodiment is configured to connect together a plurality of separate components forming an orthopedic implant. The modular taper junction can include a first component with an inner surface, and a second component with an outer surface. The inner surface of the first component and the outer surface of the second component can have non-circular cross-sectional geometry in a plane perpendicular to a taper junction axis of the modular taper junction. The first component can include a cavity.

In another embodiment, a modular taper junction configured to connect together a plurality of separate components forming an orthopedic implant can include a first component with an inner surface, and a second component with an outer surface. A portion of at least one of the first and second components can be composed of one or more shape memory materials. The first component can include a cavity.

In another embodiment, a modular taper junction configured to connect together a plurality of separate components forming an orthopedic implant can include a first component with an inner surface, a second component with an outer surface, and a sleeve with an inner surface and an opposite outer surface. The sleeve can be composed at least partially of one or more shape memory materials, and the sleeve can be interposed between the inner surface of the first component and the outer surface of the second component. The outer surface of the sleeve can be configured to mate with the inner surface of the first component, and the inner surface of the sleeve can be configured to mate with the outer surface of the second component. The first component can include a cavity.

In another embodiment, a modular taper junction configured to connect together a plurality of separate components forming an orthopedic implant can include a first component with an inner surface and a second component with an outer surface. At least one of the inner surface of the first component and the outer surface of the second component can have a part positive and part negative taper angle. The part positive and negative taper angles can be angled in an opposite directions relative to a taper junction axis of the modular taper junction. The first component can include a cavity.

BRIEF DESCRIPTION OF THE DRAWINGS

The invention will be more fully understood from the following detailed description taken in conjunction with the accompanying drawings, in which:

FIG. 5B (PRIOR ART) is a lateral view of a hip joint of a cadaver specimen, showing the iliopsoas tendon articulating against the native femoral head;

FIG. 7A (PRIOR ART) is a schematic view of a conventional hip implant with a modular femoral head-neck junction, the modular junction being a conical taper junction;

FIG. 7B (PRIOR ART) is another schematic view of the modular femoral head-neck junction of FIG. 7A;

FIG. 12A is a schematic view of a conventional mobile insert superimposed on an embodiment of a mobile insert showing a first set of measurement variables;

FIG. 12B is a schematic view of the conventional mobile insert of FIG. 12A superimposed on the mobile insert of FIG. 12A showing a second set of measurement variables;

FIG. 14A (PRIOR ART) is a perspective view of a conventional femoral head mounted on a computer tomography (CT) based bone model of a cadaver specimen;

FIG. 16A is a schematic view of an embodiment of a femoral head showing a set of measurement variables, the femoral head having a contoured peripheral surface created using multiple convex radii;

FIG. 16B is a schematic view of an embodiment of a femoral head showing a set of measurement variables, the femoral head having a contoured peripheral surface created using a chamfer;

FIG. 25 is a table summarizing contact area between a femoral head and an acetabular liner for different embodiments of a femoral head compared to a conventional femoral head under loads corresponding to different activities of daily living;

FIG. 28A is a schematic view of a conventional femoral head superimposed on different embodiments of femoral heads;

FIG. 28B is a schematic view of one embodiment of a femoral head from FIG. 28A. In this embodiment the peripheral contouring is achieved with 2 convex radii, resulting in a reduction of the taper junction length relative to the conventional design.

FIG. 28C is a schematic view of one embodiment of a femoral head from FIG. 28A. In this embodiment the peripheral contouring is achieved with 2 convex radii, while retaining the taper junction length of the conventional design.

FIG. 28D is a schematic view of one embodiment of a femoral head from FIG. 28A. In this embodiment the peripheral contouring is achieved with a convex radius and a concave radius to retain the taper junction length of the conventional design.

FIG. 32A is a perspective view of an embodiment of a non-axisymmetric femoral head with a medial articular surface trimmed to match the native femoral head geometry, and a graph showing angular extent of articular surface versus azimuth angle measured about a femoral head axis;

FIG. 32B is a perspective view of an embodiment of a non-axisymmetric femoral head with medial and lateral articular surfaces trimmed (a form of contouring) to match the native femoral head geometry, and a graph showing angular extent of articular surface versus azimuth angle measured about a femoral head axis;

FIG. 33A is a perspective view of an embodiment of a non-axisymmetric mobile insert with a medial articular surface trimmed (a form of contouring) to match the native femoral head geometry, and showing angular extent of articular surface versus azimuth angle measured about a mobile insert axis;

FIG. 33B is a perspective view of an embodiment of a non-axisymmetric mobile insert with medial and lateral articular surfaces trimmed to match the native femoral head geometry, and a graph showing angular extent of articular surface versus azimuth angle measured about a mobile insert axis;

FIG. 38B is a schematic view of one embodiment of a mobile insert with offset of the inner articulation center away from the pole, relative to the outer articulation center;

FIG. 38C is a schematic view of one embodiment of a mobile insert wherein, relative to the outer articulation center the inner articulation center is offset towards the pole and away from the insert axis;

FIG. 39A shows two different embodiments of a mobile insert rotated from their neutral orientations;

FIG. 39B is a graph showing rotation of the two different embodiments of the mobile insert of FIG. 39A under the action of the compressive force;

FIG. 50A is a schematic view of one embodiment of a large taper junction of an orthopedic implant compared to a conventional implant; FIG. 50B is another schematic view of the large taper junction of the orthopedic implant compared to the conventional implant of FIG. 50A;

FIG. 52A is a schematic view of one embodiment of an orthopedic implant including a shape memory material sleeve, the sleeve being in a first state;

FIG. 52B is a schematic view of the sleeve of FIG. 52A in a second state;

FIG. 53A is a schematic view of another embodiment of an orthopedic implant including a shape memory material sleeve in a first state;

FIG. 53B is a schematic view of the sleeve of FIG. 53A in a second state;

FIG. 53C is a schematic view of the taper junction of the implant of FIG. 53A;

FIG. 54A is a schematic view of one embodiment of an orthopedic implant including a shape memory material femoral neck in a first state;

FIG. 54B is a schematic view of the femoral neck of FIG. 54A in a second state;

FIG. 55A is a schematic view of another embodiment of an orthopedic implant including a shape memory material femoral neck in a first state;

FIG. 55B is a schematic view of the femoral neck of FIG. 55A in a second state;

Figure 60B:
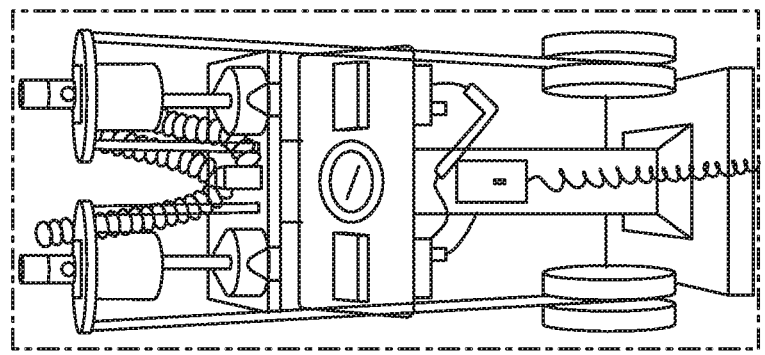
Figure 60A:
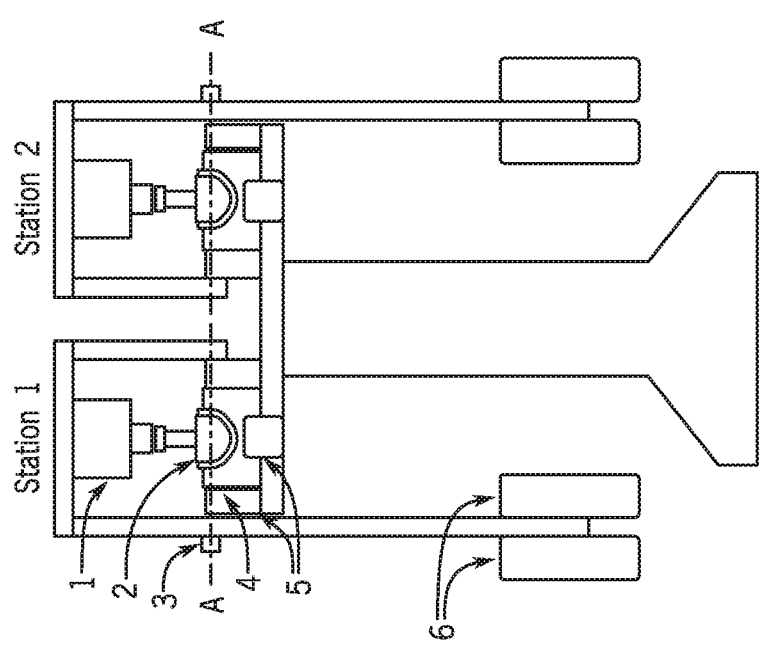
Figure 61:
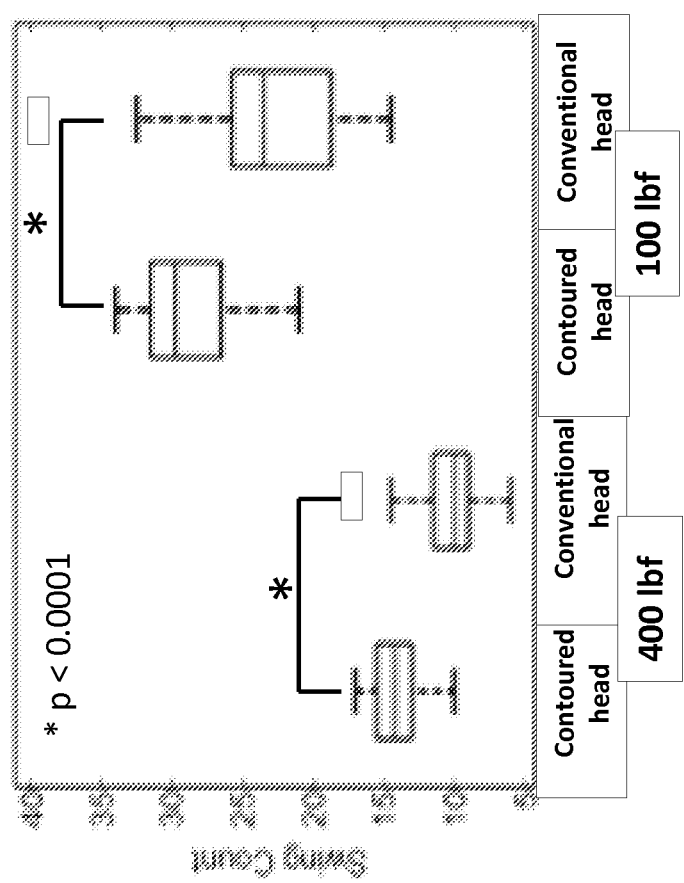

FIG. 60A is a side schematic view of a pendulum comparator machine that includes pneumatic pistons 1 configured to apply compressive load, ceramic head-liners 2, angle sensors 3, liner blocks 4, block clamps 5, weights 6, and a pendulum axis A-A;

FIG. 60B is a perspective view of a pendulum comparator machine that includes pneumatic pistons configured to apply compressive load, ceramic head-liners, angle sensors, liner blocks, block clamps, weights, and a pendulum axis; and FIG. 61 shows results of a pendulum comparator test comparing number of pendulum swings for a ceramic femoral head articulating against a ceramic acetabular liner, and a conventional ceramic femoral head articulating against a ceramic acetabular liner.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are exemplary embodiments and that the scope of the present invention is defined solely by the claims. The features illustrated or described in connection with one exemplary embodiment may be combined with the features of other embodiments. Such modifications and variations are intended to be included within the scope of the present invention. The definitions of various terms used to describe the present invention are provided below.

Definitions

The term "native" is used herein to imply natural or naturally occurring in the body. Examples of native structures include musculoskeletal structures such as the pelvic bone (or pelvis), femoral bone (or femur), tendon, muscle, ligament, joint capsule, etc. For example, what is meant by "native femoral head" is the natural anatomical structure that resides at a proximal end of a femur.

The term "implant" is used herein to refer to a prosthetic component designed to augment or replace one or more native structures of the body. For example, an orthopedic implant refers to a prosthetic component designed to augment or replace one or more native musculoskeletal structures of the body.

The term "modular junction" used herein refers to a portion of an implant that marks an interface between discrete implant components and is designed to rigidly hold the components together. The term "taper junction" is used herein to refer to a modular junction composed of a first component with an inner surface (e.g., a female taper surface) that mates with an outer or exterior surface of a second component (e.g., a male taper surface) The term "conical taper junction" as used herein refers to a taper junction where mating surfaces thereof have a conical geometry composed of a small diameter circular profile at one end of the junction that increases in size to a larger diameter circular profile at another, opposite end of the junction. Such conical taper junctions are also referred to as taper, morse taper, morse taper junction, trunnion, taper connection, etc. The term "taper junction axis" as used herein refers to a line joining geometric centers of two ends of a taper junction. For example, in a conical taper junction, the taper junction axis is a line joining centers of circular profiles at two ends of the junction. An "extended portion" of a taper junction refers herein to a portion a prosthetic component that extends beyond a main body of the prosthesis and includes a surface (male or female taper surface) of the taper junction. For example, in a femoral head implant, a female taper surface is generally formed by an inner surface of a cavity within a main spherical/semi-spherical body of the femoral head. However, in some femoral head implants, a cylindrical protrusion extends from a base of the femoral head. In this implant, the female taper surface extends from the cavity in the main spherical body of the femoral head to a cavity in this cylindrical protrusion. In this case, the cylindrical protrusion containing the female taper surface is referred to as an extended portion of a taper junction.

The terms "articulate," "articulation," and "articulating" are used herein to indicate a possibility of relative motion between mating surfaces. For prosthetic components, such relative motion is intended or part of the design intent. For example, the phrase "component A articulates with component B" indicates that relative motion can occur between component A and component B at the mating surface/s or interface/s. In some embodiments, an amount of relative motion at the articulating surfaces can be less than about 1 mm. In other embodiments, the amount of relative motion can be larger than about 1 mm, e.g., larger than about 2 mm, larger than about 5 mm, larger than about 10 mm, etc.

The term "articular surface" as used herein refers to a portion of a native musculoskeletal structure or a prosthetic component where relative motion (or articulation) can occur in relation to another native structure or prosthetic component.

The term "femoral head" or "head" as used herein refers to either a ball-shaped top of the native femoral bone that forms part of the native hip joint, or a prosthetic component or a portion of a prosthetic component designed to replace or augment the native femoral head or a portion of the native femoral head. In some embodiments, a prosthetic femoral head is in the form of a cap configured to primarily replace an outer surface of a native femoral head, and thereby minimize amount of bone removal required to affix the component to the native femur. In other embodiments, a prosthetic femoral head is spherical, semi-spherical, or ball-like. In yet other embodiments, the prosthetic femoral head is configured to replace the native femoral head. The prosthetic femoral head may be affixed to the native femur through a prosthetic femoral-neck and/or a prosthetic femoral stem. The prosthetic femoral head and femoral neck may be portions of a single implant (monoblock component) or may be separate/discrete components. The interface between a prosthetic femoral head and femoral neck may be a modular junction (femoral head-neck junction), such as a conical taper junction.

The term "femoral neck" or "neck" as used herein refers to either a portion of the native femur between the native femoral head and native femoral shaft (femoral body), or a prosthetic component or a portion of a prosthetic component that joins a prosthetic femoral head to the native femur or to a prosthetic femoral stem. The prosthetic femoral neck and femoral stem may be portions of a single implant (monoblock component) or may be separate/discrete components. The interface between a prosthetic femoral neck and femoral stem maybe a modular junction (femoral neck-stem junction), such as a conical taper junction.

The term "femoral neck axis" as used herein refers to an axis that is parallel to an axis of a cylindrical approximation of the femoral neck. The native femoral neck axis also passes through the center of the native femoral head. In conventional implants, the prosthetic femoral neck axis typically passes through the prosthetic femoral head center, and under ideal surgical placement the prosthetic femoral neck axis is expected to be parallel to the native femoral neck axis. However, in a number of surgical cases, the prosthetic femoral neck axis may not be parallel to the native femoral neck axis.

The term "femoral stem" or "stem" as used herein refers to a prosthetic component or a portion of a prosthetic component with an elongated distal end designed to be affixed to the native femur such as within the intra-medullary canal of the native femur.

The term "acetabulum" refers to the cup shaped cavity of the native pelvis that receives the native femoral head and forms a part of the native hip joint.

The term "acetabular component" as used herein refers to a prosthetic component configured to replace or augment the native acetabulum or a portion of the native acetabulum. The acetabular component can be composed of one or more sub-components such as an acetabular shell, an acetabular liner, and a mobile insert. The term "acetabular shell" as used herein refers to a prosthetic component whose outer surface is configured to be affixed immovably to the native acetabulum. When the acetabular shell mates with the native acetabulum, there can be limited relative motion between the two bodies. Typically, this limited relative motion is called micromotion and is on the order of about 1 mm or less. An inner/interior surface of the acetabular shell can articulate with the native femoral head, or it can articulate with a prosthetic femoral head, or mate with an acetabular liner, or articulate with a mobile insert. When the acetabular shell mates with an acetabular liner, there can be limited relative motion between the two bodies. Typically, this limited relative motion is called micromotion and is on the order of about 1 mm or less. The acetabular shell can be affixed immovably to the pelvic bone through various methods such as screws, bone cement, ingrowth of bone into the component surface, etc., or the acetabular shell be held in place by compressive forces in the hip joint. The term "acetabular liner" as used herein refers to a prosthetic component whose outer surface is configured to be affixed immovably to an inner surface of another acetabular component (e.g., an acetabular shell). An inner surface of the acetabular liner can be configured to articulate with a prosthetic femoral head, articulate with the native femoral head, mate with another acetabular liner, or articulate with a mobile insert. When the acetabular liner mates with another acetabular liner, there can be limited relative motion between the two bodies. Typically, this limited relative motion is called micromotion and is on the order of about 1 mm or less.

The acetabular liner can be rigidly fixed to the acetabular shell by various methods such as screws, locking mechanisms, capture mechanisms etc., or the acetabular liner can be held in place by compressive forces in the hip joint. The acetabular liner and acetabular shell can be a single monoblock component.

Monoblock components, such as an acetabular liner and acetabular shell combination, can be created via assembly process at an implant manufacturing facility. The term "mobile insert" or "insert" as used herein refers to a prosthetic component whose outer surface is configured to articulate with the inner surface of the native acetabulum, an acetabular shell, or an acetabular liner. An inner surface of the mobile insert can be configured to articulate with a prosthetic femoral head, to articulate with the native femoral head, to articulate with another mobile insert, or to mate with an acetabular liner. Thus, the term "mobile insert" as defined and used herein refers to a prosthetic component having an inner articular surface and an outer articular surface.

The term "overall spherical geometry" is used herein in relation to a surface of a prosthetic component, such as a femoral head or an acetabular component, or a surface of a native structure, such as the native femoral head or acetabulum. The term "overall spherical geometry" as used herein refers to a sphere of minimum radius that can fully encompass the surface and is tangent to the surface at a polar location (or pole or apex). A radius of the sphere is referred to as an "overall spherical radius." For example, an overall spherical geometry of an outer surface of a femoral head is a sphere of minimum radius that can fully encompass the surface and is tangent to the surface at a polar location. An articular surface of a conventional prosthetic femoral head or a mobile insert is typically more than a hemispherical portion of its overall spherical geometry. A femoral head diameter or head diameter typically equals two times the overall spherical radius of its outer articular surface. Similarly a mobile insert outer diameter typically equals two times the overall spherical radius of its outer articular surface.

The term "femoral head rim" as used herein refers to an edge or surface marking an end of a femoral head articular surface. A prosthetic femoral head rim can also mark the transition from the femoral head articular surface to a modular junction. Once the prosthetic components are implanted, the prosthetic femoral head rim can mark transition from prosthetic femoral head to native femoral head, prosthetic femoral head to native femoral neck, or prosthetic femoral head to prosthetic femoral neck. The native femoral head rim marks an end of the native femoral head articular surface and transition to the native femoral neck.

The term "mobile insert rim" as used herein refers to an edge or surface marking an end of the inner or outer articular surface of the mobile insert, and marks the opening to an inner cavity or inner surface of the mobile insert.

The term "acetabular rim" as used herein refers to an edge or surface of an acetabular component (liner or shell) that marks an end of an inner or outer surface of the acetabular component.

The term "femoral head axis" as used herein refers to a line passing through a center of an overall spherical geometry of a femoral head, and to a geometric center of a femoral head rim of the femoral head. Typically, the femoral head axis also passes through a polar location or pole or apex of the femoral head. The native femoral head axis is coincident with the native femoral neck axis. In conventional implants, the femoral head axis is typically parallel to the prosthetic femoral neck axis, and under ideal surgical placement the femoral head axis is expected to be parallel to the native femoral neck axis.

The term "mobile insert axis" as used herein refers to a line passing through a center of an overall spherical geometry of a mobile insert, and to a geometric center of a mobile insert rim of the mobile insert. Typically, the mobile insert axis also passes through a polar location or pole or apex of the mobile insert. In conventional implants, at neutral orientation and under ideal surgical placement, the mobile insert axis is typically parallel to the prosthetic femoral neck axis, and expected to be parallel to the native femoral neck axis.

The term "peripheral" as used herein refers to a portion of a prosthetic component adjacent to a prosthetic rim of the prosthetic component. For example, a peripheral portion of a femoral head or mobile insert refers to a portion of the femoral head or mobile insert which is adjacent to the femoral head rim or mobile insert rim, respectively.

The term "non-peripheral" as used herein refers to a portion of a prosthetic component which is not adjacent to a prosthetic rim of the prosthetic component. For example, a non-peripheral portion of a femoral head or mobile insert refers to a portion of the femoral head or mobile insert which is not adjacent to the femoral head rim or mobile insert rim, respectively.

A native structure or prosthetic component is described as being "axisymmetric" about an axis, as used herein, if cross-sections of the native structure or prosthetic component taken in a plane coincident with the axis have identical geometries at any location of the cross-sectional plane around the axis. Herein, the phrase "around the axis" implies in the direction of revolution about the axis, such as along a rim or circumference of the prosthetic component or native structure.

A native structure or prosthetic component is described as being "non-axisymmetric" about an axis, as used herein, if cross-sections of the native structure or prosthetic component taken in a plane coincident with the axis have non-identical geometries at different angular locations of the cross-sectional plane around the axis. Herein, "around the axis" implies in the direction of revolution about the axis, such as along a rim or circumference of the prosthetic component or native structure.

The term "angular extent," as used herein, characterizes an extent of a surface of a prosthetic component or a native structure such as an articular surface of a femoral head or mobile insert. In a femoral head or mobile insert, the angular extent is measured in a plane coincident with a femoral head axis or mobile insert axis and is an angle between the axis and a line joining a center of an overall spherical geometry of a surface to an end point of the surface.

The term "contoured" is used herein to refer to a surface that is shaped, formed, designed or fashioned in a specific manner as disclosed herein. The term "contouring" is used herein to refer to a process of shaping, forming, designing, or fashioning a surface in a specific manner. Such contouring can take the form of a change in radius, a change in center of curvature, creation of grooves, creation of cut-outs, creation of recesses, carving or trimming of the surface, etc. The term "non-contoured" when used in reference to a surface of a femoral head or mobile insert implies that the surface has a spherical geometry matching that of an overall spherical geometry of the head or insert.

The term "inwards" as used herein means toward the inside or toward the interior, such as toward or closer to a center of an overall spherical geometry. For example, a portion of an outer surface of a prosthetic femoral head can be contoured to move the surface inwards relative to an overall spherical geometry of the implant. This implies that a portion of the outer surface of the femoral head is moved toward an interior of the femoral head and closer to a geometric center of the overall spherical geometry. The term "inward shift" is used herein in relation to a surface of an implant contoured to move a surface inwards relative to an overall spherical geometry of the implant, and refers to a radial distance between the contoured surface and the overall spherical geometry. This radial distance is measured along a radial line of the overall spherical geometry.

The term "theta angle" refers to an angle between a line joining a center of an overall spherical geometry of a femoral head or mobile insert to a point on a surface of the femoral head or mobile insert, and the femoral head or mobile insert axis. In some embodiments, the point marks a location where a change in geometry of the femoral head or mobile insert surface occurs. The theta angle is measured in a plane coincident with the femoral head axis or mobile insert axis.

The term "azimuth angle" as used herein refers to an angle measured in a plane perpendicular to an axis. In relation to a mobile insert or femoral head, the azimuth angle is the angle between a line from the mobile insert or femoral head axis to a point on a surface of the mobile insert or femoral head, and another line from the mobile insert or femoral head axis to a reference location on the surface of the mobile insert or femoral head.

The term "chamfer" as used herein refers to a planar surface or edge that is not perpendicular to another planar surface or edge. A chamfer is also equivalent to a convex/concave surface or edge of very large radius.

The term "textured" is used herein in reference to a surface. A "textured" surface indicates presence of a network or series of raised and/or depressed features on the surface, or the presence of a network or series of grooves, valleys, or troughs. The term "texturing" as used herein refers to a process of creating such a textured surface.

The terms "polar location", "pole," and "apex" are used interchangeably herein in reference to generally spherical geometries such as a femoral head or a mobile insert. The polar location, pole, or apex of a prosthetic femoral head is the furthest point on the component from a geometric center of a femoral head rim of the head. The polar location, pole, or apex of a prosthetic mobile insert is the furthest point on the component from a geometric center of a mobile insert rim of the insert. Typically, the polar location, pole, or apex of a femoral head or mobile insert is coincident with a femoral head or insert axis.

The term "shape memory" is used herein to refer to a material that can change its density, volume, geometry, and/or other physical or chemical properties under action of an external stimulus that can be imposed artificially or that can occur naturally.

The term "margin" as used herein refers to an edge or border of something.

The term "frictional torque" as used herein refers to torque caused by a frictional force that occurs when two objects in contact move relative to each other, such as when two surfaces articulate relative to each other. In a hip implant, frictional torque is produced at the articulation between a femoral head and an acetabular liner, at the articulation between a femoral head and a mobile insert, at the articulation between a mobile insert and an acetabular shell, at the articulation between a mobile insert and native acetabulum, etc.

Overview

Various embodiments of femoral heads, acetabular components, mobile inserts, and modular junctions for orthopedic implants, e.g., hip replacement implants, are provided. Additionally, various embodiments of methods of using femoral heads, acetabular components, mobile inserts, and modular junctions for orthopedic implants, e.g., hip replacement implants, are provided. The femoral heads, mobile inserts, and acetabular components described herein can be configured to alleviate soft tissue impingement, reduce implant wear, and/or reduce frictional torque. Various femoral head embodiments are described herein in relation to large diameter femoral heads, e.g., having a diameter greater than about 32 mm. However, the femoral heads designs described herein can be applicable to prosthetic femoral heads of all diameters, including implants that only replace the native femoral head and not the native acetabulum (e.g., hemi-arthroplasty implants). Various mobile inserts embodiments are described in relation to dual mobility implants. However, these mobile insert designs are also applicable to any hip prosthesis that employs a mobile acetabular component. The modular junctions described herein can be configured to minimize the incidence of loosening and micromotion that can occur at these junctions. Various embodiments are described herein in relation to a modular femoral head-neck junction of a hip implant. However, such modular junctions can be employed at any location within any type of orthopedic implant where it is desired to join two components.

Prosthesis Materials and Construction

The implants described herein can be constructed in various manners and can be made from one or more materials. Implant components (e.g., acetabular shell, acetabular liner, mobile insert, femoral head, femoral stem, femoral neck, and modular junction) can be machined, cast, forged, molded, or otherwise constructed out of a medical grade, physiologically acceptable material such as a cobalt chromium alloy, a titanium alloy, stainless steel, ceramic, etc. Other examples of materials for the implants include polyolefins, polyethylene, ultra-high molecular weight polyethylene, medium-density polyethylene, high-density polyethylene, medium-density polyethylene, highly cross-linked ultra-high molecular weight polyethylene (UHMWPE), etc. Exemplary embodiments of UHMWPE prosthesis materials and manufacturing processes are described in U.S. Pat. No. 5,879,400 filed Feb. 13, 1996 entitled "Melt-Irradiated Ultra High Molecular Weight Polyethylene Prosthetic Devices;" US. Pat. Pub. No. 2009/0105364 filed Dec. 12, 2008, entitled "Radiation And Melt Treated Ultra High Molecular Weight Polyethylene Prosthetic Devices;" U.S. Pat. No. 7,906,064 filed Nov. 29, 2006 entitled "Methods For Making Oxidation Resistant Polymeric Material;" U.S. Pat. No. 8,293,811 filed Apr. 5, 2010 entitled "Methods For Making Oxidation-Resistant Cross-Linked Polymeric Materials;" U.S. Pat. No. 7,166,650 filed Jan. 7, 2005 entitled "High Modulus Crosslinked Polyethylene With Reduced Residual Free Radical Concentration Prepared Below The Melt;" US Pat. Pub. No. 2008/0215142 filed Mar. 3, 2008 entitled "Cross-Linking Of Antioxidant-Containing Polymers;" which are hereby incorporated by reference in their entireties.

Depending on the selection of materials for the different prosthetic components, the prosthesis can involve metal on metal articulations, metal on polyethylene articulations, ceramic on polyethylene articulations, ceramic on ceramic articulations, ceramic on metal articulations, polyethylene on polyethylene articulations, metal on native tissue, polyethylene on native tissue, ceramic on native tissue, etc.

The prosthetic components can be constructed in various sizes to fit a range of typical patients, or the components can be custom-designed for a specific patient based on data provided by a surgeon, e.g., after physical and radiography examination of the specific patient. Additionally, in some implants, such as those involving ceramic on ceramic articulations or metal on metal articulations, the acetabular shell can directly articulate with the femoral head without an intermediate acetabular liner. In other implants, the acetabular liner and acetabular shell can be a single monoblock component. Similarly, in some implants the femoral head and femoral stem can be distinct components. In other implants, the femoral head and femoral stem can be a single monoblock component.

The femoral head or mobile insert can have a mushroom shape as shown in various embodiments discussed further below, e.g., embodiments illustrated in FIGS. 10, 11B, 12A, 12B, 13B, 14D, and 15-17B. The femoral head or mobile insert can also be spherical, semi-spherical, or ball-like, and the femoral head and the mobile insert can together have a mushroom shape, as shown in various embodiments discussed further below, e.g., embodiments illustrated in FIGS. 12A-12C and 20A-21B.

Preventing Soft Tissue Impingement

Figure 1:
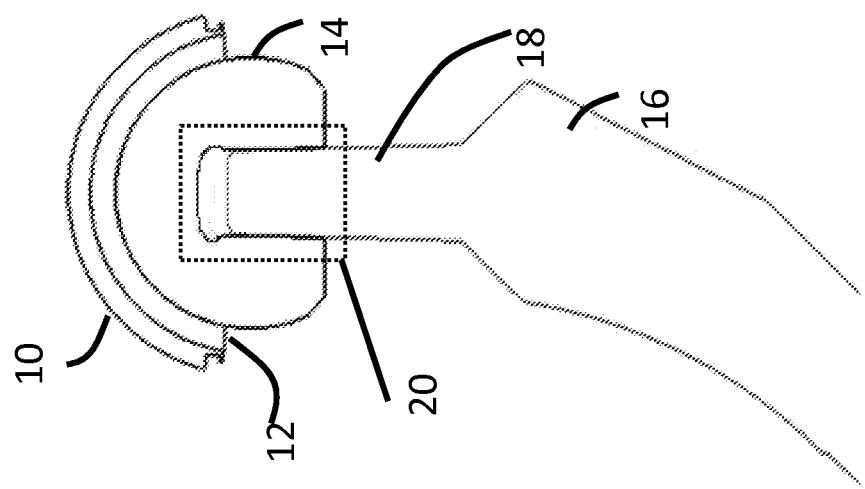
FIG. 1 (PRIOR ART) is a schematic view of a conventional fixed bearing hip arthroplasty implant.
Figure 2B:
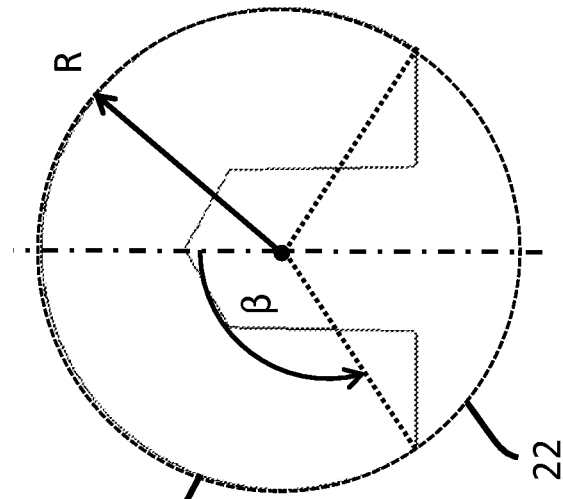
FIG. 2B (PRIOR ART) is a schematic view of another conventional femoral head.
Figure 2A:
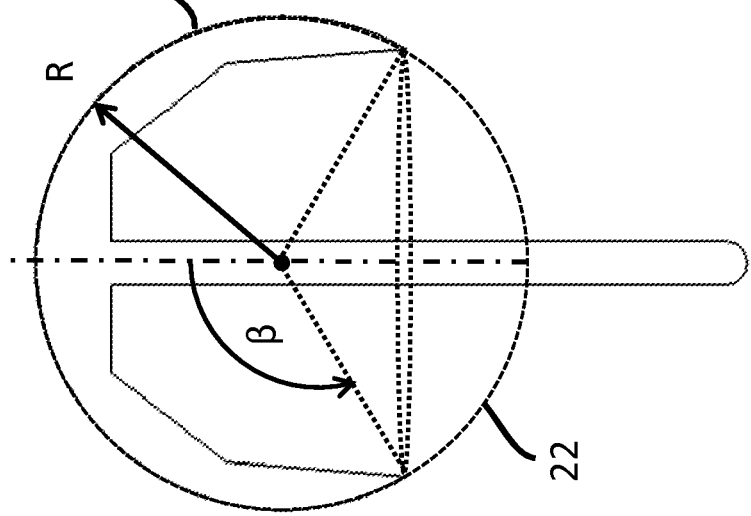
FIG. 2A (PRIOR ART) is a schematic view of a conventional femoral head.
Figure 4:
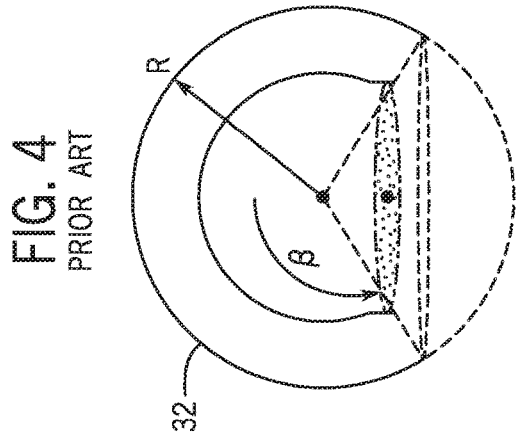
FIG. 4 (PRIOR ART) is a schematic view of a mobile insert of a conventional dual mobility implant.
Figure 5A:
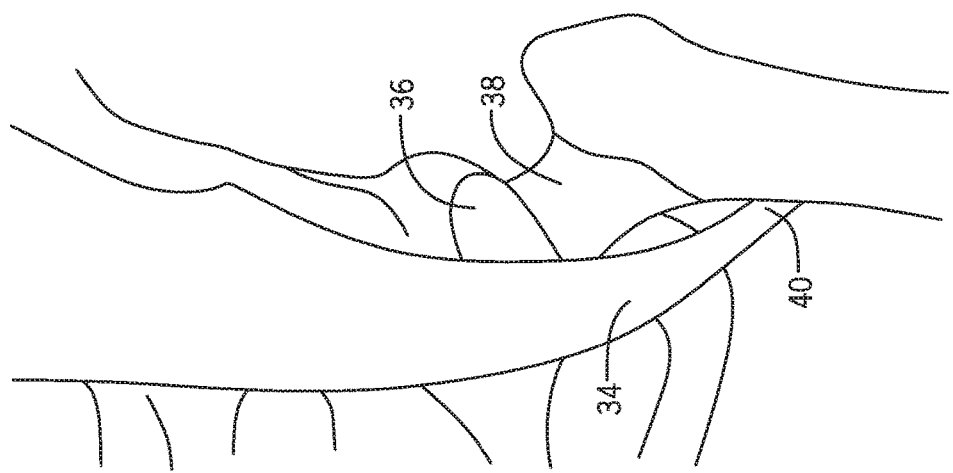
FIG. 5A (PRIOR ART) is a perspective view of native hip anatomy.
Figure 6A:
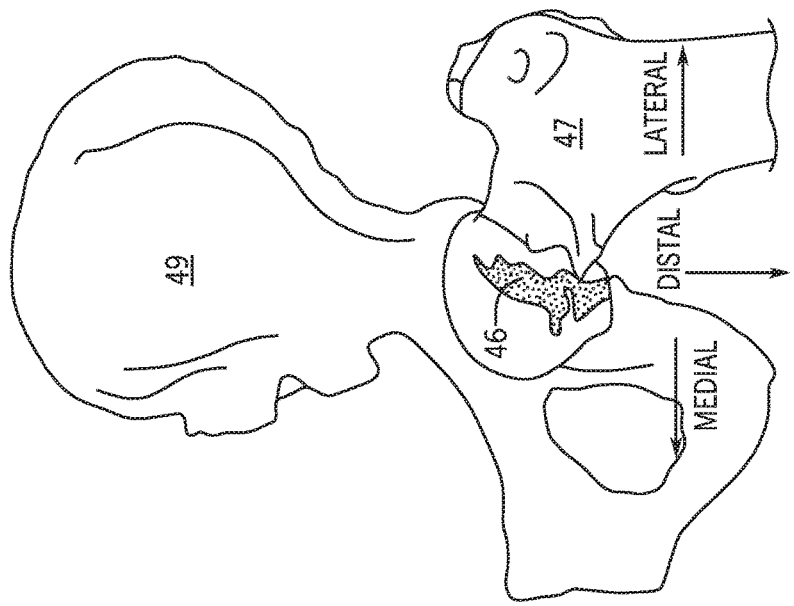
FIG. 6A (PRIOR ART) is a perspective view of a conventional femoral head mounted on a computer tomography (CT) bone model of a hip.
Figure 8A:
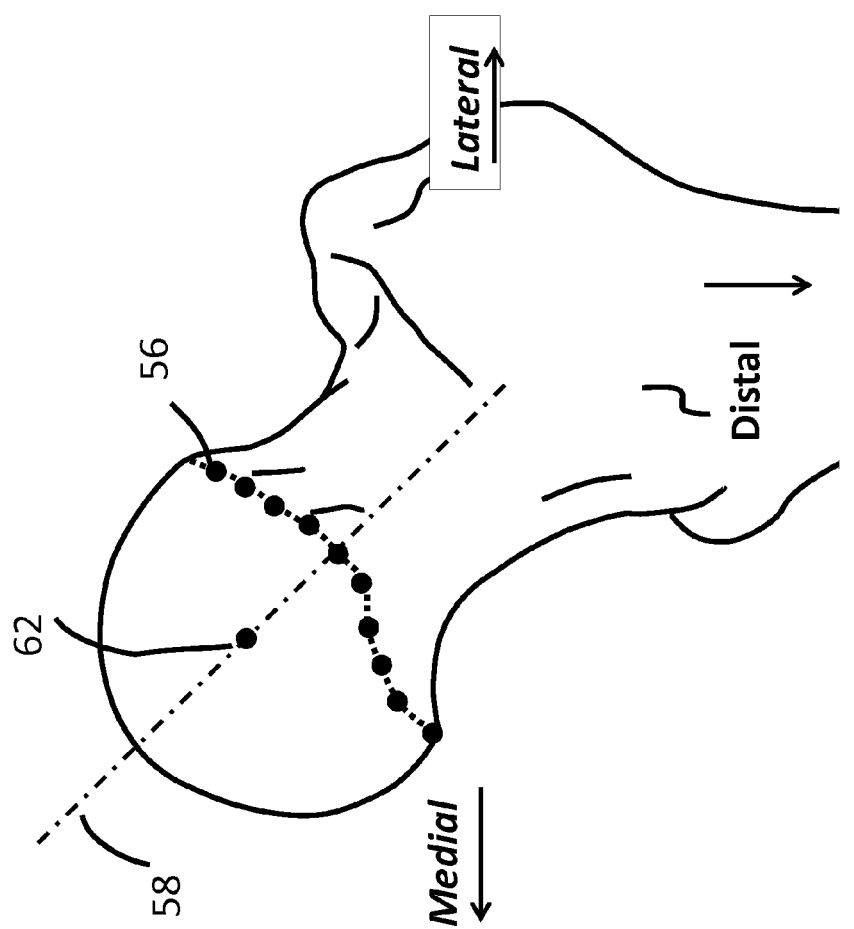
FIG. 8A (PRIOR ART) is a schematic, coronal plane view of a native femoral head.
Figure 8B:
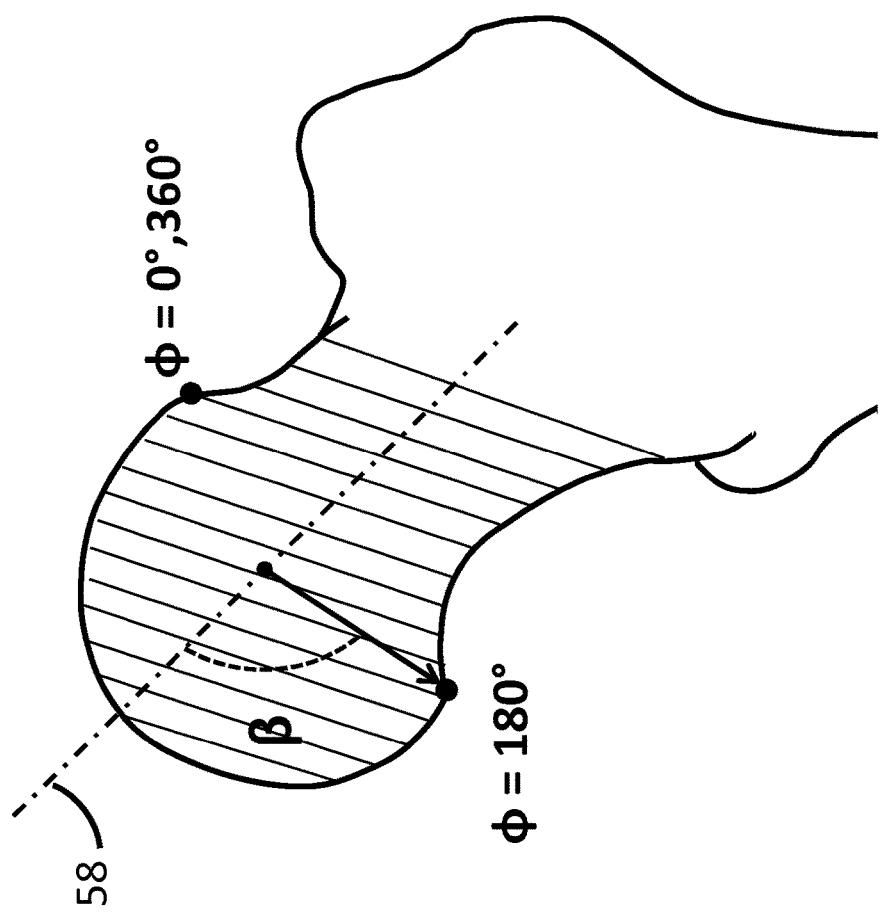
FIG. 8B (PRIOR ART) is a schematic, cross-sectional view of the native femoral head of FIG. 8A showing measurement variables characterizing the angular extent of the articular surface.
Figures 8C, 8D:
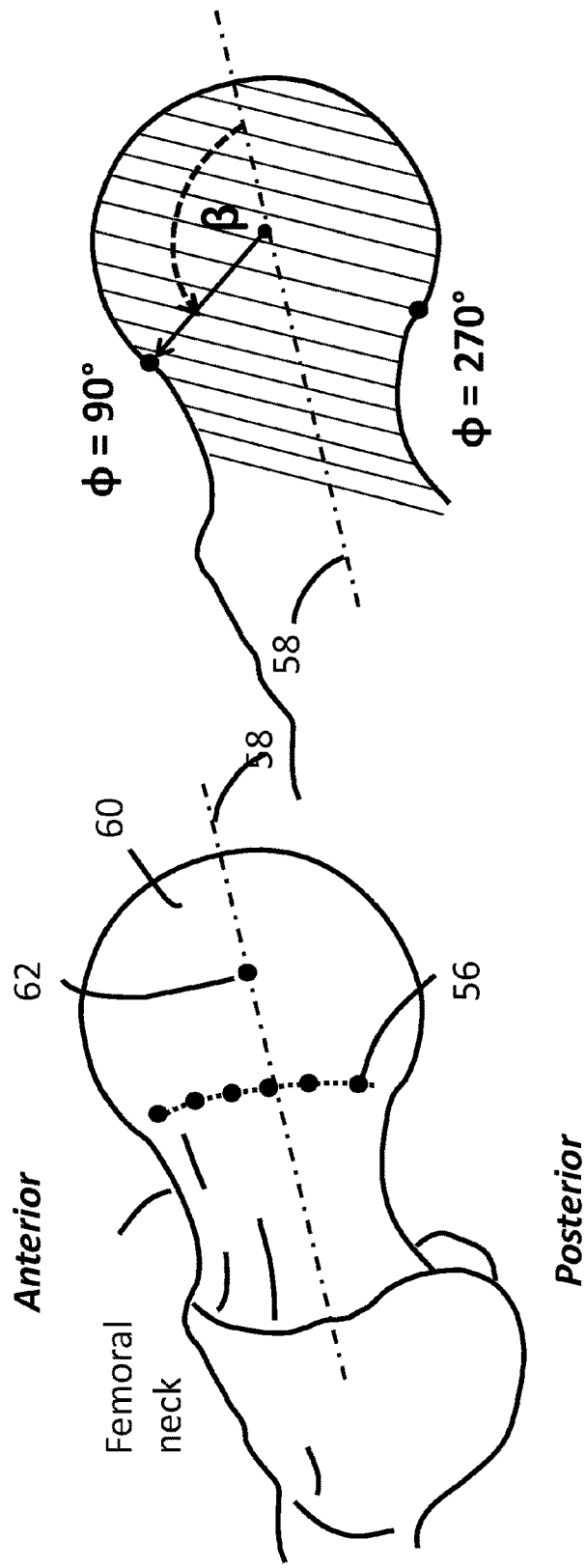
FIG. 8C (PRIOR ART) is a schematic, transverse plane view of the native femoral head of FIG. 8A.
FIG. 8D (PRIOR ART) is a schematic, cross-sectional view of the native femoral head of FIG. 8C showing measurement variables characterizing the angular extent of the articular surface.

Conventional large diameter femoral heads and mobile inserts, such as those shown in FIGS. 2A, 2B, and 4 have a spherical outer articular surface that is axisymmetric about a femoral head or mobile insert axis, and composed of a single radius R that has an angular extent, $\beta$, of about 120°. In contrast, the articular surface of the native femoral head is not axisymmetric about the femoral head axis. Additionally, some portions of the native femoral head articular surface have an angular extent that is significantly less than that of the conventional femoral heads and mobile inserts. As shown in FIGS. 8A-8D, an angular extent $\beta$ (FIGS. 8B and 8D) of a native femoral head articular surface 56 of a femoral head 60 can be measured at different locations around a femoral head axis 58 characterized by an azimuth angle $\phi$. FIGS. 8A and 8B show a coronal plane view of the native femoral head 60 and a coronal cross-section through a femoral head center 62. A proximal-lateral margin or edge of the femoral head articular surface 56 corresponds to $\phi=0°$ and 360°, and a distal-medial margin or edge corresponds to $\phi=180°$. FIGS. 8C and 8D show a transverse view of the native femoral head 56 and a transverse cross-section through the geometric center 62 of the femoral head 56. A anterior most margin or edge of the femoral head articular surface 56 corresponds to $\phi=90°$, and a posterior most margin or edge corresponds to $\phi=270°$. When the hip joint is seen in a frontal or coronal view with the leg straight relative to the pelvis, the medial most margin of the femoral head articular surface is located distal to the lateral most margin, as shown in FIGS. 5A and 6A.

Figure 6B:
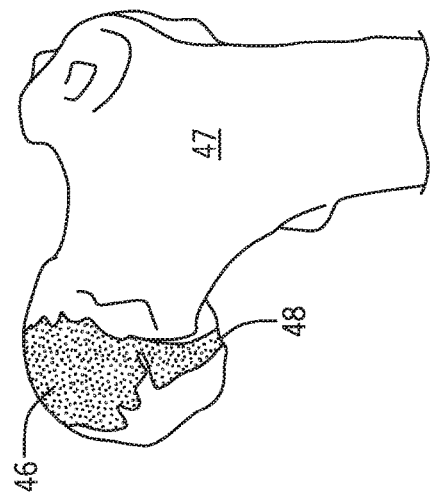
FIG. 6B (PRIOR ART) is another perspective view of the conventional femoral head and femur bone model of FIG. 6A.
Figure 9:
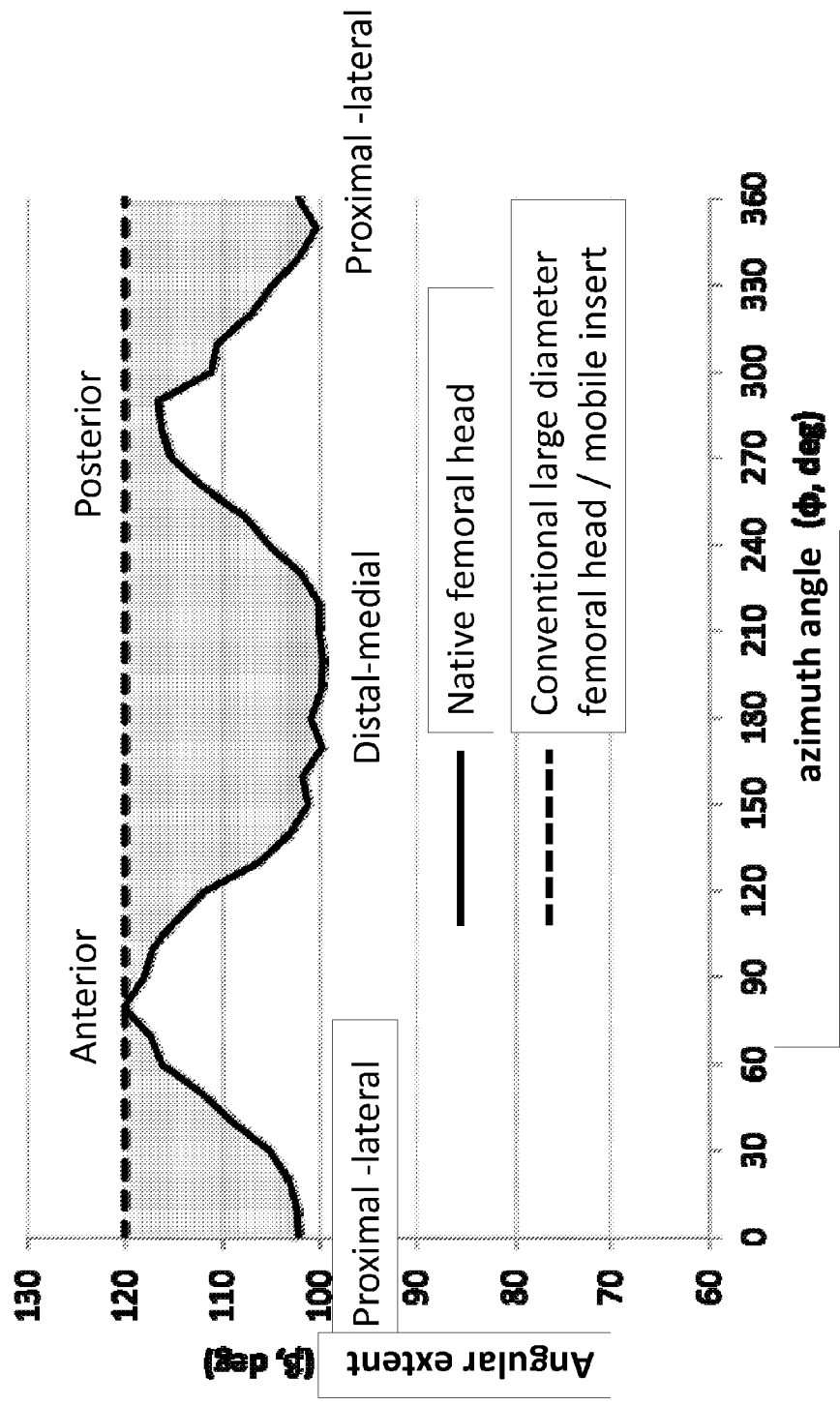
FIG. 9 (PRIOR ART) is a graph of angular extent of native femoral head and a prosthetic conventional femoral head or mobile insert versus azimuth angle measured about the native femoral head axis.

FIG. 9 shows a plot of the angular extent of the native femoral head articular surface 56 in solid black line and an outer articular surface of a conventional large diameter femoral head prosthesis or mobile insert in dashed black lines, as a function of the azimuth angle $\phi$ around the native femoral head axis 62. (Data in FIG. 9 is adapted from Cobb et. al "Why Large-Head Metal-On-Metal Hip Replacements Are Painful: The Anatomical Basis Of Psoas Impingement On The Femoral Head-Neck Junction," *J Bone Joint Surg Br.* 2011 July, 93(7):881-5.) Herein, the prosthetic femoral head or mobile insert axis 58 is parallel to the native femoral head (or native femoral neck axis). As shown in FIG. 9, the angular extent of the native femoral head articular surface is not constant. At the anterior most and the posterior most margins, the angular extent $\beta$ of the native femoral articular surface is about 120°. However, at the proximal-lateral and distal-medial margins, the angular extent of the native femoral articular surface is only about 100°. In contrast, conventional large diameter femoral heads and mobile inserts have an articular surface 56 composed of a single fixed radius that matches the native femoral head radius, and a constant angular extent $\beta$ of about 120° around the femoral head or mobile insert axis 58. The single radius design of the prosthetic components, combined with the constant angular extent, leads to implant overhang over the shaded region shown in FIG. 9 (also see FIGS. 6A and 6B). The anterior-medial (or anterior-distal) overhang in particular can impinge on the iliopsoas muscle or tendon under combined hip flexion and abduction or combined hip flexion and external rotation. These overhanging portions of the implant can also impinge the iliopsoas during hip extension, as the iliopsoas wraps around the distal portion of the native femoral head before inserting onto the lesser trochanter of the femoral bone (see FIG. 5A). This problem is further confounded by any errors in implant sizing, implant positioning variations, and limitations in range of available implant sizes. For example, large metal-on-metal total hip implants can fail due to anterior iliopsoas and capsular impingement from large diameter femoral head prosthesis. (See Browne et al. "Failure Of Larger-Diameter Metal-On-Metal Total Hip Arthroplasty Resulting From Anterior Iliopsoas Impingement," *J Arthroplasty* 2011 September, 26(6):978.e5-8.)

Various embodiments of prostheses disclosed herein can address the above issues. In some embodiments, a portion of an outer surface of a prosthetic femoral head or a mobile insert is contoured to move the surface inwards or towards the interior, such as closer to a center of an overall spherical geometry of the surface. In other embodiments, a portion of an outer surface of a femoral head or mobile insert is trimmed or carved to remove material from regions of potential impingement with native soft-tissue. In other embodiments, features on the mobile insert and/or acetabular shell help guide the relative movement of components to minimize potential impingement with native soft-tissue.

Axisymmetric Embodiments

In an axisymmetric embodiment of an orthopedic implant, an outer surface of a femoral head or mobile insert can be contoured to avoid significant overhang over the native articular surface. In other words, a portion of the outer surface of the prosthetic femoral head or mobile insert can be contoured to move the surface inwards relative to an overall spherical geometry of the implant.

Figure 10:
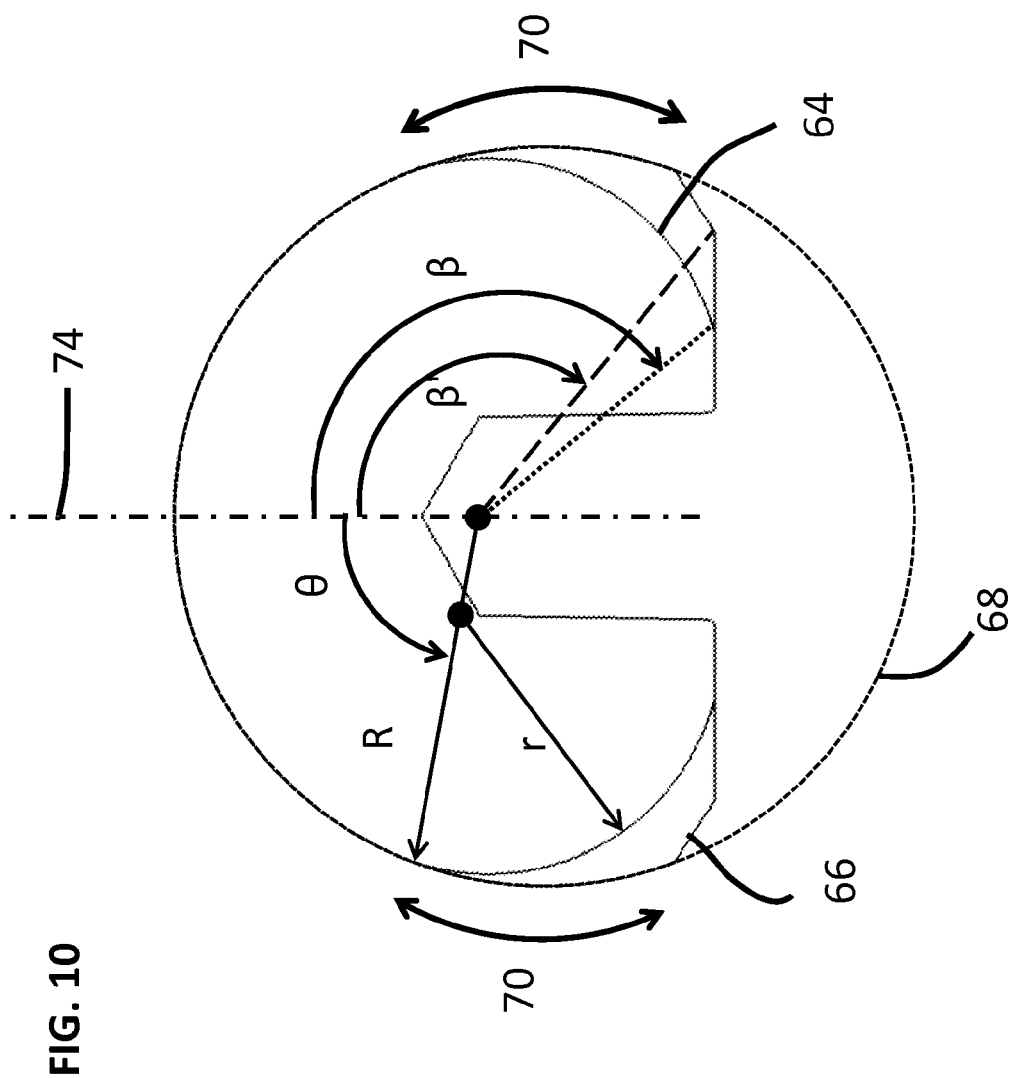
FIG. 10 is a schematic view of a conventional femoral head superimposed on an embodiment of a femoral head showing a first set of measurement variables.
Figure 11B:
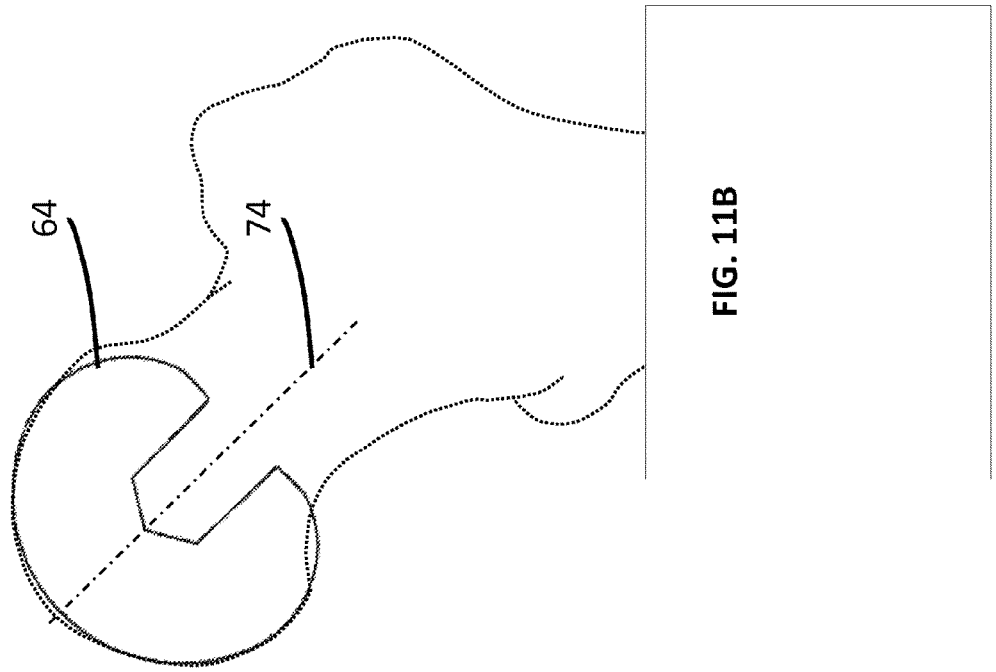
FIG. 11B is a schematic view of the femoral head embodiment of FIG. 10 mounted on the native femoral bone of FIG. 11A.
Figure 11A:
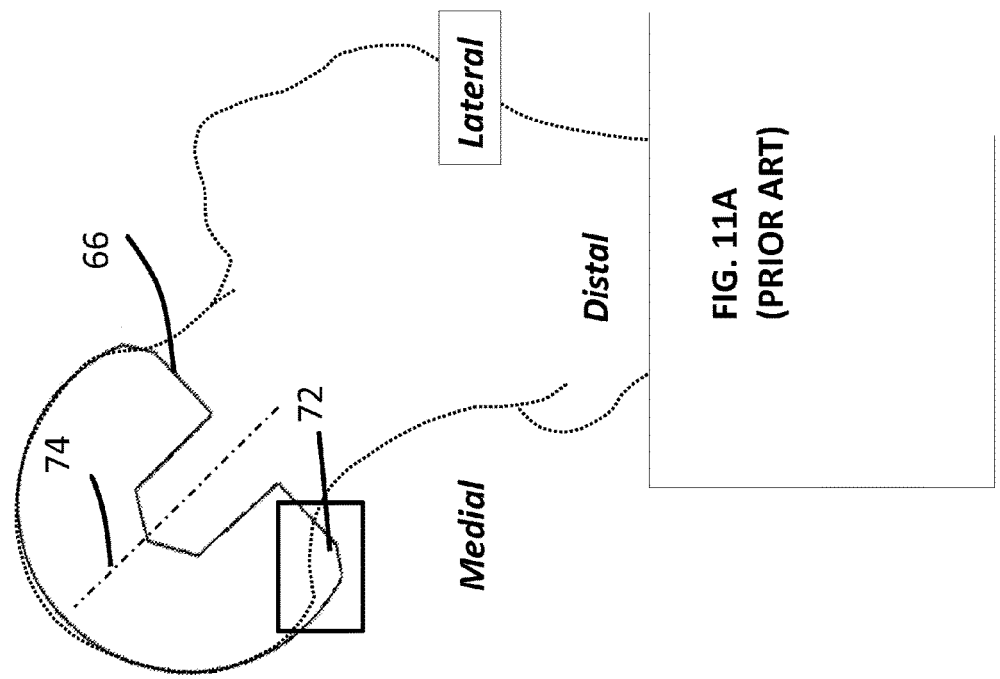
FIG. 11A (PRIOR ART) is a schematic view of the conventional femoral head of FIG. 10 mounted on native femoral bone.

In some embodiments, such axisymmetric contoured articular surfaces can be composed of multiple radii of curvature. As in an exemplary embodiment illustrated in FIG. 10, a femoral head articular surface of a femoral head 64 can be part spherical so as to have an overall spherical geometry 68 with a radius R matching an overall spherical radius of a native femoral head of equivalent size, and with a smaller radius r that forms a peripheral portion of the femoral head 64. FIG. 10 also shows a conventional femoral head 66 to facilitate comparison between the axisymmetric femoral head and the conventional femoral head. The overall spherical radius of the axisymmetric femoral head 64 and the conventional femoral head 66 are identical, and equal to R. As seen in the cross-sectional view of FIG. 10, the contoured and conventional femoral heads 64, 66 have identical geometries until a theta angle θ, measured with respect to a femoral head axis 74. Thereafter, the articular surface radius is reduced for the contoured head 64, and this smaller radius portion 70 extends to the peripheral margin, rim, or edge of the implant. An overall angular extent of the femoral head articular surface β is approximately equal to an overall angular extent of the femoral head articular surface β' of a conventional implant. The contoured geometry minimizes overhang of the femoral head 64 beyond the native articular surface, and thereby potential for soft-tissue impingement, as shown in FIG. 11B. For comparison with FIG. 11B, FIG. 11A illustrates overhang 72 of the conventional femoral head 66 in relation to the native femoral head geometry.

Figure 12C:
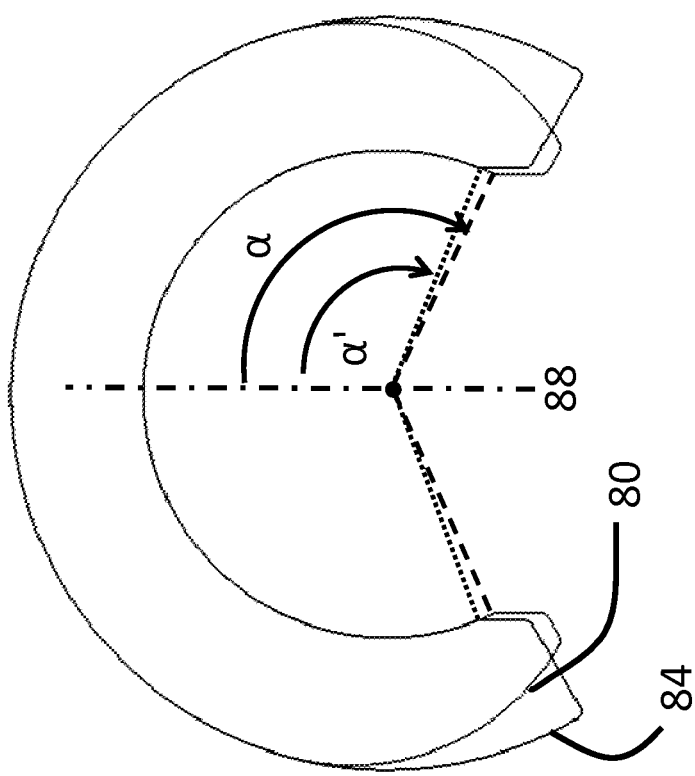
FIG. 12C is a schematic view of the conventional mobile insert of FIG. 12A superimposed on the mobile insert of FIG. 12A showing a third set of measurement variables.
Figure 13A:
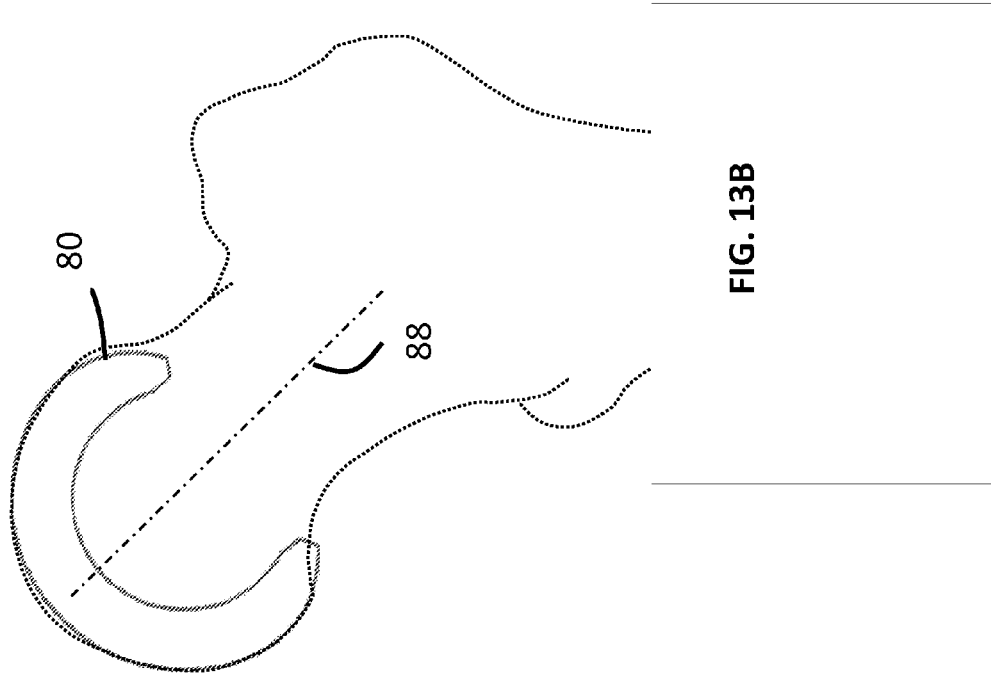
FIG. 13A (PRIOR ART) is a schematic view of the conventional mobile insert of FIGS. 12A-12C mounted on native femoral bone.
Figure 13B:
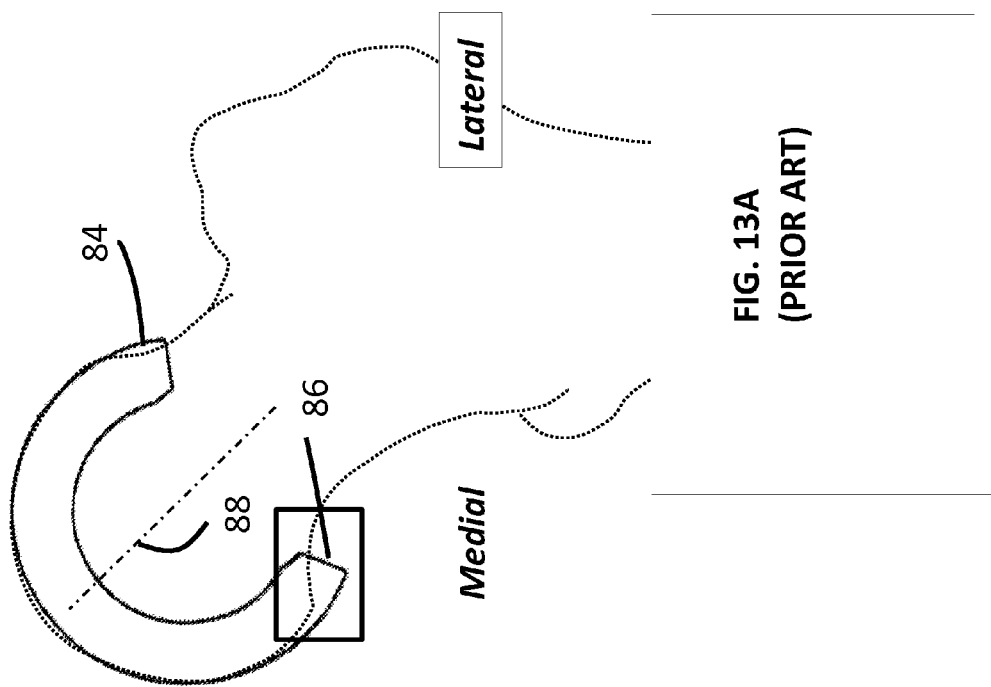
FIG. 13B is a schematic view of the mobile insert of FIGS. 12A-12C mounted on the native femoral bone of FIG. 13A.
Figure 14D:
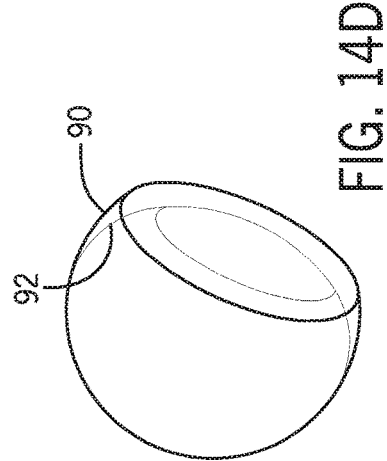
FIG. 14D is a perspective view of the femoral head of FIG. 14C superimposed on the conventional femoral head of FIG. 14A.
Figure 14E:
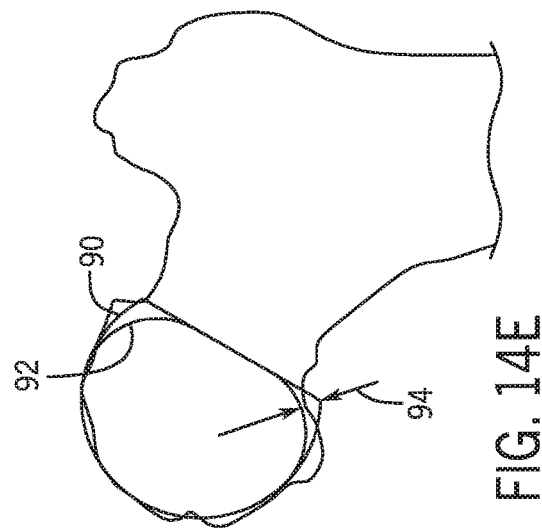
FIG. 14E is a schematic view of the femoral head of FIG. 14C and the conventional femoral head of FIG. 14A mounted on the CT based bone model of FIG. 14B including a coronal cross-section of a femur.
Figure 14B:
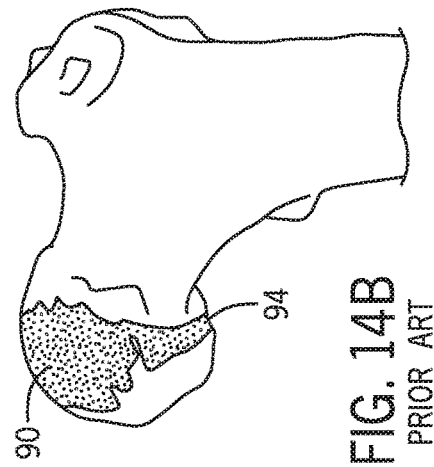
FIG. 14B (PRIOR ART) is another perspective view of the conventional femoral head of FIG. 14A mounted on the CT based bone model.
Figure 14C:
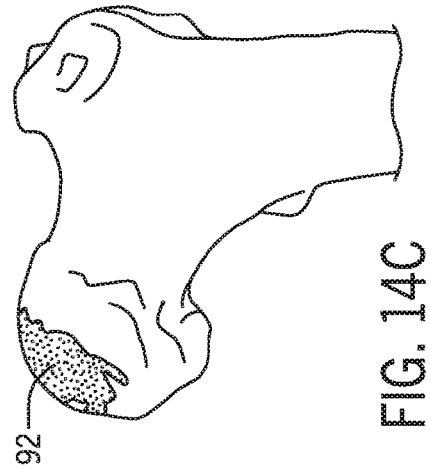
FIG. 14C is a perspective view of an embodiment of a femoral head mounted on the CT based bone model of FIG. 14B.

As in an exemplary embodiment illustrated in FIGS. 12A-12C, an articular surface of a mobile insert 80 can be part spherical with a radius R approximately matching an overall spherical geometry 82 of radius R of a native femoral head of equivalent size, and with a smaller radius r that forms a peripheral portion of the mobile insert 80. FIGS. 12A-12C also show a conventional mobile insert 84 to facilitate comparison between the axisymmetric mobile insert 80 and the conventional mobile insert 84. As seen in the cross-sectional view of FIG. 12B, the contoured and conventional mobile inserts 80, 84 have identical geometries until a theta angle θ, measured with respect to a mobile insert axis 88. Thereafter, the articular surface radius is reduced for the contoured mobile insert 80, and this smaller radius portion extends to a peripheral margin or rim of the implant. An overall angular extent β of the mobile insert's articular surface is approximately equal to the conventional implant's overall angular extent β'. The contoured surface geometry minimizes overhang of the insert 80 beyond the native articular surface, and thereby potential for soft-tissue impingement, as shown in FIG. 13B. For comparison with FIG. 13B, FIG. 13A illustrates overhang 86 of the conventional insert 84 in relation to the native femoral head geometry.

FIGS. 14A-14E variously show a conventional femoral head/mobile insert 90, and an exemplary embodiment of a femoral head/mobile insert 92 disclosed herein mounted on a computer tomography (CT) based bone model of a cadaver specimen. As seen in FIGS. 14A-14E, while the conventional femoral head or insert (FIGS. 14A, 14B, 14D, and 14E) overhangs 94 the native femoral head articular surface in the anterior-medial (or anterior-distal) and posterior-medial (or posterior-distal) regions, the femoral head and mobile insert 92 disclosed herein (FIGS. 14C, 14D, and 14E) are fully contained within the articular surface of the native femoral head. The overhang 94 of the conventional femoral head/mobile insert 90 can be 3 mm, as in FIG. 14E.

Figure 15:
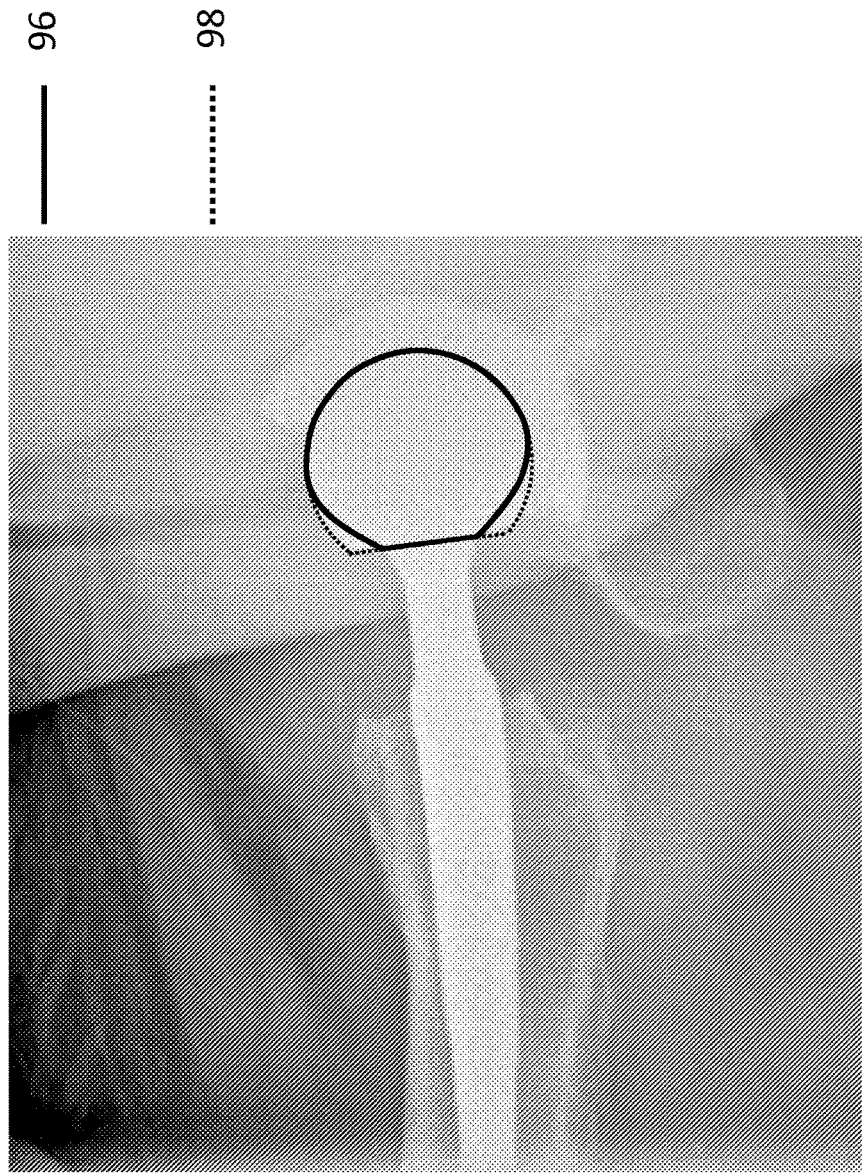
FIG. 15 is a perspective view of an embodiment of a femoral head superimposed on a conventional femoral head shown in a lateral radiograph of a patient.

FIG. 15 illustrates an exemplary embodiment of a femoral head 96 overlaid on a lateral radiograph of a patient with a conventional large diameter femoral prosthesis 98. As seen in FIG. 15, the femoral head 96 has a contoured peripheral articular surface configured to reduce potential for soft-tissue impingement, as opposed to the conventional large diameter femoral prosthesis 98. In this illustrated embodiment, the femoral head 96 has a 36 mm diameter, and the conventional large diameter femoral prosthesis 98 has a 36 mm diameter.

In an exemplary embodiment of a femoral head, an overall spherical radius R of the outer surface of the femoral head (see FIG. 10) is about 18 mm, but the overall spherical radius R can be in a range of about 10 mm to 40 mm, about 15 mm to 35 mm, about 20 mm to 30 mm, etc. A smaller contoured radius r of the femoral head (see FIG. 7) is about 11 mm, but the smaller contoured radius r can be in a range of about 1 mm to 38 mm, about 5 mm to 25 mm, about 10 mm to 20 mm, etc. A ratio of the two radii, r/R, is about 0.6, but can be in a range of about 0.025 to 0.95, about 0.3 to 0.7, about 0.4 to 0.6, etc. A theta angle θ marking transition from the larger radius R to the small radius r (see FIG. 10) is about 75°, but it can be in a range of about 1° to 115°, about 45° to 90°, about 60° to 75°, etc. The overall angular extent of the outer articular surface β (see FIG. 10) is about 125° but can be in a range of about 50° to 150°, about 100° to 130°, about 110° to 120°, etc.

Figure 16C:
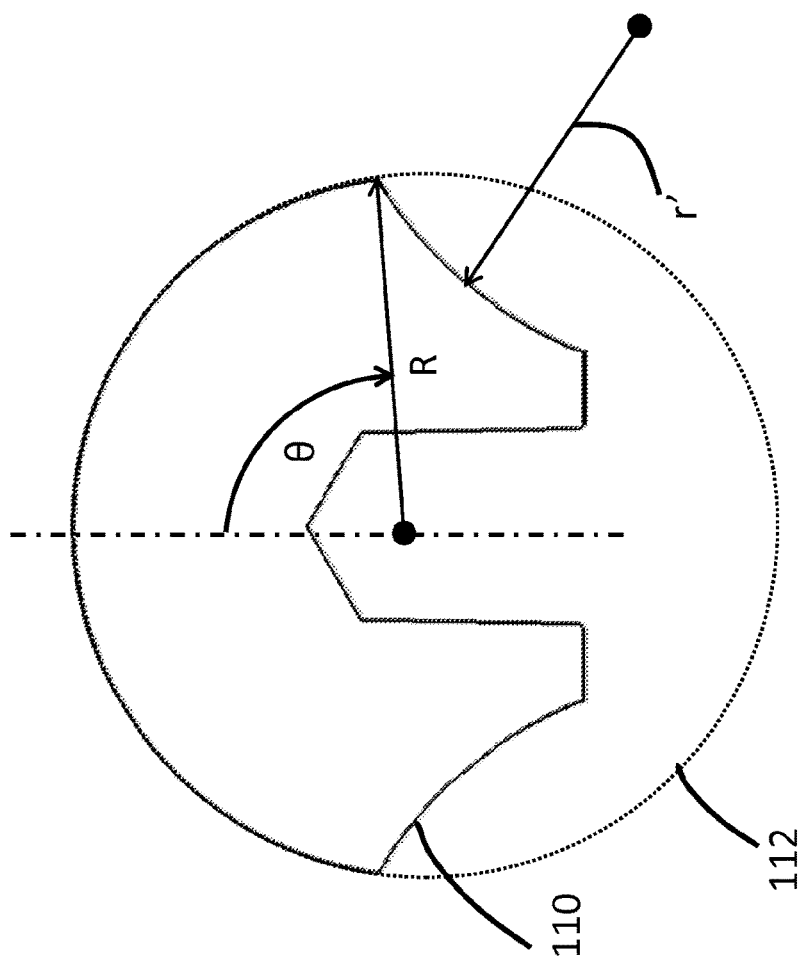
FIG. 16C is a schematic view of an embodiment of a femoral head showing a set of measurement variables, the femoral head having a contoured peripheral surface created using a concave radius.

In the exemplary femoral head embodiment of FIG. 10 and FIG. 11B, the contoured peripheral portion 70 of the femoral head articular surface is composed of a single radius r that is smaller than the overall spherical radius R. In some embodiments, the peripheral portion can be composed of a plurality of radii $r_1$ to $r_n$, where n can be any number greater than or equal to one, such as two radii ($r_1$ and $r_2$), three radii ($r_1$ to $r_3$), four radii ($r_1$ to $r_4$), etc., that are each smaller, larger, or equal to the overall spherical radius R. In some embodiments, the peripheral portion can be continuously varying radii $r_1$ to $r_n$, such as gradually reducing radii, where "n" is an integer greater than one. An arc angle of these smaller radii can be defined by additional parameters $\theta_1$ to $\theta_n$. The radii $r_1$ to $r_n$ can be in a range of about 1 mm to 100 mm, about 10 mm to 40 mm, about 20 mm to 30 mm, etc. The arc angle $\theta_1$ to $\theta_n$ can be in a range of about 1° to 120°, about 20° to 90°, about 45° to 60°, etc. FIG. 16A illustrates an embodiment of a femoral head 100 composed of two radii $r_1$ and $r_2$. FIG. 16A also shows an overall spherical geometry 104 of the femoral head 100, with the sphere having a radius R. In some embodiments, as shown in FIG. 16B, a contoured peripheral portion of a femoral head articular surface of a femoral head 106 can be in the form of a chamfered surface with a chamfer angle γ of about 15°, although the chamfer angle γ can be in a range of about 1° to 80°, about 15° to 60°, about 40° to 50°, etc. FIG. 16B also shows an overall spherical geometry 108 of the femoral head 106, with the sphere having a radius R. In some embodiments, as shown in FIG. 16C, a contoured peripheral portion of a femoral head 110 can be in the form of a concave radius r' of about 45 mm, although the concave radius r' can be in a range of about 1 mm to 100 mm, about 15 mm to 80 mm, about 45 mm to 60 mm, etc. FIG. 16C also shows an overall spherical geometry 112 of the femoral head 108, with the sphere having a radius R.

Figure 17B:
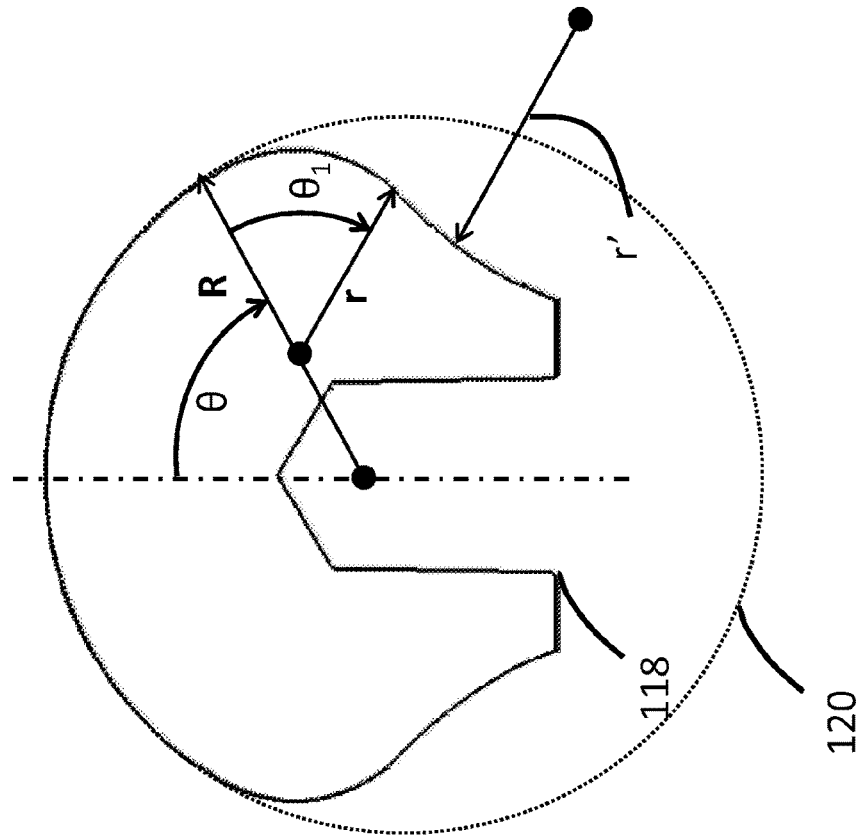
FIG. 17B is a schematic view of an embodiment of a femoral head showing a set of measurement variables, the femoral head having a contoured peripheral surface created using a combination of multiple convex radii and a concave radius.
Figure 17A:
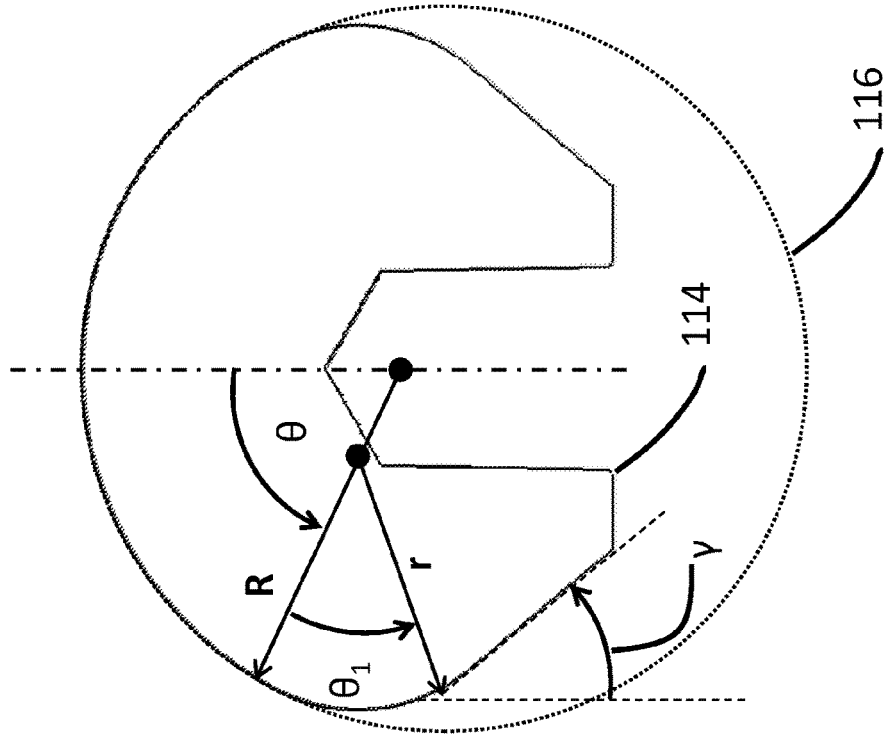
FIG. 17A is a schematic view of an embodiment of a femoral head showing a set of measurement variables, the femoral head having a contoured peripheral surface created using a combination of multiple convex radii and a chamfer.
Figure 17C:
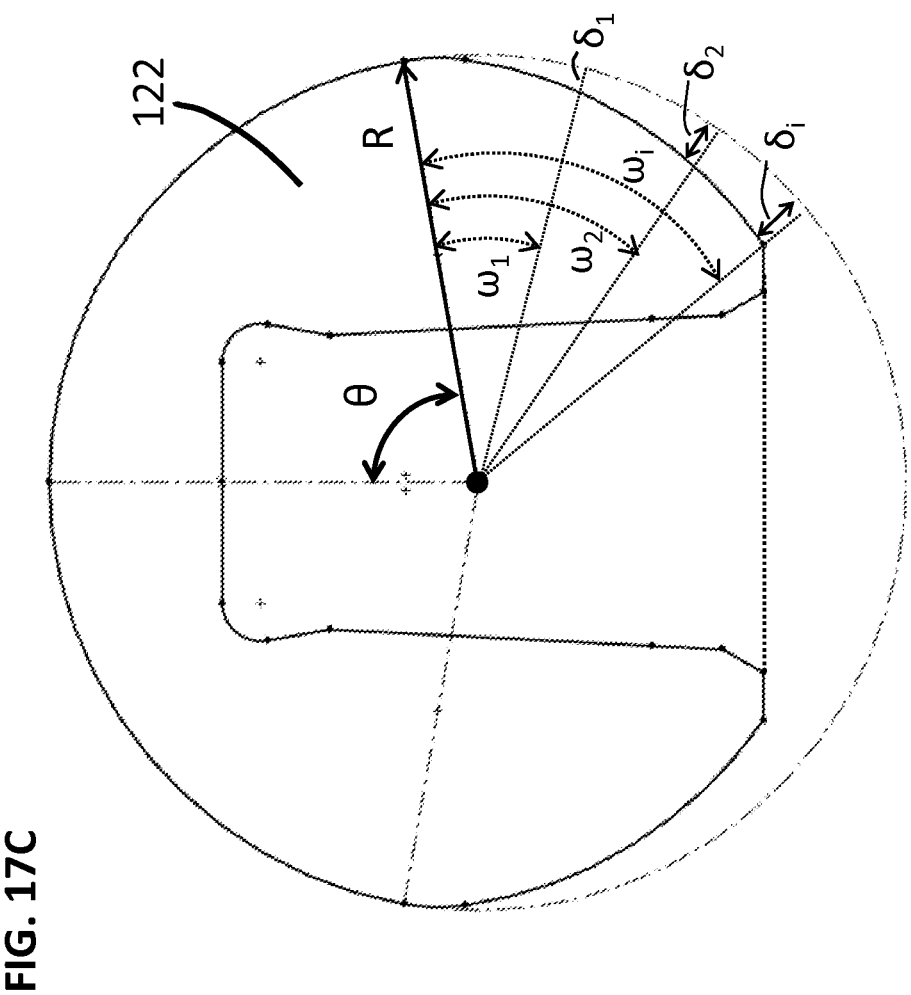
FIG. 17C is a schematic view of an embodiment of a femoral head showing a set of measurement variables characterizing the inward shift of the contoured peripheral surface relative to an overall spherical geometry of the head.

In some embodiments, a combination of convex radii, concave radii, and chamfers can be used to contour an outer articular surface of a femoral head, as shown in embodiments illustrated in FIGS. 17A and 17B. In one embodiment shown in FIG. 17A, a contoured outer articular surface of a femoral head 114 can be composed of a radius R matching an overall spherical radius of the head's overall spherical geometry 116 until a theta angle $\theta$, a smaller convex radius r extending from the theta angle $\theta$ to $\theta_1$, and a chamfer of angle γ extending from $\theta_1$ to a peripheral edge or implant rim. In another embodiment shown in FIG. 17B, a contoured outer articular surface of a femoral head 118 can be composed of a radius R matching an overall spherical radius of the head's overall spherical geometry 120 and extending to a theta angle $\theta$, a smaller convex radius r extending from $\theta$ to $\theta_1$, and a concave radius r' extending from $\theta_1$ to the peripheral edge or implant rim. In another embodiment, contouring of a femoral head's outer articular surface can be achieved with complex spline curves. Thus, a portion of an outer surface of a femoral head can be contoured in any number of ways so as to move the surface inwards relative to an overall spherical geometry of the implant. A maximum inward shift of the contoured surface relative to the overall spherical geometry can be at least about 1 mm. However, the maximum inward shift can be greater than about 1.5 mm, greater than about 2 mm, greater than about 8 mm, etc. For example, in an embodiment of a femoral head 122 shown in FIG. 17C, inward shift increases gradually from $\delta_1$ at an angular location $\omega_1$ to a maximum value of $\delta_i$ at angular location $\omega_i$ corresponding to the femoral head rim, where i is an integer greater than two.

Figure 3B:
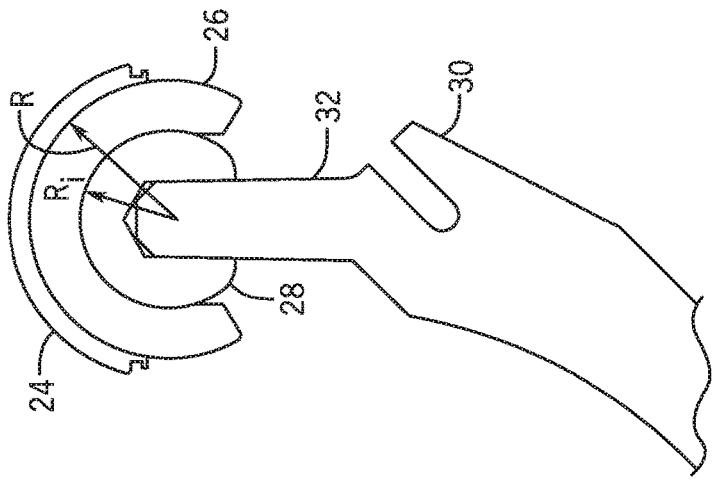
FIG. 3B (PRIOR ART) is a schematic view of the implant of FIG. 3A.
Figure 3A:
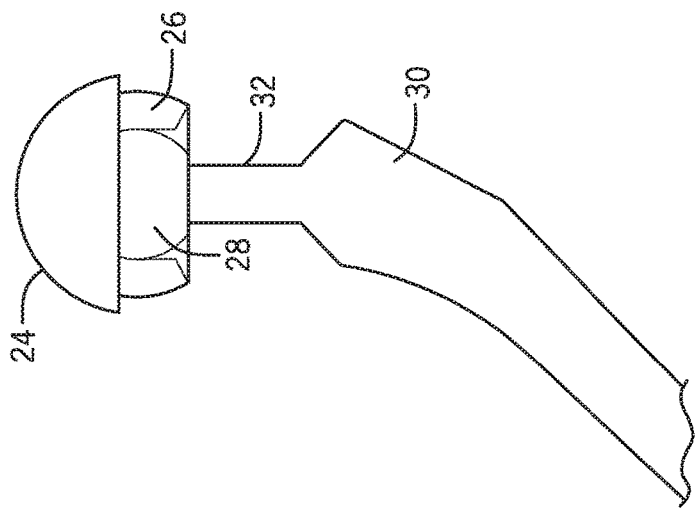
FIG. 3A (PRIOR ART) is a side perspective view of a conventional dual mobility implant.

As shown in FIG. 12A, the contouring of the mobile insert 80 results in a reduction of the insert's thickness by an amount $dt_1$ at a rim of the implant 80 relative to the conventional insert 84. This reduction in thickness can lead to a reduction in the restraint against extraction or removal of the small diameter femoral head captured within the inner articulation (see FIG. 3B). To compensate for this reduction in the restraint against extraction, in an exemplary embodiment, coverage of the small diameter femoral head by the mobile insert 80 can be increased slightly by increasing the angular extent of the inner articular surface from α' to α, as shown in FIG. 12C. This may also be associated with a slight increase in overall angular extent of the outer articular surface from β' to β, as shown in FIG. 12B.

Figure 18B:
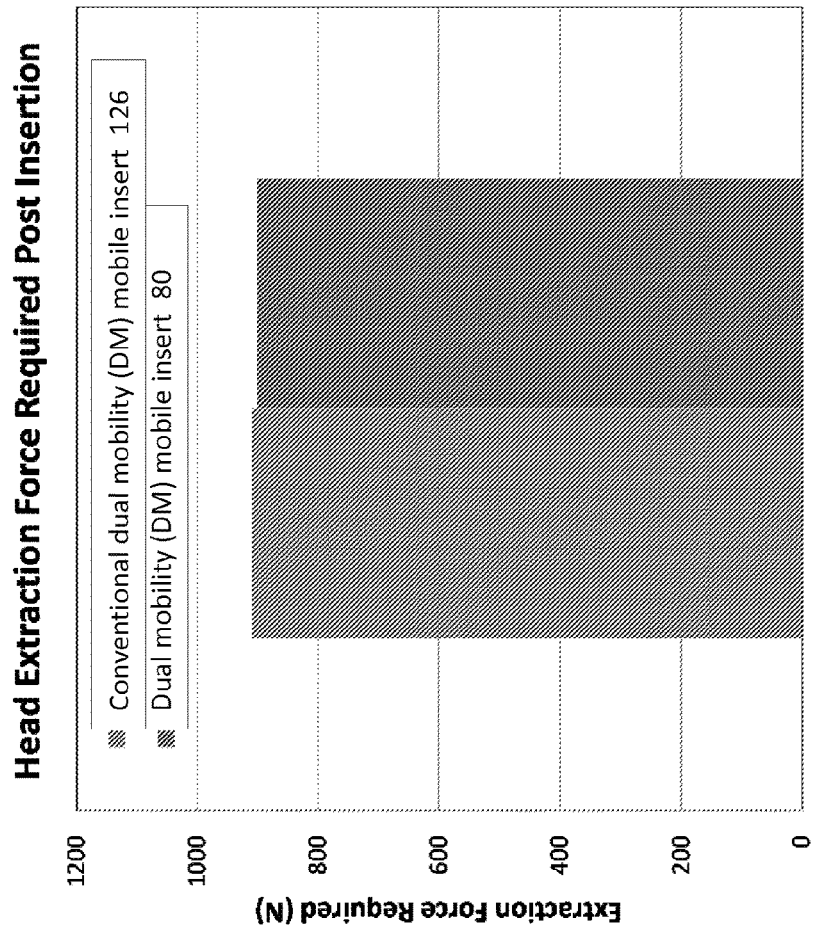
FIG. 18B is a graph showing head extraction force required post insertion for a conventional mobile insert and an embodiment of a mobile insert.
Figure 18A:
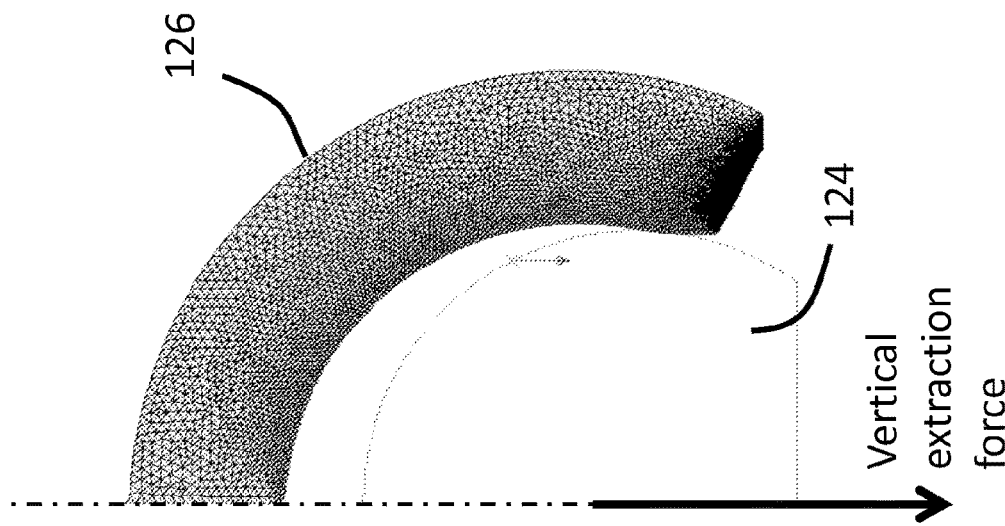
FIG. 18A is a side view of an embodiment of a mobile insert and an embodiment of a femoral head captured within the mobile insert, the femoral head having a vertical extraction force applied thereto to extract the femoral head from the mobile insert.
Figure 19A:
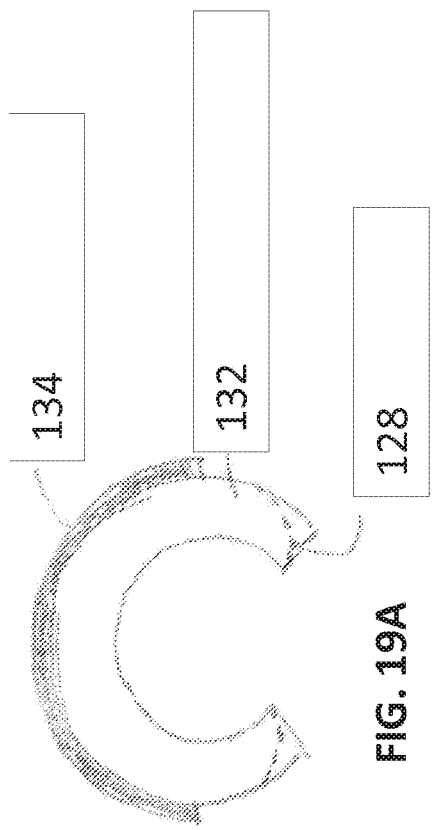
FIG. 19A is a schematic view of an embodiment of a mobile insert superimposed on a conventional mobile insert, the embodiment of a mobile insert with contoured peripheral surface.
Figure 19B:
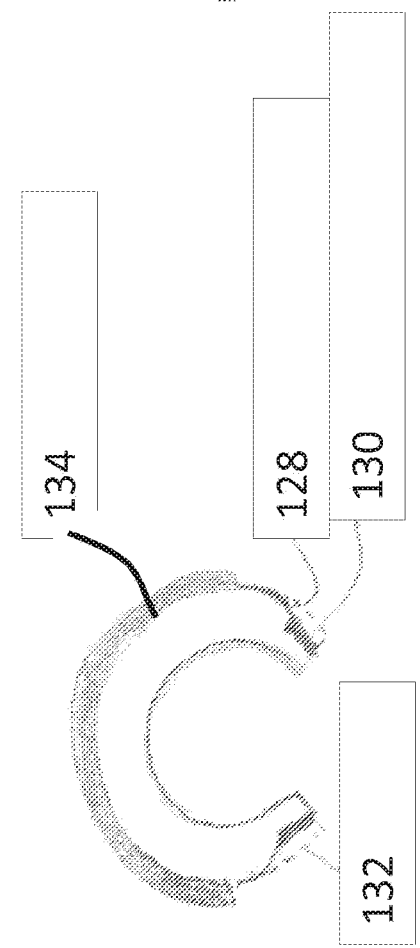
FIG. 19B is a schematic view of an embodiment of a mobile insert superimposed on a conventional mobile insert, the embodiment of a mobile insert with contoured peripheral surface and a supporting metallic ring.
Figure 19C:
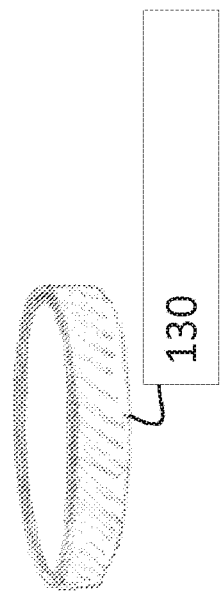
FIG. 19C is a schematic view of the supporting metallic ring of FIG. 19B.

FIGS. 18A and 18B show a comparison of an extraction force required to extract (or remove/pull out) an embodiment of a small diameter femoral head 124 out of a conventional mobile insert 126, and out of the insert 80 of FIGS. 12A-12C and 13B. One cycle of insertion and extraction of the small diameter femoral head out of the dual mobility insert was simulated within a structural analysis software. The design of the mobile insert 80 of FIGS. 12A-12C and 13B was tuned to achieve the same resistance against extraction as the conventional implant 126. As shown in FIG. 18B, the insert 80 (darker grey bar, the bar on the right) and the conventional insert 126 (lighter grey bar, the baron the left) have identical resistance to extraction of a small diameter femoral head from the inner articulation. In other embodiments, as shown in FIGS. 19A-19C, strength of a contoured peripheral portion of a mobile insert 128 can be enhanced by the addition of a supporting ring 130 (shown in FIGS. 19B and 19C) made of a material (such as stainless steel) that is stiffer and stronger than a material (such as polyethylene) forming the insert 128. FIGS. 19A and 19B also show an acetabular shell 134 mated to the mobile insert 128. For comparison purposes, FIGS. 19A and 19B also show a conventional mobile insert 132.

In an exemplary embodiment, an overall spherical radius R of an outer surface of a mobile insert (see FIG. 12A) is about 22 mm, but the overall spherical radius R can be in a range of about 10 mm to 40 mm, about 15 mm to 35 mm, about 20 mm to 30 mm, etc. A smaller contouring radius r of the insert (see FIG. 12A) is about 14 mm in an exemplary embodiment, but it can be in a range of about 1 mm to 38 mm, about 5 mm to 25 mm, about 10 mm to 20 mm, etc. A ratio of the two radii, r/R, is about 0.6 in an exemplary embodiment, but it can be in a range of about 0.025 to 0.95, about 0.3 to 0.7, about 0.4 to 0.6, etc. The theta angle $\theta$ marking transition from the larger radius R to the small radius r (see FIG. 12B) is about 75° in an exemplary embodiment, but it can be in a range of about 2° to 120°, about 45° to 90°, about 60° to 75°, etc. An overall angular extent of the inner articular surface α (see FIG. 12C) is about 116° in an exemplary embodiment, but can be in a range of about 91° to 125°, about 95° to 120°, about 100° to 110° etc. The overall angular extent of the outer articular surface β (see FIG. 12B) is about 125° in an exemplary embodiment, but it can be in a range of about 91° to 150°, about 100° to 130°, about 110° to 120°, etc.

Figure 20B:
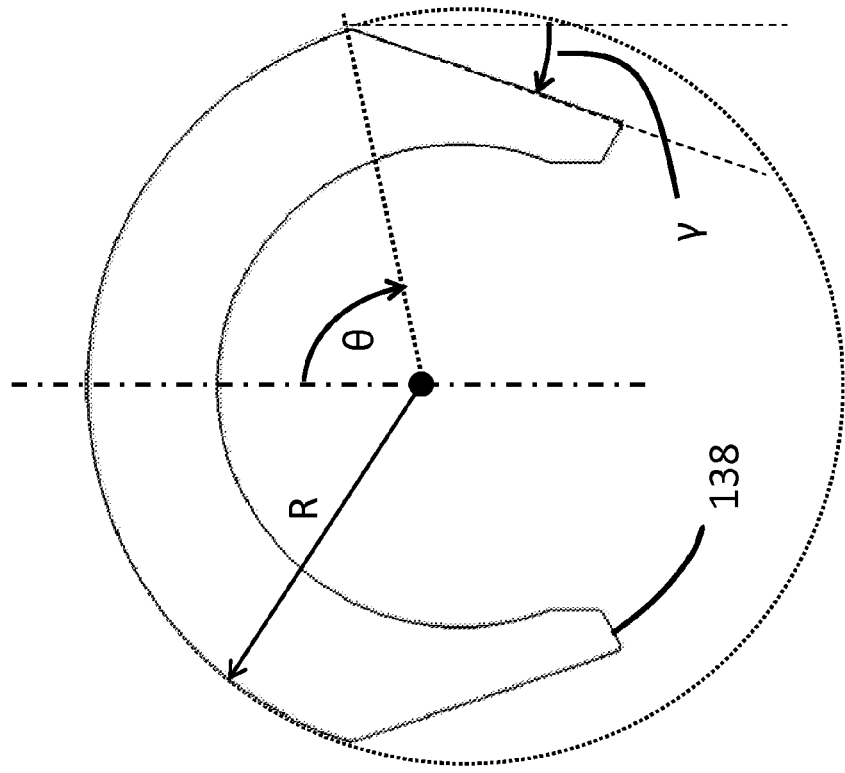
FIG. 20B is a schematic view of an embodiment of a mobile insert showing a set of measurement variables, the mobile insert having a contoured peripheral surface created using a chamfer.
Figure 20A:
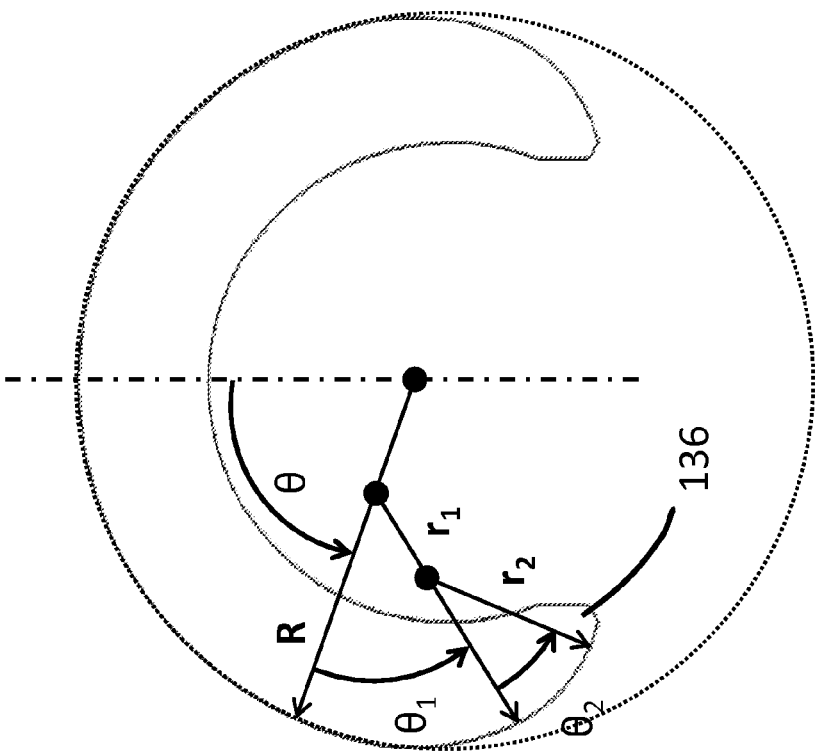
FIG. 20A is a schematic view of an embodiment of a mobile insert showing a set of measurement variables, the mobile insert having a contoured peripheral surface created using multiple convex radii.
Figure 20C:
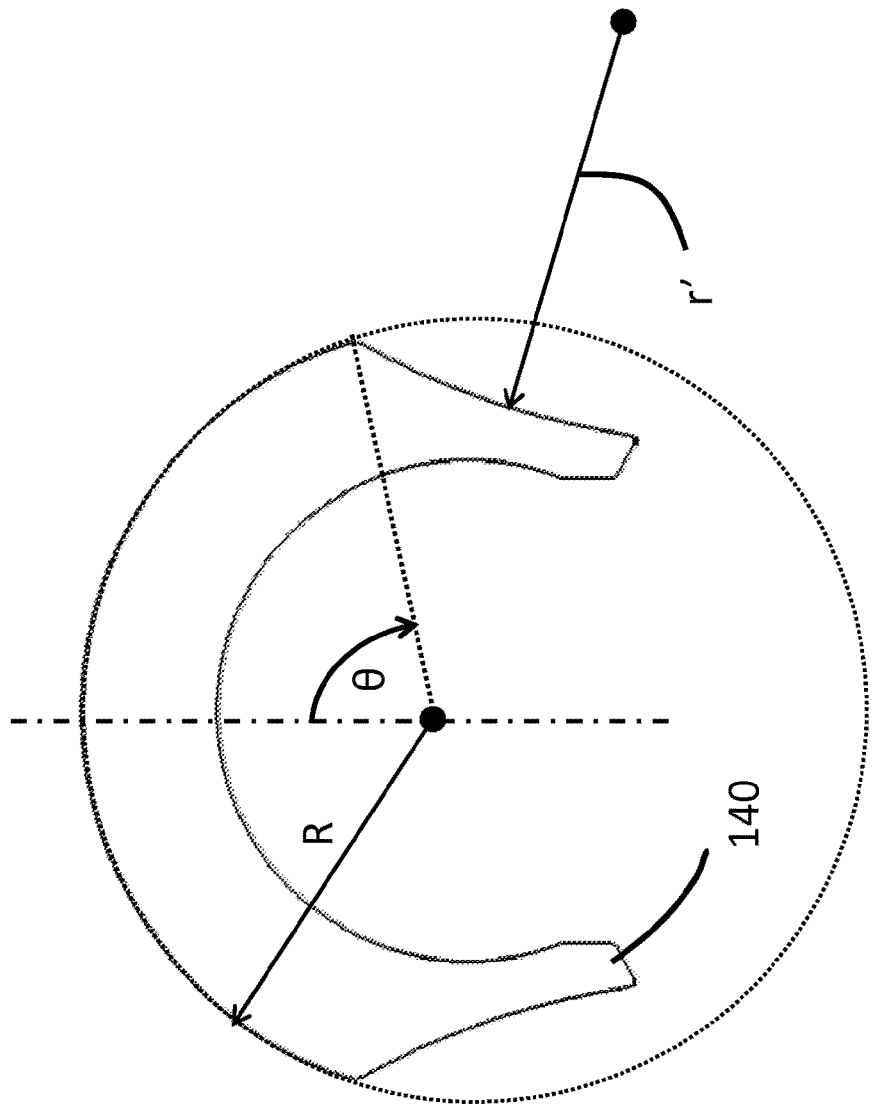
FIG. 20C is a schematic view of an embodiment of a mobile insert showing a set of measurement variables, the mobile insert having a contoured peripheral surface created using a concave radius.

In the exemplary embodiment of FIGS. 12A-12C and 13B, a contoured peripheral portion of the mobile insert 80 is composed of the single radius r that is smaller than the overall spherical radius R. In some embodiments, the peripheral portion can be composed of a plurality of radii $r_1$ to $r_n$, where n can be any number greater than or equal to one, such as two radii ($r_1$ and $r_2$), three radii ($r_1$ to $r_3$), four radii ($r_1$ to $r_4$), etc., that are smaller than the overall spherical radius R. In some embodiments, the peripheral portion can be continuously varying radii $r_1$ to $r_n$, such as gradually reducing radii. An arc angle of these smaller radii can be defined by additional parameters $\theta_1$ to $\theta_n$. The smaller radii $r_1$ to $r_n$ can be in a range of about 1 mm to 38 mm, about 5 mm to 25 mm, about 10 mm to 20 mm, etc. The arc angle $\theta_1$ to $\theta_n$ can be in a range of about 1° to 120°, about 20° to 90°, about 45° to 60°, etc. FIG. 20A illustrates an embodiment of an insert 136 composed of two radii $r_1$ and $r_2$. In some embodiments, such as in an embodiment shown in FIG. 20B, a contoured peripheral portion of a mobile insert 138 can be in the form of a chamfered surface with a chamfer angle γ of about 15°, although the chamfer angle γ can be in a range of about 2° to 80°, about 15° to 60°, about 40° to 50°, etc. In some embodiments, such as in an embodiment shown in FIG. 20C, a contoured peripheral portion of an insert 140 can be in the form of a concave radius r' of about 45 mm, although the concave radius r' can be in a range of about 1 mm to 100 mm, about 15 mm to 80 mm, about 45 mm to 60 mm, etc.

Figure 21B:
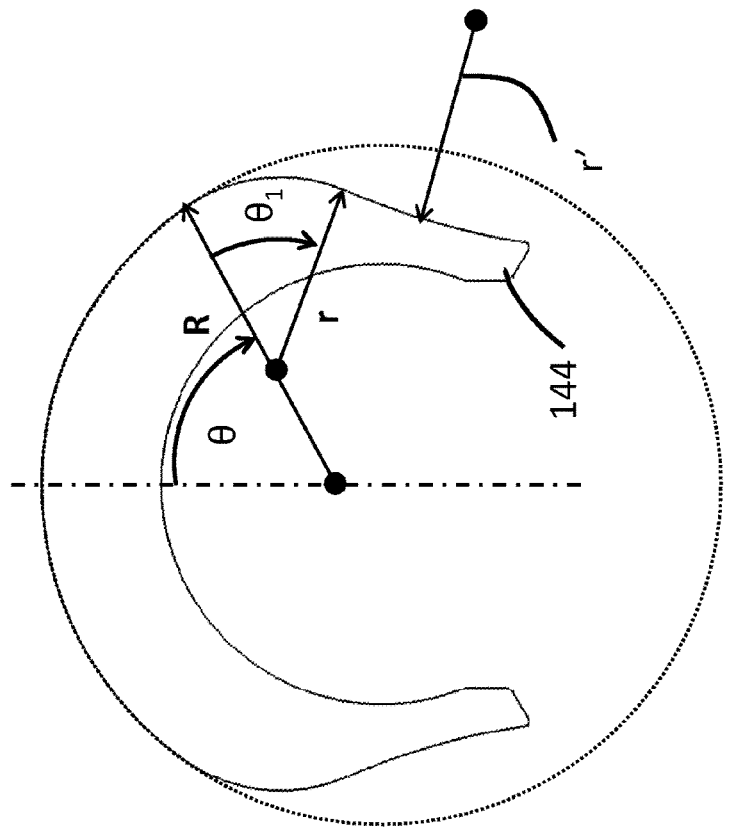
FIG. 21B is a schematic view of an embodiment of a mobile insert showing a set of measurement variables, the mobile insert having a contoured peripheral surface created using a combination of multiple convex radii and a concave radius.
Figure 21A:
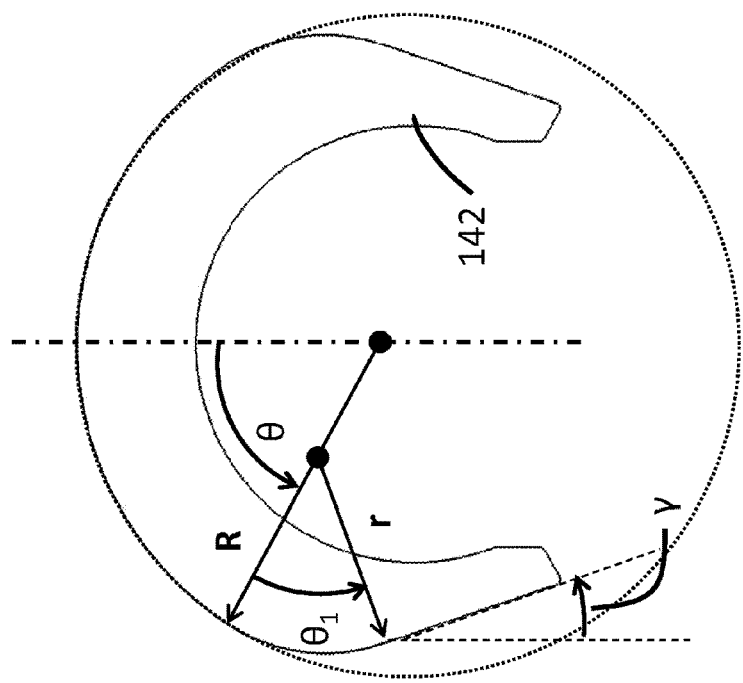
FIG. 21A is a schematic view of an embodiment of a mobile insert showing a set of measurement variables, the mobile insert having a contoured peripheral surface created using a combination of multiple convex radii and a chamfer.

In some embodiments, a combination of smaller convex radii, concave radii, and chamfers can be used to contour an outer articular surface of a mobile insert, as shown in embodiments illustrated in FIGS. 21A and 21B. In one embodiment shown in FIG. 21A, a contoured outer articular surface of a mobile insert 142 can be composed of a radius R matching an overall spherical radius until a theta angle θ, a smaller convex radius r extending from the theta angle θ to $θ_1$, and a chamfer of angle γ extending from $θ_1$ to the peripheral edge or implant rim. In another embodiment shown in FIG. 21B, a contoured outer articular surface of a mobile insert 144 can be composed of a radius R matching an overall spherical radius and extending to a theta angle θ, a smaller convex radius r extending from θ to $θ_1$, and a concave radius r' extending from $θ_1$ to a peripheral edge or implant rim. In yet other embodiments, contouring of a mobile insert's outer articular surface can be achieved with complex spline curves. Thus, a portion of a mobile insert can be contoured in any number of ways so as to move the insert articular surface inwards relative to a surface of an overall spherical geometry of the insert. A maximum inward shift of the contoured surface relative to the overall spherical geometry can be at least about 1 mm, e.g., greater than about 1.5 mm, greater than about 2 mm, greater than about 8 mm etc. In some embodiments, the maximum inward shift of the contoured surface relative to the overall spherical geometry can be less than about 1 mm.

Angular Location for Start of Peripheral Contouring

Figure 22B:
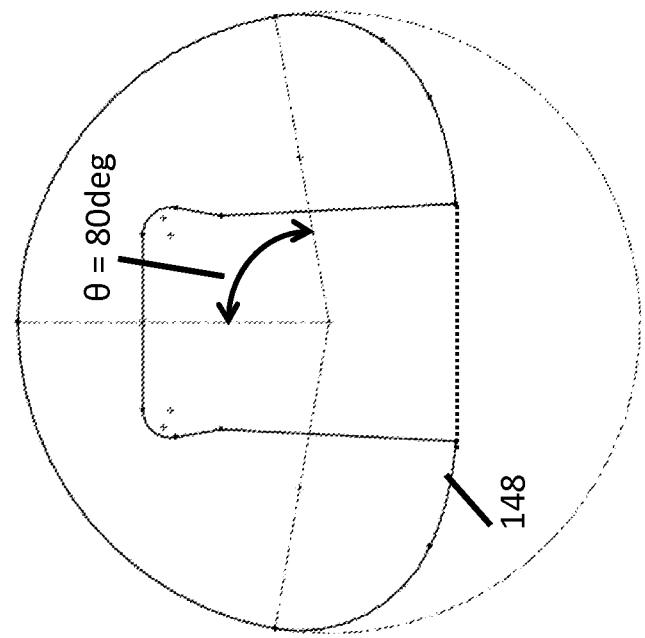
FIG. 22B is a schematic view of one embodiment of a femoral head with peripheral surface contouring starting at theta angle (θ) of about 90.5° relative a femoral head axis.
Figure 22A:
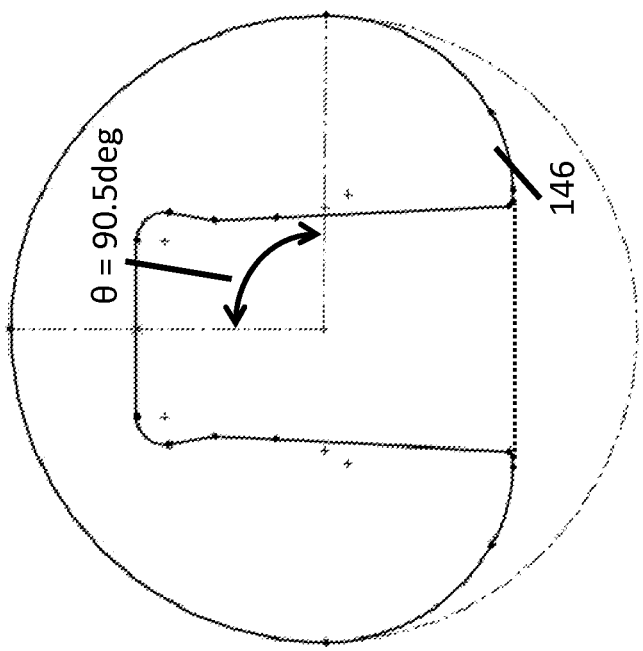
FIG. 22A is a schematic view of one embodiment of a femoral head with peripheral surface contouring starting at theta angle (θ) of about 80° relative a femoral head axis.

In some embodiments, contouring of a femoral head or mobile insert articular surface, such as with a change in radius of curvature, is such that a theta angle θ is at least about 80°, and but not greater than about 115° (see FIGS. 10 and 12). Exemplary embodiments of femoral heads 146, 148 with a theta angle θ of 90.5°, and a theta angle θ of 80°, are shown in FIGS. 22A and 22B, respectively. Reason(s) for peripheral contouring with this range of theta angle θ are described below.

One of the design considerations for hip arthroplasty implants can be maximizing resistance to dislocation. Dislocation typically occurs when a femoral neck of an implant impinges against an acetabular rim, causing a femoral head or mobile insert of the implant to move out of the implant's acetabular component with continued hip joint rotation. The resistance to dislocation can be described in terms of jump distance. This jump distance indicates an amount of displacement the femoral head or mobile insert can undergo prior to a lateral dislocation out of the acetabular component. Generally, the larger an overall spherical radius of the femoral head or mobile insert, the greater the jump distance and resistance to dislocation. However, if contouring of the femoral head or mobile insert is started too soon, such that a theta angle θ is ≤about 60°, the dislocation resistance of the implant can be reduced. This is shown schematically in FIG. 23 for femoral heads and in FIG. 56 for mobile inserts.

Figure 23:
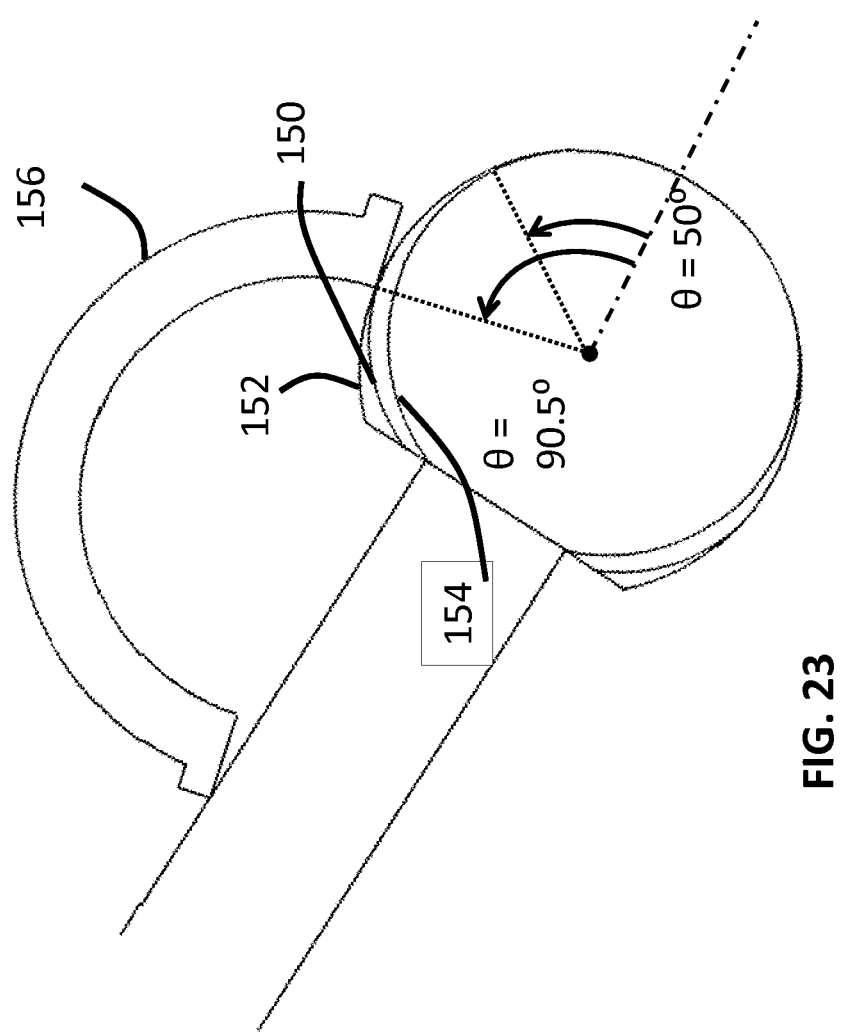
FIG. 23 is a schematic view showing two different embodiments of a femoral head and a conventional femoral head at the point of eminent dislocation out of an acetabular component.
Figure 24:
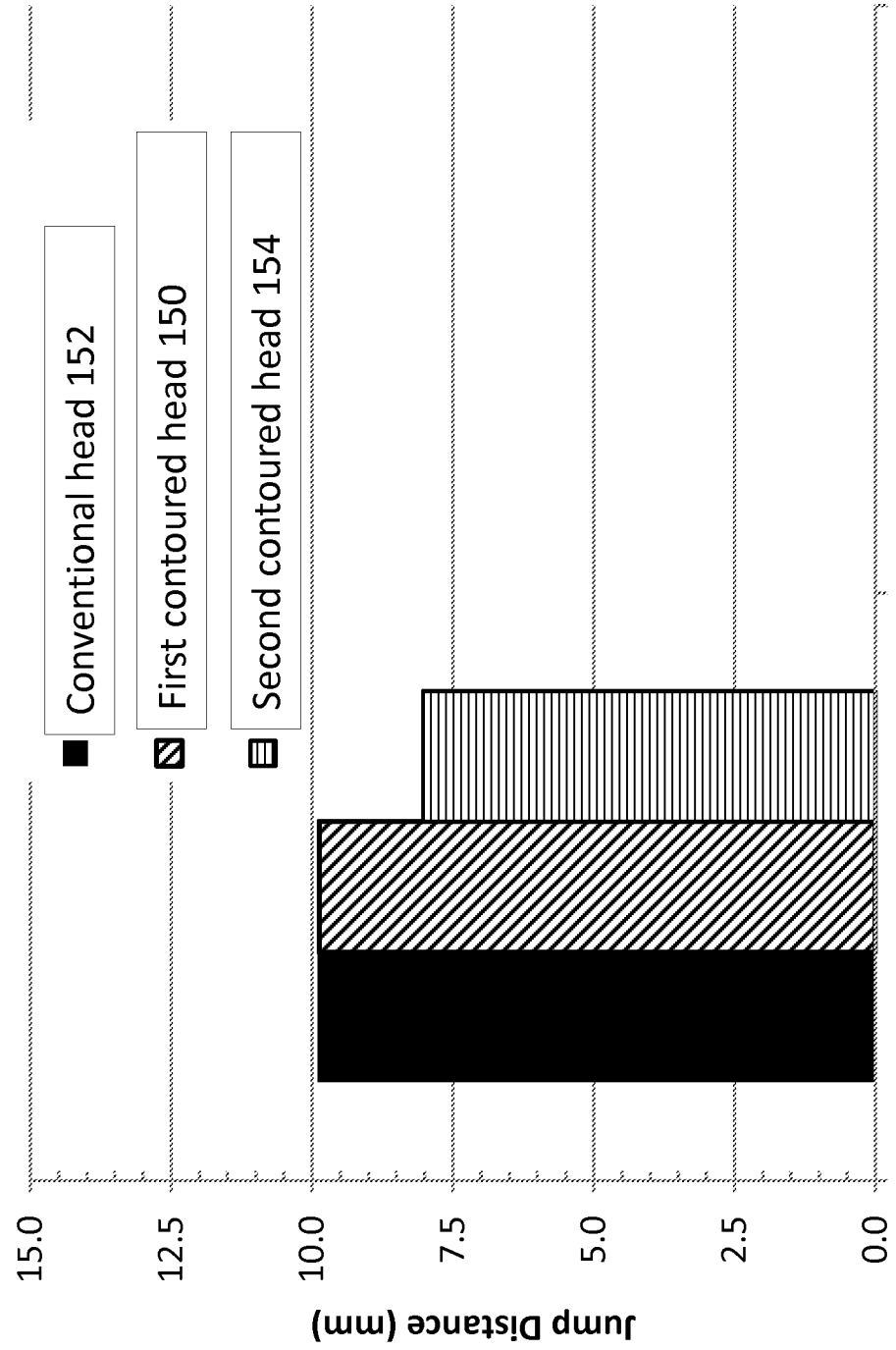
FIG. 24 is a graph showing the jump distance for two different embodiments of a femoral head compared to a conventional femoral head.

At a point of eminent dislocation, as shown in FIG. 23, an acetabular rim of an acetabular shell/liner 156 contacts a first femoral head 150 (having θ=90.5°) and a conventional femoral head 152 at a same location on non-contoured regions of the heads 150, 152. Hence, a jump distance for the first femoral head 150 and the conventional femoral head 152 are identical. However, at a point of eminent dislocation for a second femoral head 154 with a theta angle θ of 50°, the acetabular rim would contact the femoral head 154 on the contoured region. Hence, a jump distance for the second femoral head 154 can be reduced relative to the conventional femoral head 152 of equivalent overall spherical radius, and relative to the first femoral head 150. As shown in FIG. 24, the jump distance for the first femoral head 150 is identical to that of the conventional femoral head 152 of equivalent overall spherical radius (R=18 mm in this illustrated embodiment). However, the jump distance for the second femoral head 154 is less than, e.g., about 2 mm less than, that of the conventional femoral head 152 of equivalent overall spherical radius, and relative to the first femoral head 150.

Figure 56:
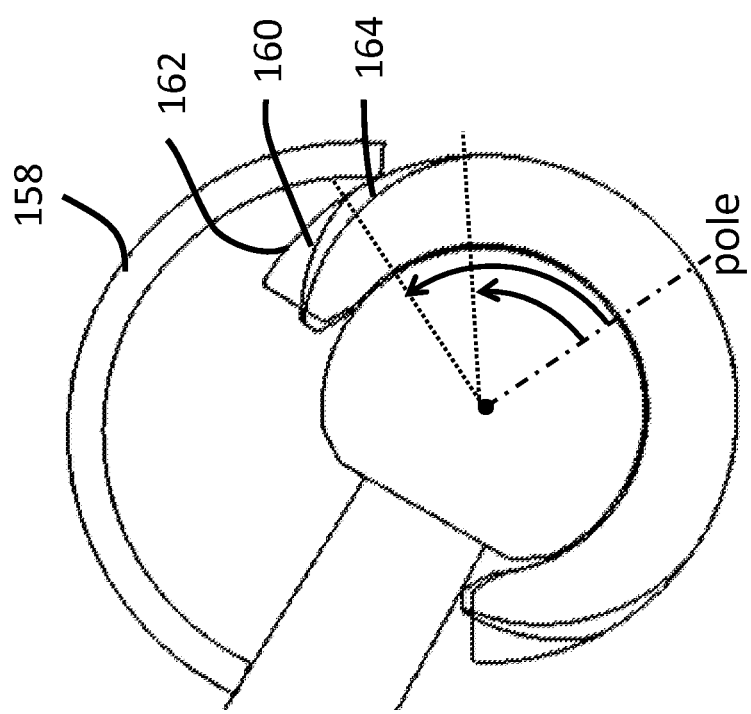
FIG. 56 is a schematic view showing two embodiments of a mobile insert and a conventional mobile insert at a point of eminent dislocation out of an acetabular component.
Figure 57:
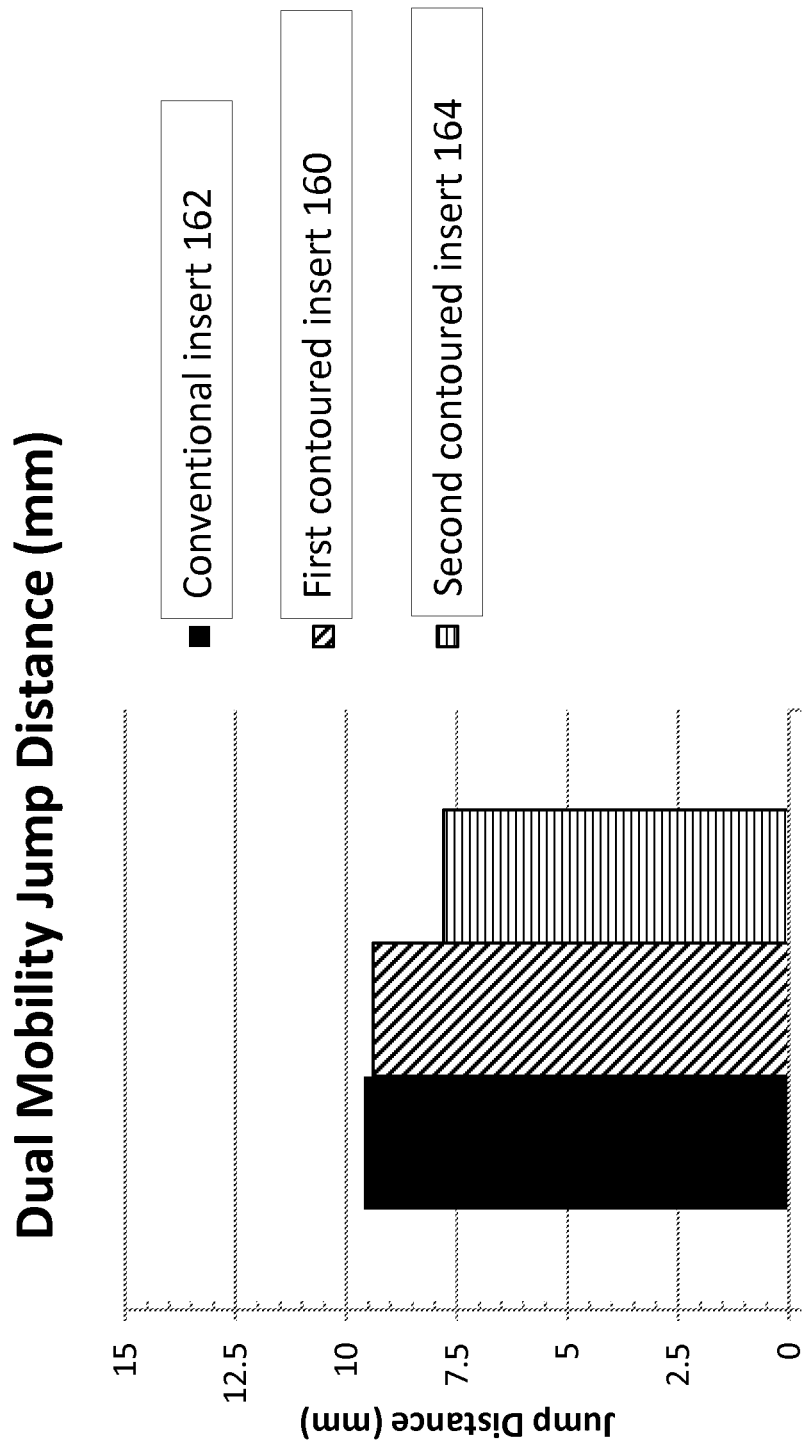
FIG. 57 is a graph showing jump distance for the two mobile inserts of FIG. 56 compared to the conventional mobile insert of FIG. 56.

Similarly, at a point of eminent dislocation, as shown in a dual mobility implant dislocation schematic of FIG. 56, an acetabular rim of an acetabular shell/liner 158 contacts a first mobile insert 160 (having θ=90°), and a conventional mobile insert 162 at a same location on the non-contoured regions of the inserts 160, 162. Hence, a jump distance for the first mobile insert 160 and the conventional mobile insert 162 are identical. However, at a point of eminent dislocation for a second mobile insert 164 with a theta angle θ of 60°, the acetabular rim would contact the mobile insert 164 on the contoured region. Hence, a jump distance for the second mobile insert 164 is reduced relative to the conventional mobile insert 162 of equivalent overall spherical radius, and relative to the first mobile insert 160. As shown in FIG. 57, the jump distance for the first mobile insert 160 is identical to that of the conventional mobile insert 162 of equivalent overall spherical radius (R=22 mm in this illustrated embodiment). However, the jump distance for the second mobile insert 164 is less than, e.g., about 1.7 mm, that of the conventional mobile insert 162 of equivalent overall spherical radius, and relative to the first mobile insert 160.

Ensuring sufficient contact area between a femoral head and an acetabular shell/liner or between a mobile insert and acetabular shell/liner can minimize risk of failure or accelerated damage of the implant components. For a contoured femoral head or mobile insert, starting the contouring too soon (e.g., theta angle θ≤about 80°) can lead to reduction in contact area relative to a conventional design, which may not be desirable. FIG. 25 shows results of a series of finite element analyses for a femoral head articulating against an acetabular liner. In these simulations, the peak in vivo joint loads and corresponding in vivo joint kinematics determined by Bergmann et al. were used (see Bergmann et al. "Hip Contact Forces And Gait Patterns From Routine Activities," *J Biomech.* 2001 July, 34(7):859-71.). The femoral head and acetabular shell were treated as rigid, and the acetabular liner was modeled as UHMWPE with elastoplastic material model. The table in FIG. 25 shows the contact area between the femoral head and acetabular liner in $mm^2$, and the percent change in contact area for the contoured femoral head 148, 150 of FIGS. 22B and 23 relative to the conventional femoral head 152 of FIG. 23. As shown in FIG. 25, the first femoral head 150 with theta angle θ of 90° shows no changes in contact area when compared to the conventional femoral head 152 (see also the formal head 146 of FIG. 22A with theta angle θ of 90°, comparable in result to the first femoral head 150). However, the femoral head 148 with the theta angle θ of 80° shows substantial reduction in contact area compared to the conventional femoral head 152.

While a femoral head or mobile insert articular surface can be contoured such that a theta angle θ is at least about 80°, the theta angle θ can be less than about 115°. This can achieve substantial soft-tissue relief (see FIG. 9).

Prior Art Axisymmetric Femoral Heads

Figure 26B:
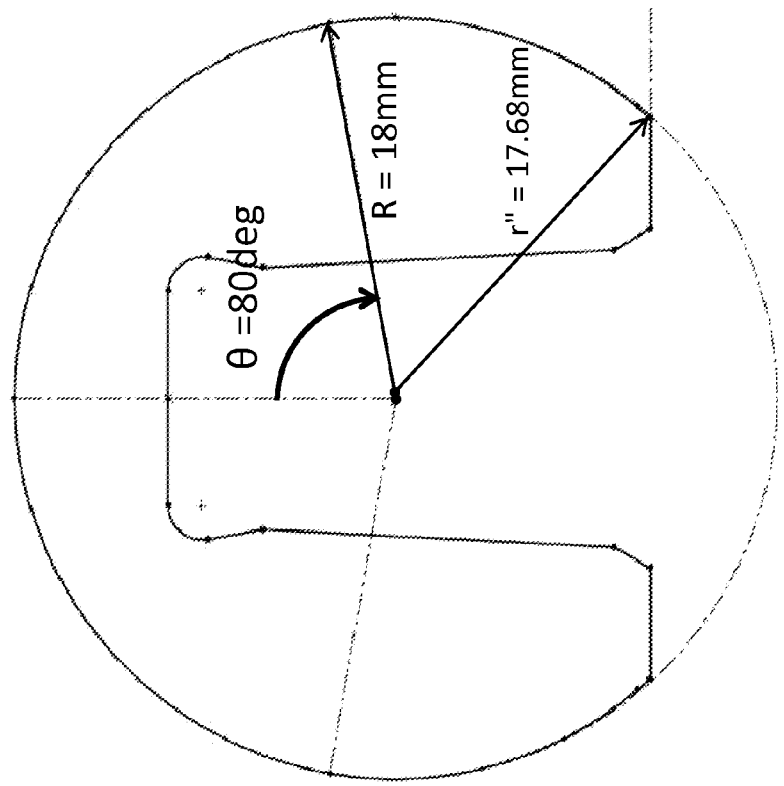
FIG. 26B (PRIOR ART) is a schematic view of another Prior Art femoral head design
Figure 26A:
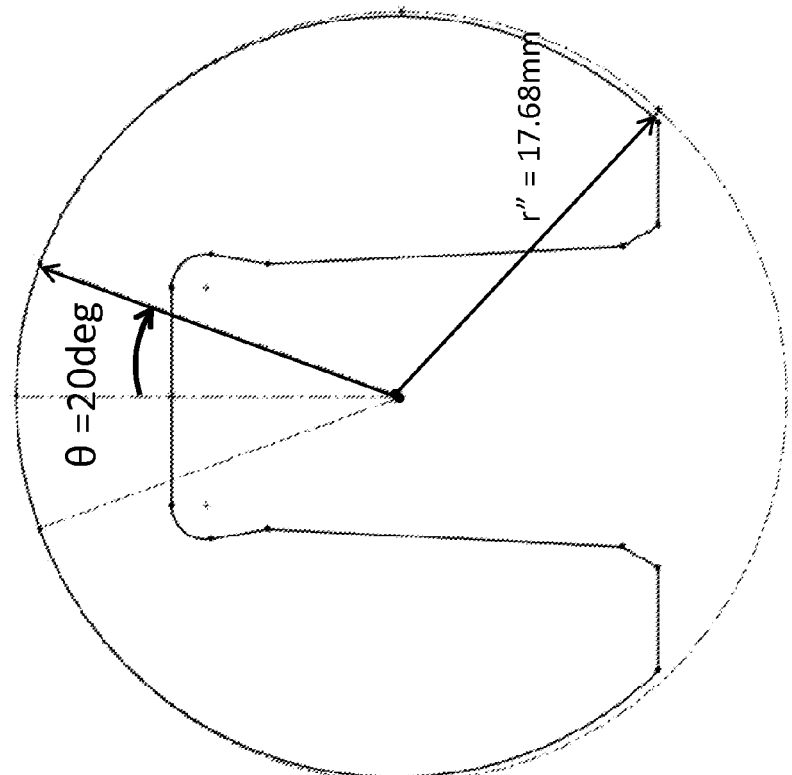
FIG. 26A (PRIOR ART) is a schematic view of a Prior Art femoral head design
Figure 26C:
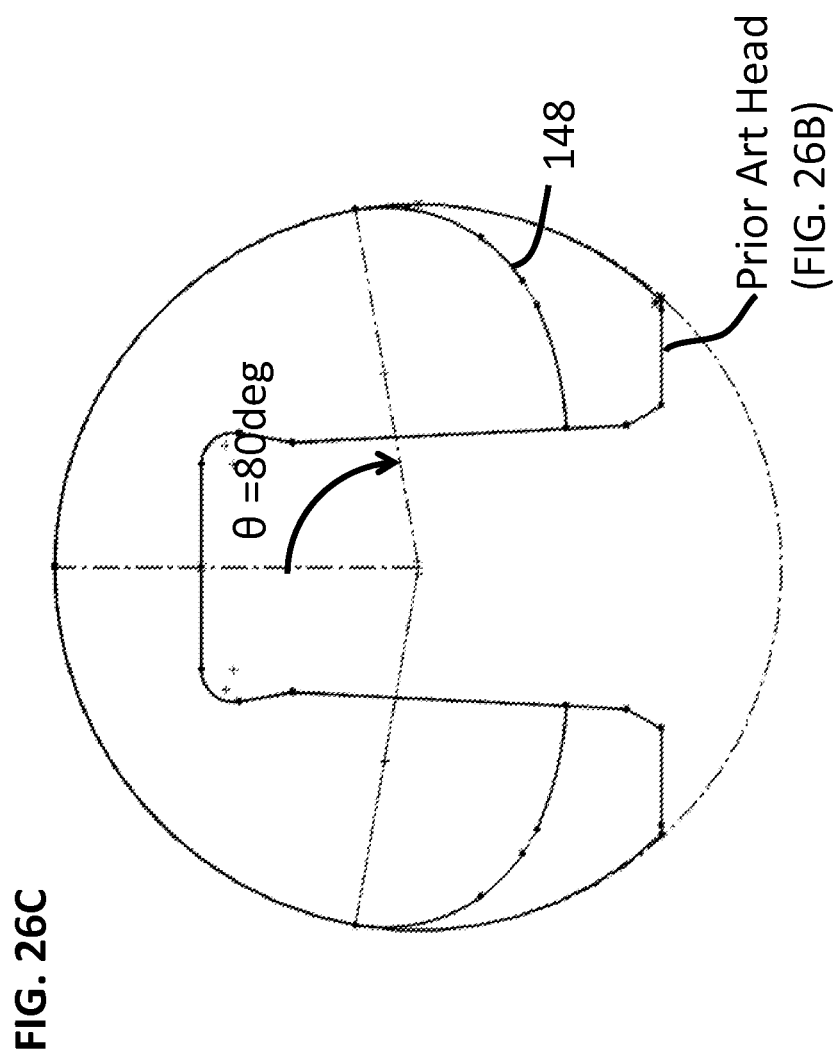
FIG. 26C is a schematic overlay of prior art femoral head design of FIG. 26B and preferred embodiment of FIG. 22A FIG. 26D (PRIOR ART) is a schematic view of a Prior Art femoral head design with a peripheral chamfer

Conventional axisymmetric femoral heads are briefly described below for purposes of comparison with axisymmetric femoral heads disclosed herein. In a hip implant, the joint load is supported by a contact area between the implant's femoral head and acetabular component, extending over a limited portion of the femoral head articular surface. Axisymmetric femoral head designs that alter the articular surface geometry to reduce this load bearing contact area have been described in prior art. For example, U.S. Pat. No. 6,059,830 filed Aug. 3, 1998 entitled "Low Wear Ball And Cup Joint Prosthesis" describes a metal-on-metal femoral head with a portion of the femoral head articular surface having a radius R closely matching that of the acetabular component. Outside this zone of intimate contact, the femoral head radius is reduced slightly from R to r", such that for R=18 mm, 17.68 mm<r"<17.98 mm. This creates a clearance between the acetabular component and the femoral head surfaces, thereby limiting the articular contact area to the region of radius R. In this prior art, the shaping of the femoral head is configured such that theta angle θ is ≤about 80° (preferably ≤about 50°), and occurs well within the load bearing region of a conventional femoral head. This is done so as to reduce articular contact area and thereby articular wear. Additionally, in this prior art, the shaping of the femoral head results in negligible removal of material from the peripheral portion of the implant to provide any meaningful soft-tissue relief. FIGS. 26A and 26B show prior art femoral head designs of U.S. Pat. No. 6,059,830, with a theta angle θ ranging from 20° to 80° and with a contoured radius r"=17.68 mm (smallest value from the possible range of 17.68 mm<r"<17.98 mm for R=18 mm). In FIG. 26A, there is negligible inward shift relative to overall spherical geometry ($\delta_i$=0.44 mm). In FIG. 26B, there is negligible inward shift relative to overall spherical geometry ($\delta_i$=0.12 mm). Thus, the prior art describes less than 0.44 mm of inward shift of the peripheral articular surface relative to the overall spherical geometry of the femoral head. In contrast, in embodiments of orthopedic implants disclosed herein, peripheral contouring is configured such that a theta angle θ is ≥about 80°. This result in contouring of a femoral head outside of a load bearing region of a conventional femoral head, and therefore the load bearing contact area is not reduced. In orthopedic implants disclosed herein, contouring of a femoral head is configured to create substantial inward shift (e.g., ≥about 1 mm) of a peripheral articular surface so as to provide meaningful soft-tissue relief. FIG. 26C shows an overlay of the femoral head 148 embodiment of FIG. 22B, and the prior art femoral head of FIG. 26B. As shown in FIG. 26C, in contrast to the femoral head 148, the prior art head results in negligible inward shift of the peripheral portion of the femoral head relative to the overall spherical geometry of the femoral head.

Figure 26D:
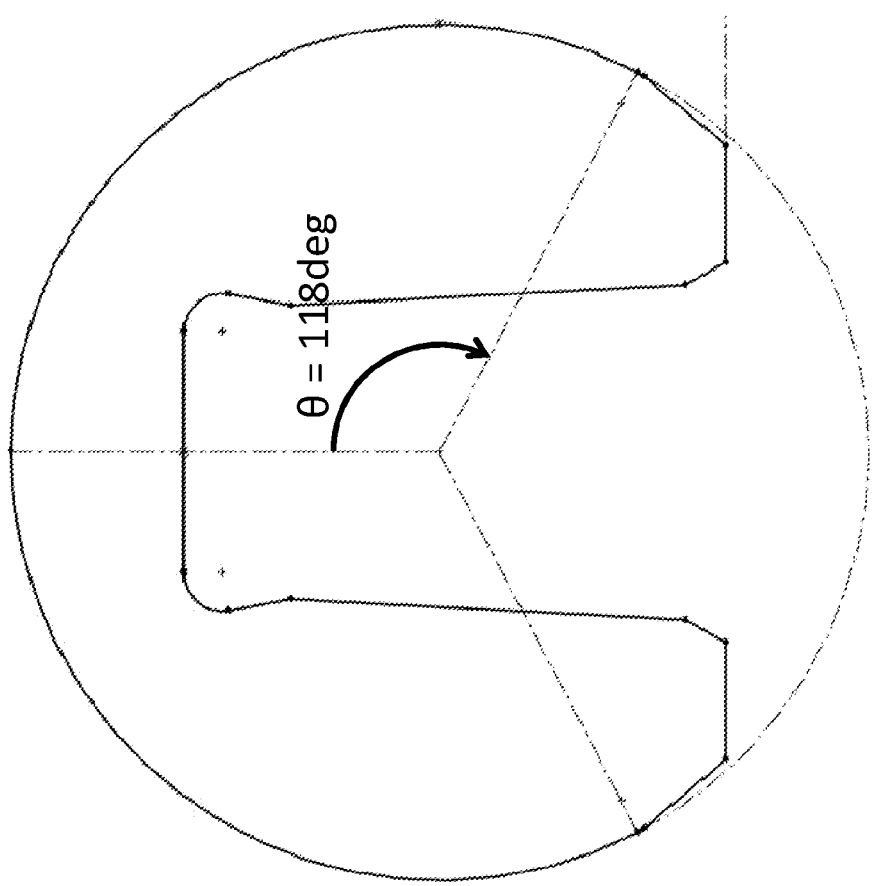
FIG. 26E is a schematic overlay of Prior Art femoral of FIG. 26D and preferred embodiment of FIG. 22A
Figure 26E:
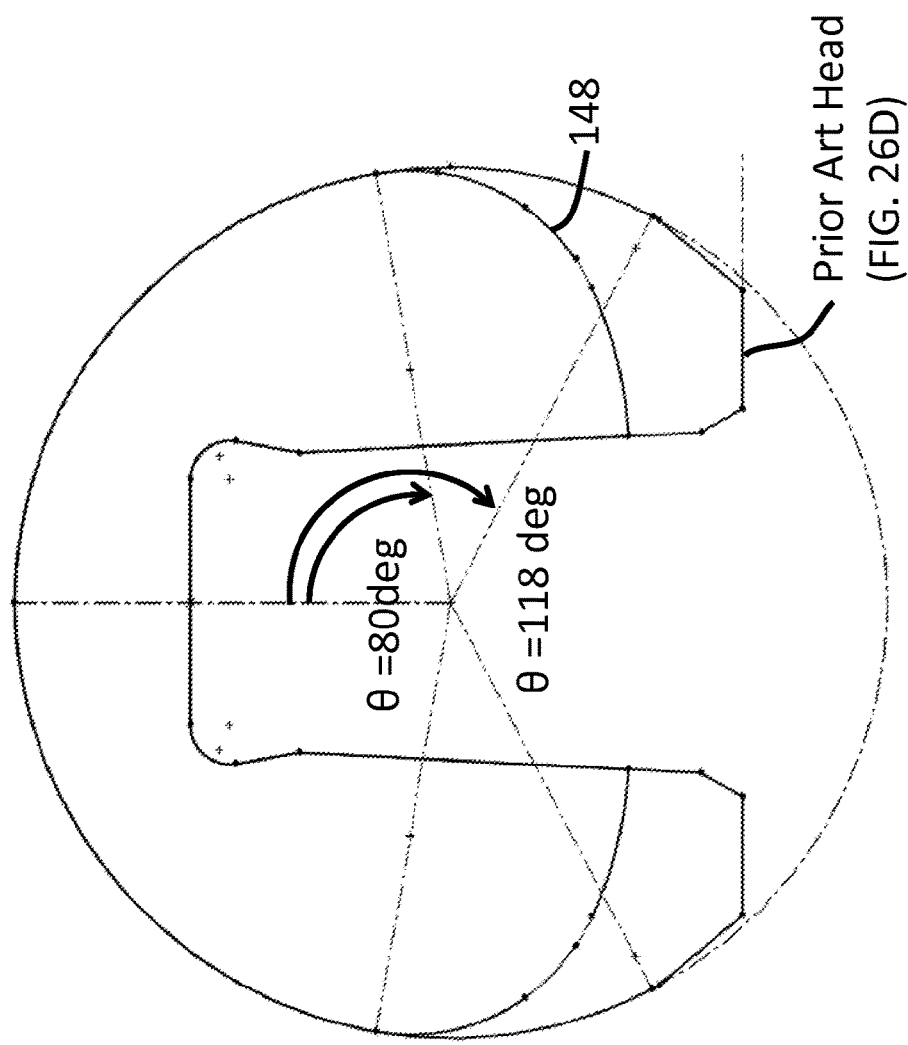

Many conventional femoral heads use a short chamfer to join the femoral head articular surface to the femoral head rim. Often this chamfer is provided as a surface for laser marking of the implant, such as with a convention femoral head shown in FIG. 26D. However, the theta angle θ associated with such chamfers in conventional implants is greater than about 118°. Thus, any peripheral surface contouring resulting from such chamfers occurs well beyond the articular margin of the native femoral head to provide any meaningful soft-tissue relief (see FIG. 9). FIG. 26E shows an overlay of the femoral head 148 embodiment of FIG. 22B, and the prior art femoral head of FIG. 26D with a chamfer resulting in theta angle θ of 118°. As shown in FIG. 26E, in contrast to the femoral head 148 of FIG. 22B, the peripheral surface contouring resulting from the chamfer in the femoral head of FIG. 26D leads to negligible inward shift of the articular surface relative to the overall spherical geometry of the femoral head, and occurs well beyond the articular margin of the native femoral head to provide any meaningful soft-tissue relief.

Use of Convex Radius to Begin Peripheral Contouring

Figure 27:
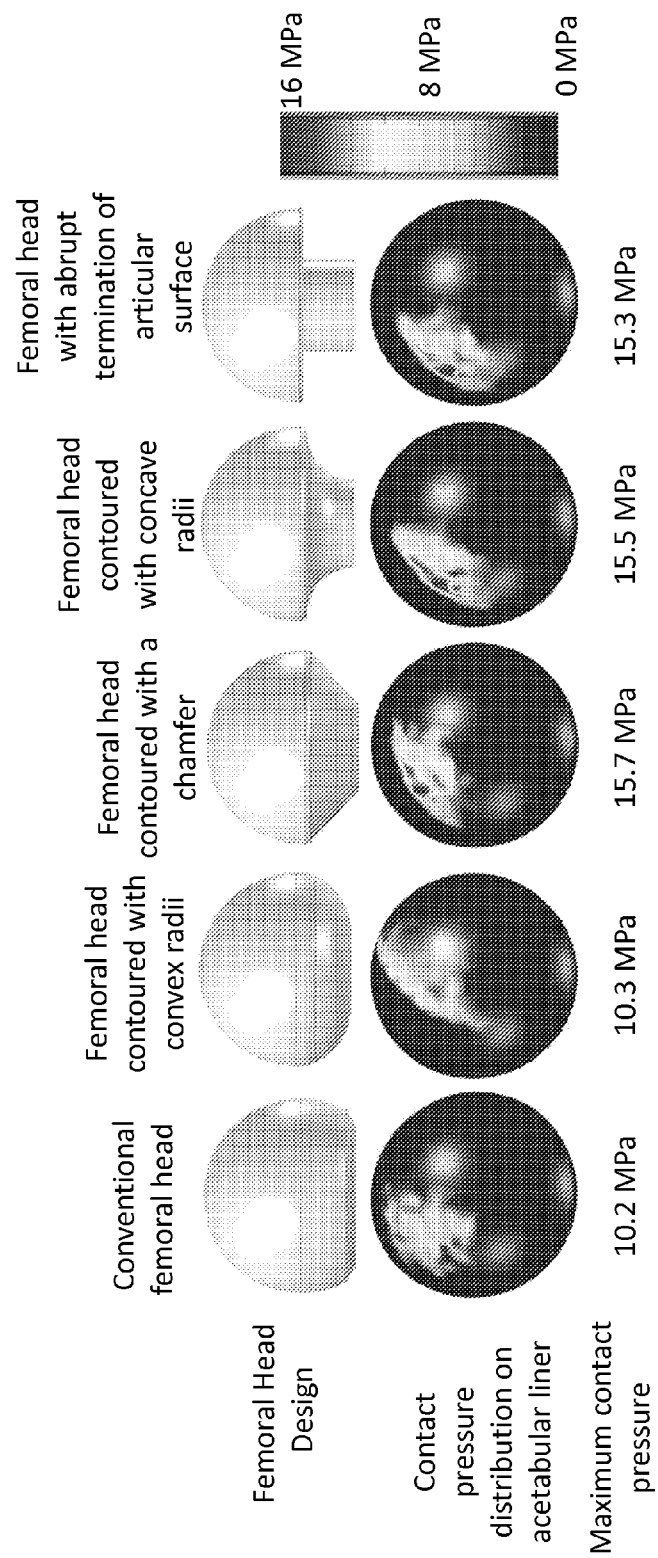
FIG. 27 shows contact stress between an ultra-high molecular weight polyethylene acetabular liner and various femoral heads, including a conventional femoral head, and femoral head embodiments with peripheral articular surface contoured using different profiles.

While a peripheral portion of a femoral head or mobile insert can be contoured in any number of ways, in an exemplary embodiment, the contouring immediately following a non-contoured region of radius R begins with a convex radius r (see FIGS. 10, 16A, and 17A-17C). This convex radius r can be greater than about 2 mm, e.g., greater than about 5 mm, greater than about 8 mm, greater than about 12 mm, etc. The convex radius r smoothly blends into the non-contoured portion of radius R and has an arc angle $\theta_1$ of about 35°, but can be in the range of about 2° to 100°, about 30° to 80°, about 45° to 65° etc. (see FIGS. 17A and 17B). The use of a convex radius, as opposed to a chamfer or concave radius, prevents a sharp transition from the non-contoured non-peripheral portion to the contoured peripheral portion of the femoral head (see FIGS. 16B and 16C). At extremes of hip joint motion this transition region can contact the acetabular component, and a sharp transition can lead to high contact stresses. FIG. 27 shows contact pressure between an UHMWPE acetabular liner and various cobalt chromium femoral heads, including a conventional femoral head 166 composed of single radius R (18 mm for the illustrated conventional femoral head), and femoral head embodiments composed of a radius R (18 mm for each of the four illustrated embodiments having maximum contact pressure of at least 10.3 MPa) having various contoured peripheral profiles. In the femoral head embodiment contoured with convex radii, the peripheral contouring begins with a convex radius and is composed of two convex radii. In the femoral head embodiment contoured with a chamfer, the peripheral contouring is achieved with a chamfer. In the femoral head embodiment contoured with concave radii, the peripheral contouring is achieved with a concave radius. In the femoral head embodiment with abrupt termination of articular surface, the peripheral contouring is achieved by abrupt termination of the femoral articular surface, resulting in an orthogonal edge. As shown in FIG. 27, the contact pressure between the femoral head contoured with convex radii and the acetabular liner is similar to the contact pressure between the conventional femoral head and the acetabular liner. However, the contact pressures for the other three femoral head embodiments shown in FIG. 27 are significantly higher.

Contouring of Femoral Articular Surface in Modular Implants

Figure 28F:
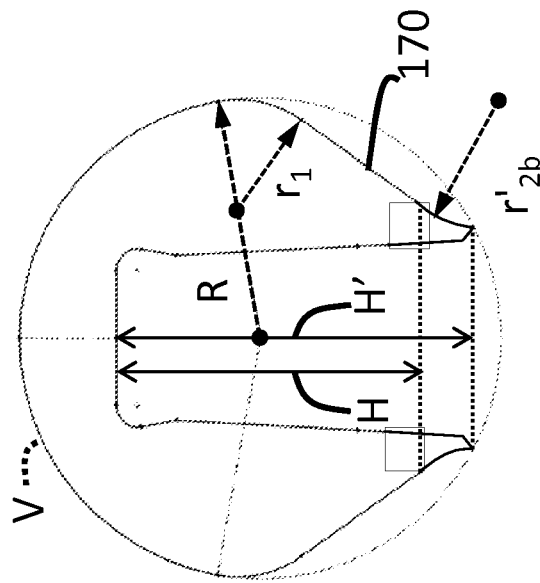
FIG. 28F is a schematic view of one embodiment of a femoral head from FIG. 28A. In this embodiment the peripheral contouring is achieved with a combination of convex radius, chamfer and a concave radius, to increase the taper junction length relative to the conventional design.
Figure 28E:
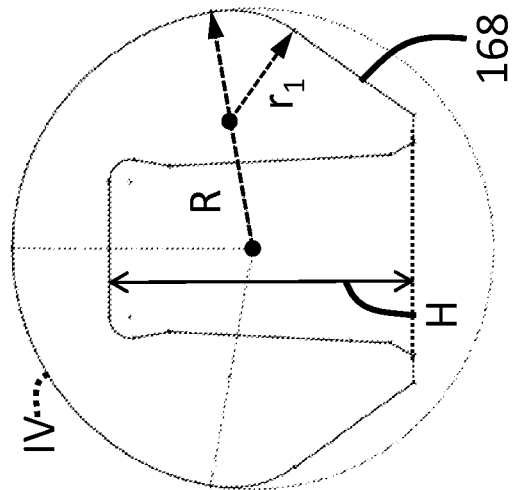
FIG. 28E is a schematic view of one embodiment of a femoral head from FIG. 28A. In this embodiment the peripheral contouring is achieved with a convex radius and a chamfer to retain the taper junction length of the conventional design.

As described above, peripheral contouring can start with a convex radius. Following the convex radius, a remainder of the peripheral portion can be completed in any manner, such as with any combination of convex radii ($r_i$), concave radii, or chamfers (see FIGS. 16A-17C). In femoral heads with a modular taper junction, the use of a series of convex radii $r_i$ can result in reduction of a length H of a female taper surface, and hence a length of the taper junction. One such embodiment (I) is shown in FIGS. 28A and 28B. Excessive reduction of taper junction length may not be desired, as it can affect the strength and stability of the taper junction. In contrast, use of a series of convex radii such as in embodiment (II) shown in FIGS. 28A and 28C, can help retain the length H of the female taper surface. However, this may provide insufficient soft-tissue relief due to reduced inward shift of the peripheral surface of the femoral head. To balance the competing requirements of contouring for soft-tissue relief and maximizing or maintaining the taper junction length, in embodiments (III) and (IV) shown in FIGS. 28A, 28D, and 28E, the peripheral contouring is completed with the aid of one or more concave radii or chamfers 168 (FIG. 28E), 170 (FIG. 28F). The use of concave radii ($r'_{2a}$ for embodiment (III) and $r'_{2b}$ for embodiment (V) of FIGS. 28A and 28F) or chamfer reverses the radius of curvature started by an initial convex radius $r_1$, allowing greater amount of peripheral contouring while maximizing the taper junction length. The female taper surface can also be extended up to the overall spherical geometry of the head, such as in embodiment (V) where H<H'.

Figure 58A:
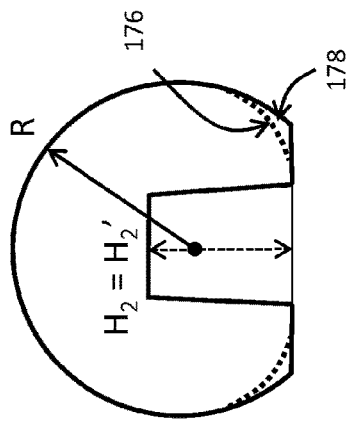
FIG. 58A is a schematic view showing an embodiment of a femoral head as compared to a conventional femoral head.
Figure 58B:
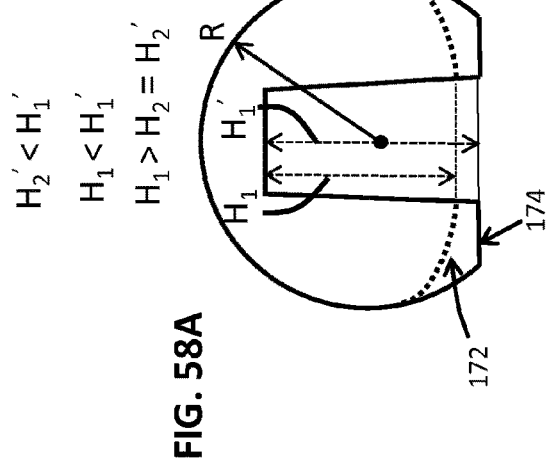
FIG. 58B is a schematic view showing another embodiment of a femoral head compared to an conventional femoral head, the femoral head having the same overall spherical radius as the head of FIG. 58A, different contoured outer surface geometry as the head of FIG. 58A, and different female taper length from the head of FIG. 58A.
Figure 59A:
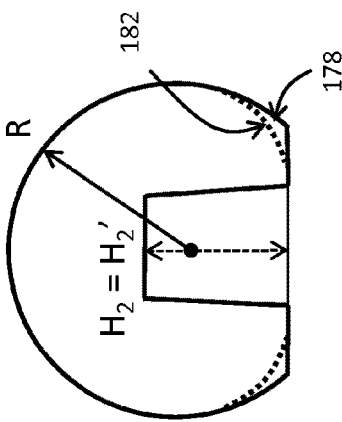
FIG. 59A is a schematic view showing an embodiments of a femoral head compared to the conventional femoral head of FIG. 58A.
Figure 59B:
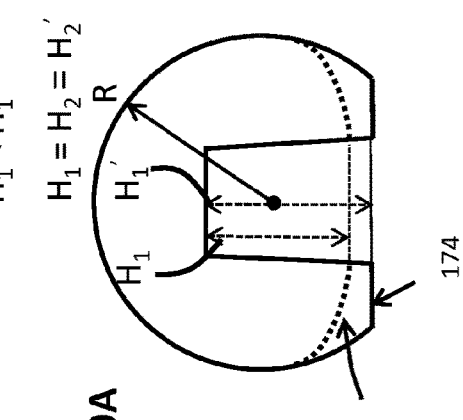
FIG. 59B is a schematic view showing another embodiment of a femoral head compared to the conventional femoral head of FIG. 58B, the femoral head having the same overall spherical radius as the head of FIG. 59A, different contoured outer surface geometry from the head of FIG. 59A, and same female taper length as the head of FIG. 59A.

Within a given modular implant system, contoured femoral heads having the same overall spherical radius can be provided with different outer surface geometries and/or different female taper lengths (see FIGS. 58A-59B). FIG. 58A shows an embodiment of a contoured femoral head 172 overlaid with a conventional femoral head 174 for comparison purposes. FIG. 58B shows another embodiment of a contoured femoral head 176 overlaid with another conventional femoral head 178 for comparison purposes. The contoured head 176 of FIG. 58B has the same overall spherical radius as the head 172 of FIG. 58A, different contoured outer surface geometry from the head 172 of FIG. 58A, and different female taper length from the head 172 of FIG. 58A. FIG. 59A shows an embodiment of a contoured femoral head 180 overlaid with the conventional femoral head 174 for comparison purposes. FIG. 59B shows another embodiment of a contoured femoral head 182 overlaid with the other conventional femoral head 178 for comparison purposes. The femoral head 182 of FIG. 59B has the same overall spherical radius as the head 180 of FIG. 59A, different contoured outer surface geometry from the head 180 of FIG. 59A, and same female taper length as the head 180 of FIG. 59A.

Figure 29A:
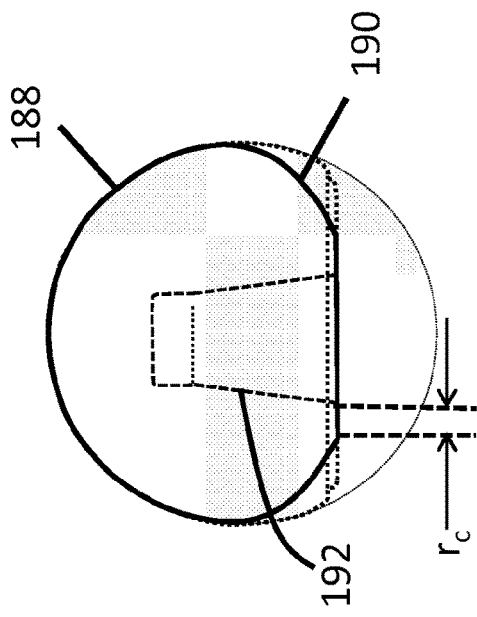
FIG. 29A (PRIOR ART) is a perspective view of a conventional femoral head in relation to the femoral head-neck taper junction.
Figure 29B:
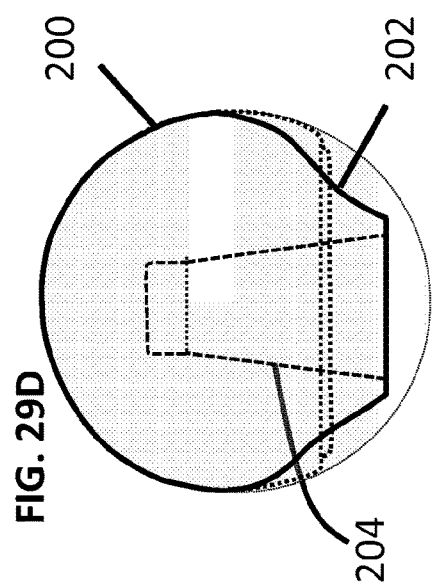
FIG. 29B is a perspective view of an embodiment of a femoral head superimposed on the conventional femoral head of FIG. 29A.
Figure 29C:
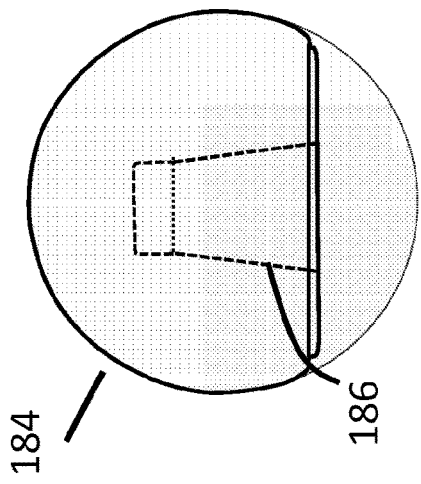
FIG. 29C (PRIOR ART) is a perspective view of a conventional femoral head in relation to an extended portion of a femoral head-neck taper junction.
Figure 29D:
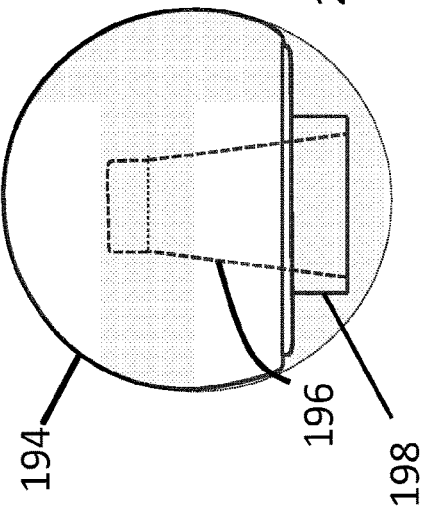
FIG. 29D is a perspective view of an embodiment of a femoral head superimposed on the conventional femoral head of FIG. 29C; the contoured portion of the articular surface merging onto an extended portion of the taper junction

In modular implants, a contouring of an outer surface of a femoral head can approach edges of a taper junction with a radial clearance $r_c$, as shown in FIGS. 29A and 29B. FIG. 29A illustrates a conventional femoral head 184 and conventional taper junction 186. FIG. 29B illustrates an embodiment of a femoral head 188 having a contoured surface 190, and a taper junction 192. The radial clearance can be in a range from about 0 mm to 16 mm, about 5 mm to 15 mm, about 10 mm to 12 mm, etc. In some conventional implants, the taper junction extends below the peripheral edge/rim of the femoral head to allow greater taper junction length or to provide greater flexibility in selection of appropriate prosthetic femoral neck length. However, this abrupt transition results in a pronounced/sharp edge that can impinge on soft tissues, as shown in FIG. 29C which illustrates a conventional femoral head 194, a conventional taper junction 196, and a conventional extended portion 198 of the taper junction 196. To avoid this, in another embodiment of invention femoral head 200 shown in FIG. 29D, contouring of a peripheral portion of a femoral articular surface 202 can be continued to merge with an extended portion of a taper junction 204 to avoid abrupt transition from the femoral head articular surface 202 to the taper junction 204.

Non-Axisymmetric Embodiments

Figures 30, 31A:
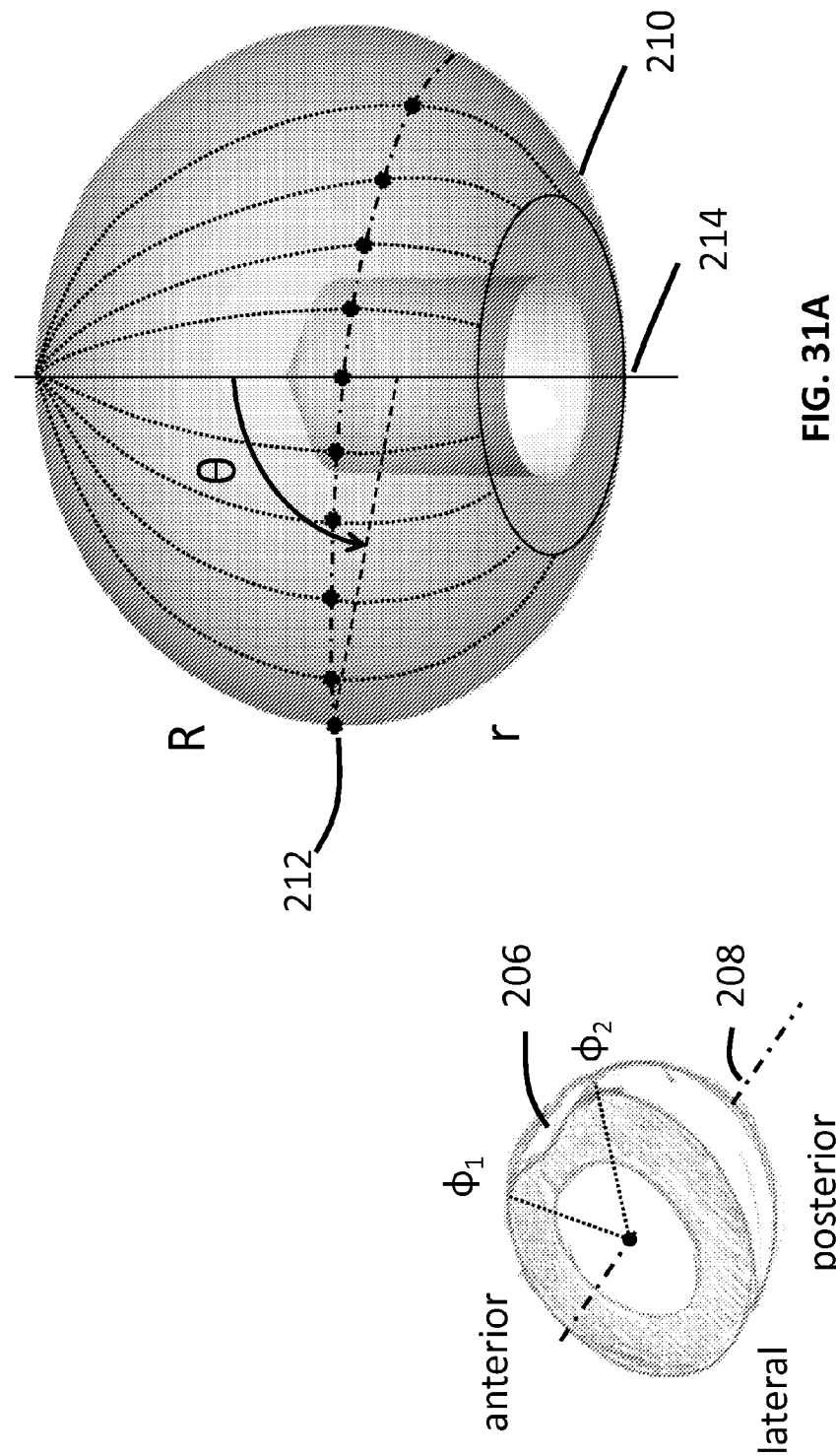
FIG. 30 is a perspective view of an embodiment of a non-axisymmetric femoral head/mobile insert with a partial cut-out or recess.
FIG. 31A is a perspective view of an embodiment of a non-axisymmetric femoral head with the theta angle marking location of transition from a large radius to a smaller peripherial radius varying as a function of azimuth angle measured about a femoral head axis.
Figure 31B:
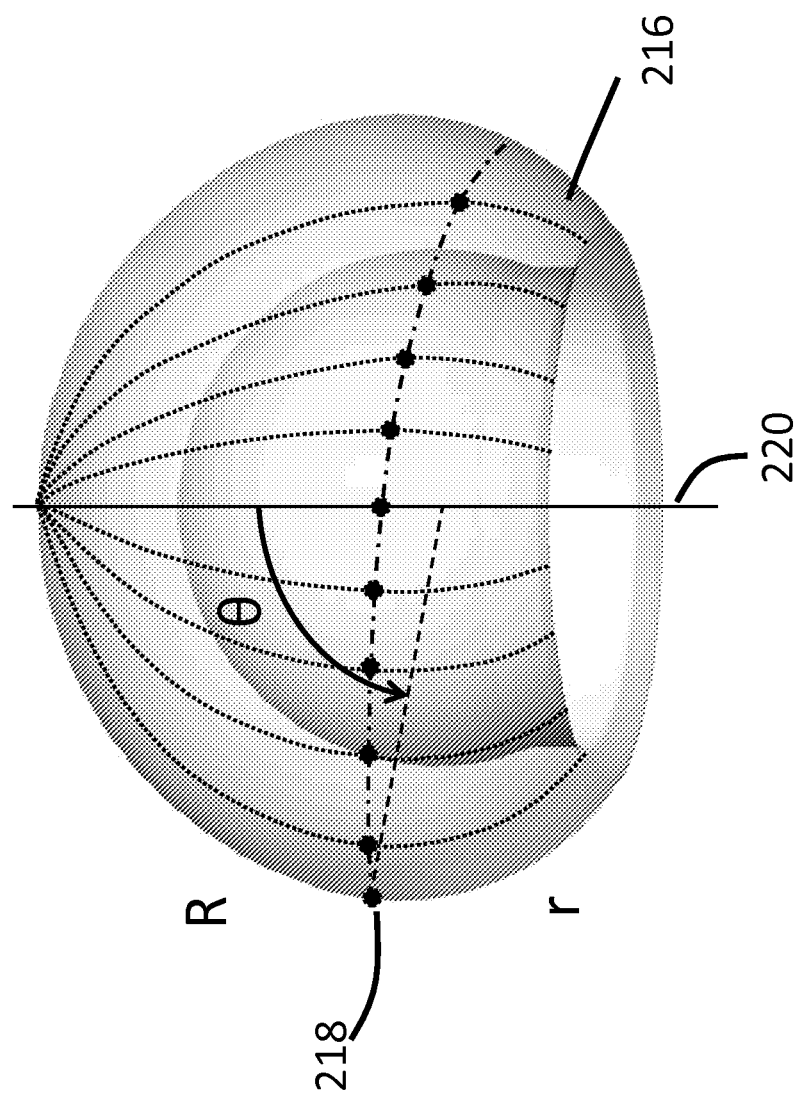
FIG. 31B is a perspective view of an embodiment of a non-axisymmetric mobile insert with the theta angle marking location of transition from a large radius to a smaller peripherial radius varying as a function of azimuth angle measured about a mobile insert axis.

In the previous sections following the "AXISYMMETRIC EMBODIMENTS" heading, axisymmetric embodiments of femoral heads and mobile inserts were described. In other embodiments, a femoral head or mobile insert can have a non-axisymmetric geometry about a femoral head or insert axis such that parameters r, r', θ, α, γ, $r_1$ to $r_n$, $θ_1$ to $θ_n$, etc. vary as a function of an azimuth angle ϕ about the mobile insert or femoral head axis, while the overall angular extent of an articular surface β remains constant. FIG. 30 illustrates an embodiment of a non-axisymmetric femoral head or mobile insert with a partial cut-out or recess 206 that can be configured to provide localized soft-tissue relief. As shown in FIG. 30, contouring of an articular surface can be restricted to an azimuth angle range of $ϕ_1$ to $ϕ_2$ about a femoral head or mobile insert axis 208 so as to create the partial cut-out or recess 206. In other embodiments, partial cut-outs or recesses of femoral heads or mobile inserts can be created at multiple locations. In another embodiment, a theta angle θ marking the transition from a spherical radius R to a contoured peripheral radius r can change as a function of an azimuth angle ϕ. FIG. 31A illustrates an embodiment of a non-axisymmetric femoral head 210 with a theta angle θ marking a transition 212 from a large spherical radius R to a smaller peripherial radius r varying as a function of azimuth angle ϕ about a femoral head axis 214. FIG. 31B illustrates an embodiment of a non-axisymmetric mobile insert 216 with a theta angle θ marking a transition 218 from a large spherical radius R to a smaller peripherial radius r varying as a function of an azimuth angle ϕ about a mobile insert axis 220.

In some non-axisymmetric embodiments of a femoral head or mobile insert, an overall angular extent of an articular surface β can vary as a function of an azimuth angle ϕ about a femoral head or mobile insert axis. FIG. 32A illustrates an embodiment of a non-axisymmetric femoral head 222 with a medial articular surface 226 trimmed to match native femoral head geometry. FIG. 32B illustrates an embodiment of a non-axisymmetric femoral head 224 with medial and lateral articular surfaces 228, 230 trimmed to match native femoral head geometry. Effectively, this results in trimming of some portions of the femoral head. In the embodiment of FIG. 32A, an angular extent of the articular surface 226 is reduced compared to a conventional implant in the medial portion to better match the native femoral head geometry, with β being about 100° and being less than β', with β' being about 120°, and with ϕ being in a range of about 150° to 230°. Similarly, in the embodiment of FIG. 32B, an angular extent of the articular surfaces 228, 230 are reduced relative to a conventional implant in the medial and lateral portions to better match the native femoral head geometry, with β being about 100° and being less than β', with β' being about 120°, and with ϕ being in a range of about 150° to 230°, about 340° to 20°. FIG. 33A illustrates an embodiment of a non-axisymmetric mobile insert 232 with a medial articular surface 234 trimmed to match native femoral head geometry.

FIG. 33B illustrates an embodiment of a non-axisymmetric mobile insert 244 with medial and lateral articular surfaces 236, 238 trimmed to match native femoral head geometry. In the embodiments of FIGS. 33A and 33B, remaining portions 240, 242 of their respective articular surfaces are extended beyond that of conventional implants to compensate for reduction in extraction resistance of the small diameter femoral head from the inner articulation. Effectively, this results in a reduction of angular extent of some portions of the mobile insert articular surface and an increase in angular extent of other portions of the mobile insert articular surface. In the embodiment of FIG. 33A, the angular extent of the articular surface is reduced compared to a conventional implant in the medial portion to better match the native femoral head geometry, with β being about 100° and being less than β', with β being about 120°, and with φ being in a range of about 150° to 230°. Concomitantly, the angular extent of the articular surface is increased in other locations beyond that of a conventional implant, with β being greater than β', and with φ being in a range of about 0° to 150°, about 230° to 360°. Similarly, in the embodiment of FIG. 33B, the angular extent of the articular surface is reduced relative to a conventional implant in the medial and lateral portions to better match the native femoral head geometry, with β being about 100° and being less than β', with β' being about 120°, and with φ being in a range of about 150° to 230°, about 340° to 20°, etc. Concomitantly, the angular extent of the articular surface is increased in other locations beyond that of a conventional implant, with β being greater than β' and with φ being in a range of about 24° to 150°, about 230° to 340°.

In a dual mobility implant, a mobile insert of the implant can move relative to both an acetabular shell of the implant as well as a small diameter inner femoral head of the implant. Therefore, it can be beneficial to combine a mobile insert articular surface contouring with design features to guide or control the insert motion in certain directions or degrees-of-freedom, particularly for non-axisymmetric embodiments. This can help keep the mobile insert in a preferred orientation to avoid soft tissue impingement.

Figure 34B:
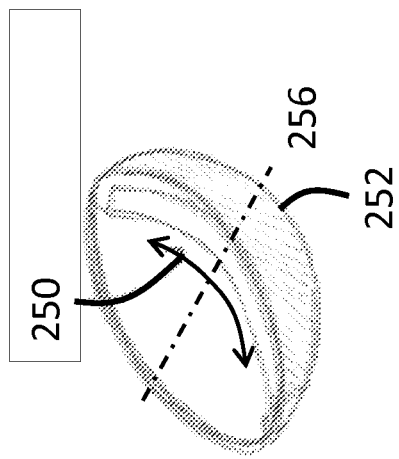
FIG. 34B is a perspective view of an embodiment of an acetabular shell having a guiding track formed therein that is configured to mate with the groove of FIG. 34A.
Figure 34A:
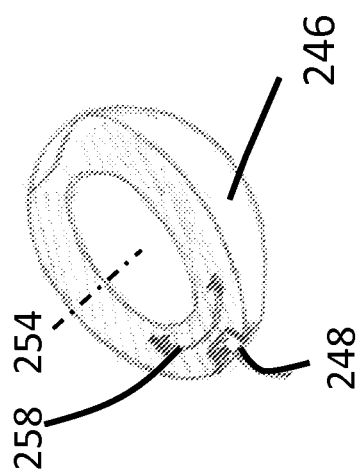
FIG. 34A is a perspective view of an embodiment of a mobile insert having a groove formed thereon.

This control of the mobile insert motion in different directions can be achieved via various locking mechanisms and guiding surfaces. In one embodiment, a circular track on an acetabular shell can be configured to mate with a groove on a mobile insert, thereby allowing full rotational motion parallel to or along the track while restricting rotation about orthogonal axes. FIGS. 34A and 34B illustrate an embodiment of a mobile insert 246 (FIG. 34A) having a groove 248 formed therein that is configured to mate with a guiding track 250 formed on an acetabular shell 252 (FIG. 34B), thereby allowing rotational motion parallel to or along the track 250 while restricting rotation 258 about orthogonal axes. In another embodiment, a circular track formed in an insert can be configured to mate with a groove formed on an acetabular shell, thereby allowing full rotational freedom parallel to or along the track while restricting rotation about orthogonal axes 254, 256 of the insert 246 and the shell 252.

Figure 35C:
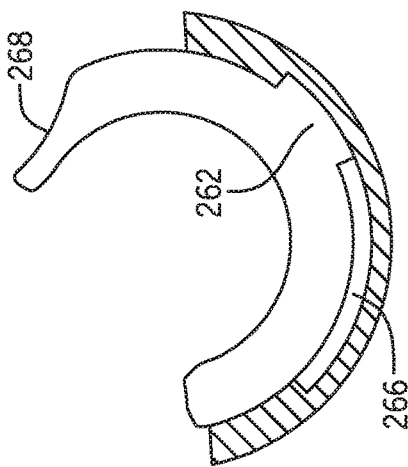
FIG. 35C is a cross-sectional view of the mobile insert and the shell of FIG. 35B, showing the protrusion on the mobile insert seated within the acetabular recess or depression.
Figure 35B:
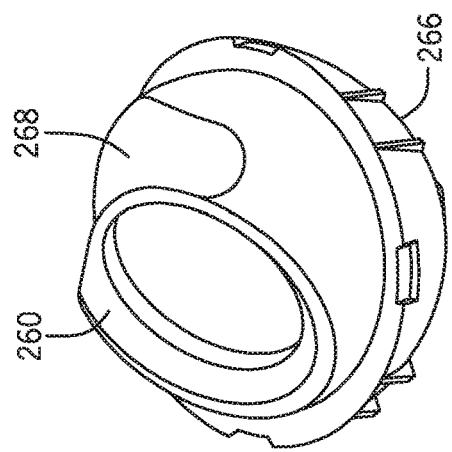
FIG. 35B is a perspective view of the mobile insert of FIG. 35A seated in the acetabular shell of FIG. 35A with the protrusion seated in the recess or depression.
Figure 35A:
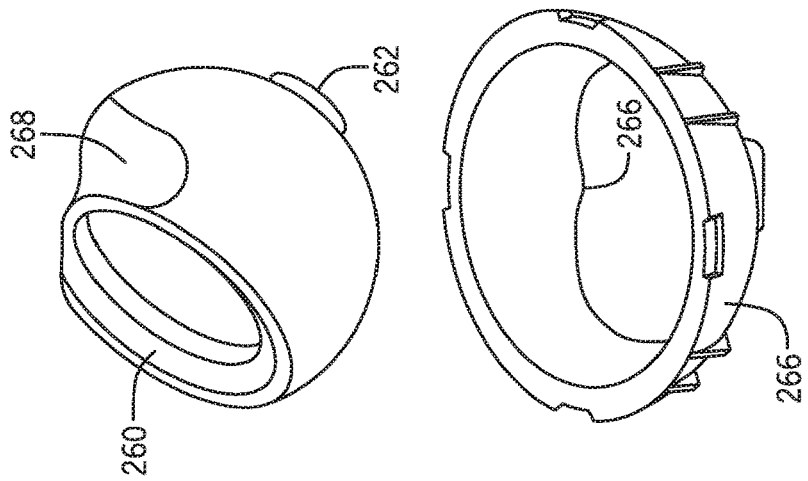
FIG. 35A is an exploded perspective view of an embodiment of a mobile insert having a protrusion extending therefrom, and an embodiment of an acetabular shell having a recess or depression formed therein that is configured to engage the protrusion.

In another embodiment, a protrusion extending from a outer surface of an insert can be configured to be contained within a recess or depression formed on an inner surface of an acetabular shell. FIGS. 35A-35C illustrate an embodiment of a mobile insert 260 where engagement of a protrusion 262 on the insert 262 is configured to be contained within a recess 264 formed in an acetabular shell 266. The mobile insert 260 also includes contouring 268, which can facilitate soft tissue relief as discussed herein. The engagement of the protrusion 262 against a wall of the recess 264 controls an amount of allowed rotation in a given direction. The geometry of the protrusion 262 and the acetabular recess 264 can allow specific and/or different amounts of rotation about different axes before the engagement of the insert protrusion 262 against the recess wall prevents further rotation. In some embodiments, a protrusion from an insert surface and an acetabular recess can have circular profiles. In other embodiments, a protrusion from an insert surface and an acetabular recess can have complex three-dimensional profiles. In still other embodiments, a protrusion from an acetabular surface can be configured to engage a recess in a mobile insert to allow specific and different amounts of rotation about different axes.

Figure 36A:
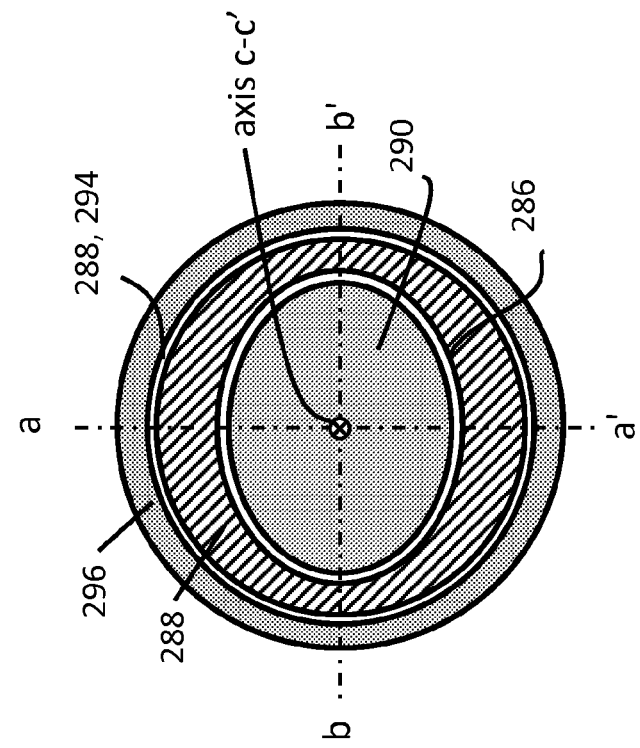
FIG. 36A is a schematic view of an embodiment of a dual mobility implant with non-spherical mating surfaces between an acetabular shell and a mobile insert of the implant.
Figure 36B:
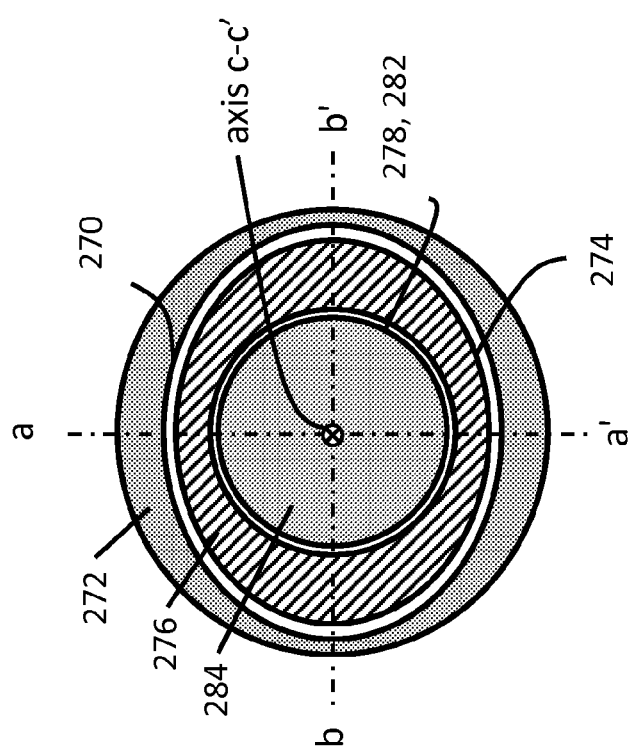
FIG. 36B is a schematic view of another embodiment of a dual mobility implant with non-spherical mating surfaces between a mobile insert, and an femoral head of the implant.

In some embodiments, mating surfaces of an acetabular shell, a mobile insert, or a small diameter inner head can be non-spherical. FIGS. 36A and 36B illustrate embodiments of dual mobility implants with non-spherical mating surfaces between an acetabular shell, a mobile insert, and an inner femoral head. FIGS. 36A and 36B show a top down view of embodiments with out-of-plane axis c-c' being parallel to a femoral head/or mobile insert axis. FIG. 36A illustrates an embodiment in which an inner surface 270 of an acetabular shell 272 and a mating outer surface 274 of an insert 276 are non-spherical, while an inner surface 278 of the insert 280 and a mating surface 282 of a small diameter femoral head 284 are spherical. In this embodiment, at the outer articulation the insert 276 can rotate about orthogonal axes a-a' and b-b'. However, rotation of the insert 276 about axis c-c' is restricted. At the inner articulation, rotation of the insert 276 about all three orthogonal axes a-a', b-b', and c-c' can occur freely. In another embodiment, shown in FIG. 36B, an inner articular surface 286 of a mobile insert 288 and a mating small diameter femoral head 290 are non-spherical, whereas a spherical outer articular surface 292 of the insert 288 mates with a spherical inner surface 294 of an acetabular shell 296. In this embodiment, the insert 288 is free to rotate relative to the acetabular shell 296 in all directions of rotational freedom. However, at the inner articulation the rotation of the insert 288 about axis c-c' is restricted, while rotations about orthogonal axes a-a' and b-b' are permitted.

Creating Non-Axisymmetric Embodiments from Axisymmetric Embodiments

Figure 37:
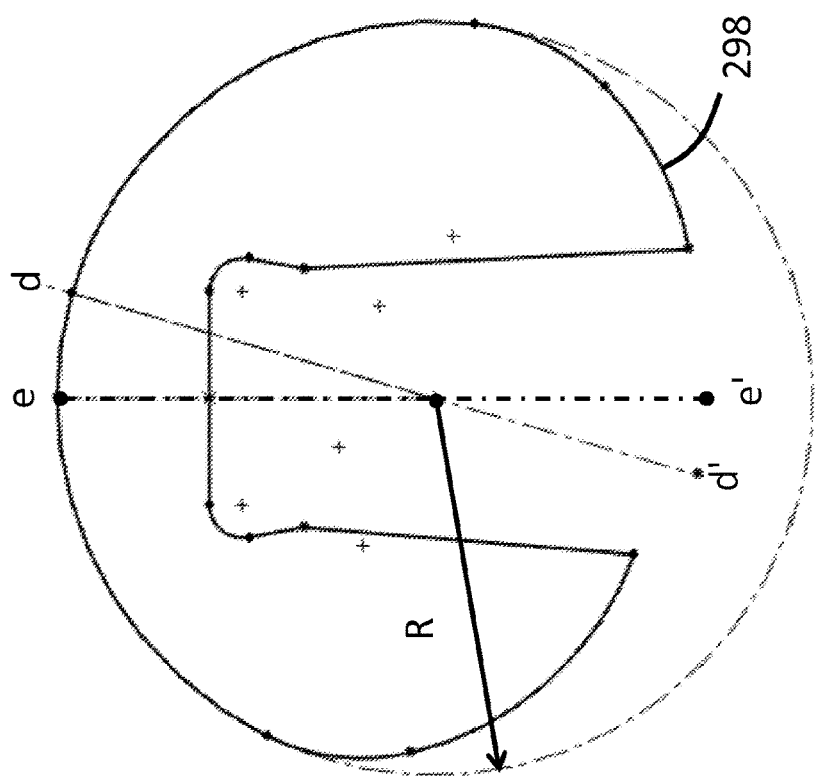
FIG. 37 is a schematic view of one embodiment of a femoral head that has an articular surface that is axisymmetric about an axis d-d', but non-axisymmetric about an axis e-e'.

A non-axisymmetric surface can be obtained by starting with a surface that is symmetric around an axis d-d', shown in FIG. 37 which illustrates an embodiment of a femoral head 298, and rotating it relative to another axis e-e'. This results in a surface that is non-axisymmetric about an axis e-e', but is axisymmetric about the axis d-d'.

Offsetting Inner and Outer Articulation Centers of Mobile Insert

Figure 38A:
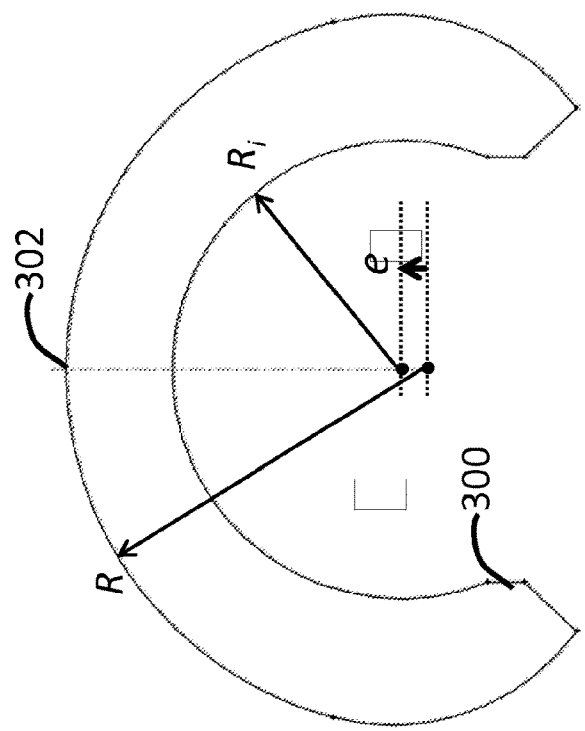
FIG. 38A is a schematic view of one embodiment of a mobile insert with offset of the inner articulation center towards the pole, relative to the outer articulation center.

In some embodiments of a mobile insert, such as those shown in FIG. 12, a center of the inner and outer articulation can be coincident. Herein, the center of the outer articulation is a center of an overall spherical geometry of the outer articular surface (radius R), and the center of the inner articulation is a center of an overall spherical geometry of the inner articular surface (radius $R_i$, FIG. 3B). In other embodiments, the center of the inner and outer articulation can be non-coincident. A distance between these centers can be characterized by an offset 'e', shown with respect to embodiments of mobile insert 300, 310, 312 shown in FIGS. 38A-38C. A value of e in the illustrated embodiment is about 1.5 to 3 mm, but it can be in the range of about 0.1 mm to 20 mm, about 1.5 mm to 15 mm, about 3 mm to 10 mm, about 4 mm to 6 mm, etc. This offset of the inner articulation center relative to the outer articulation center can be in any direction, such that the inner articulation is shifted towards a pole 302 (FIG. 38A), away from a pole 304 (FIG. 39B), towards a pole 306 and away from a mobile insert axis 308 (FIG. 38C), and away from a pole and a mobile insert axis, etc.

The offset between the inner and outer articulations allows the insert to self-adjust in response to external loads. For example, when the inner articulation is shifted towards the pole relative to the outer articulation, the mobile insert self-centers under compressive loads such that the mobile insert axis is aligned with the direction of the load vector (neutral orientation). FIG. 39B shows results of a simulation, where a mobile insert 314 with no offset and a mobile insert 316 with 1.5 mm offset towards the pole, are rotated by 29° (λ) relative to a neutral orientation, as shown in FIG. 39A, and a fixed compressive load of 700N (F) is applied along a neutral orientation axis. The insert 314 with no offset remains in the rotated orientation, while the insert 316 with 1.5 mm offset on each side of the pole (for a total of 3 mm offset) gradually self-centers to return to neutral orientation.

Figure 40A:
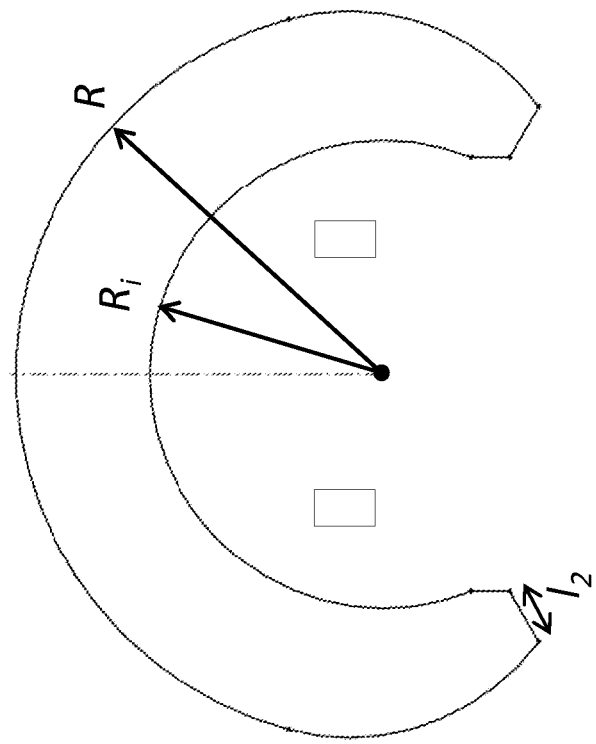
FIG. 40A is a schematic view of one embodiment of a mobile insert with offset of the inner articulation center towards the pole relative to the outer articulation center.
Figure 40B:
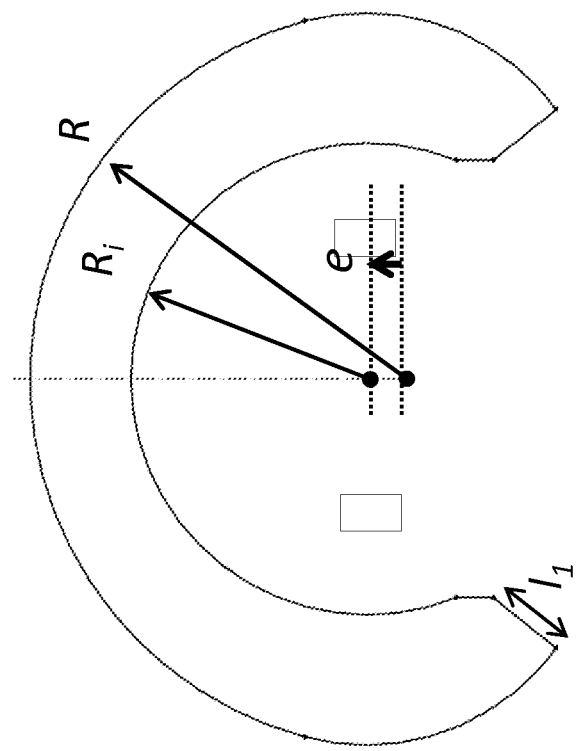
FIG. 40B is a schematic view of one embodiment of a mobile insert with no offset between inner and outer articulation centers. This insert has a smaller rim thickness $l_2$ than the rim thickness $l_1$ of the insert of FIG. 40A.

Offsetting the inner and outer articulation centers allows, for identical articular surface geometries, a design with offset of the inner articulation towards a pole, shown in an embodiment of FIG. 40A, has a peripheral thickness $l_1$ that is greater than a peripheral thickness $l_2$ of a design with no offset, shown in an embodiment of FIG. 40B. This allows for a soft-tissue friendly outer articular surface design that maximizes the thickness and strength of the peripheral edge. This can also improve resistance to extraction of the inner femoral head out of the mobile insert. Offsetting the inner and outer articulation can help to keep the insert in a preferred orientation such that contoured portion of the outer articular surface is preferably exposed to the native soft-tissues.

Reduction in Articular Wear and Frictional Torque

In addition to the soft-tissue impingements concerns, another concern with the use of large diameter femoral heads or mobile inserts is the potential for increased frictional torque, wear, and/or wear rates compared to conventional small diameter femoral heads. (See previously mentioned Lachiewicz et al. and Livermore et al.) The larger wear and wear rates for the large diameter femoral heads or mobile inserts can be due to increased contact area between the femoral head/mobile insert and the acetabular liner/shell.

The contouring of the femoral head/mobile insert articular surface in some embodiments discussed previously can aid in reducing the contact area at the inner/outer articulation, thereby reducing implant wear. The contouring of the femoral head/mobile insert articular surface discussed previously can also aid in reducing frictional torque. This effect was confirmed via experiments comparing frictional resistance in a contoured ceramic femoral head articulating against a ceramic acetabular liner, and frictional resistance in a conventional ceramic femoral head articulating against a ceramic acetabular liner. Both the contoured femoral head and the conventional femoral head had a diameter of 36 mm. The tests were conducted using a pendulum comparator (see FIG. 60B, with a schematic thereof in FIG. 60A) consisting of two stations with 50 lbf weights pivoting around the loaded ceramic-on-ceramic hip implants. Three each of the contoured ceramic femoral head and conventional ceramic femoral heads were tested against six ceramic acetabular liners under 100 lbf and 400 lbf of compressive force. The pendulums were released from the same starting angle and number of swings to come to a full stop was counted. Herein, greater number of swings is indicative of lower frictional resistance/frictional torque. In these tests, as shown in FIG. 61, under 100 lbf compressive force, the contoured heads underwent an average of 28.7±3.7 swings, while the conventional femoral heads underwent 23.4±5.6 swings. Under 400 lbf compressive load, the contoured heads underwent an average of 13.9±1.8 swings, while the conventional ceramic femoral heads underwent 10.4±2.3 swings (FIG. 61). These differences were statistically significant ($p<0.0001$), and indicate that the contoured femoral heads can reduce frictional torque.

Figure 41B:
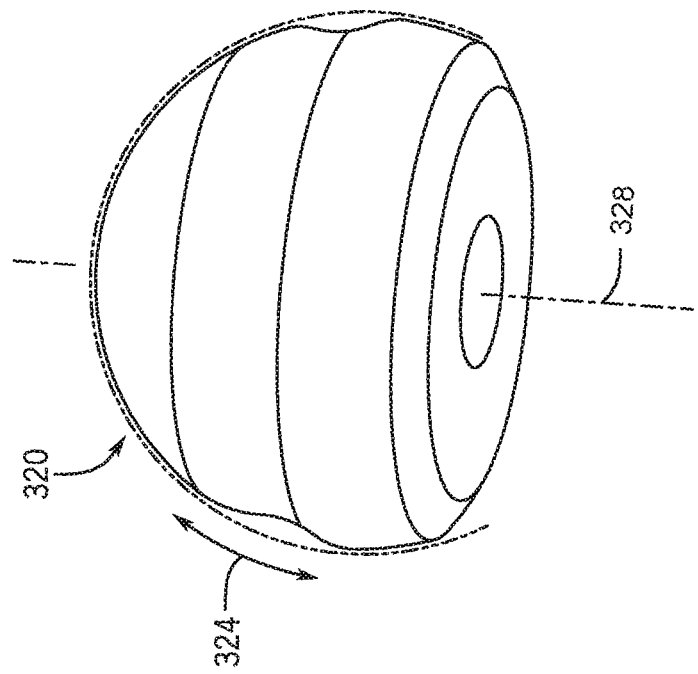
FIG. 41B is a perspective view of another embodiment of a femoral head with a non-peripheral portion of the articular surface carved around a femoral head axis, the carved articular surface being less deep than the carved articular surface of FIG. 41A.
Figure 41A:
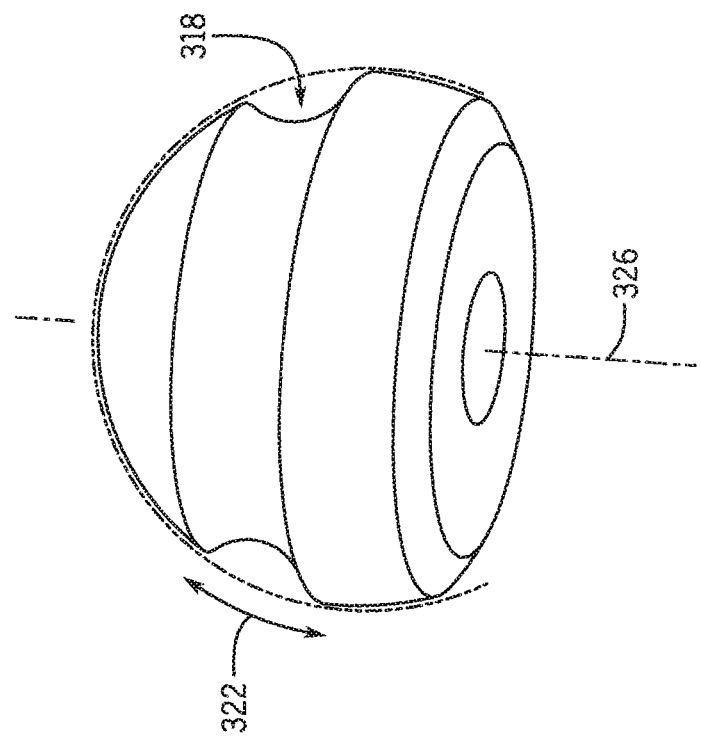
FIG. 41A is a perspective view of an embodiment of a femoral head with a non-peripheral portion of the articular surface carved around a femoral head axis.
Figure 42B:
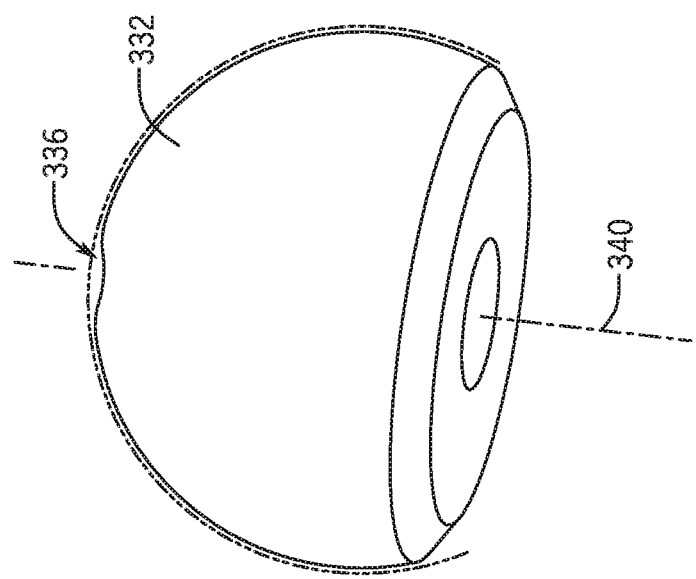
FIG. 42B is a perspective view of another embodiment of a femoral head articular surface carved along a longitudinal direction, such as around an axis perpendicular to a femoral head axis; the carved articular surface being less deep than the carved articular surface of FIG. 42A.
Figure 42A:
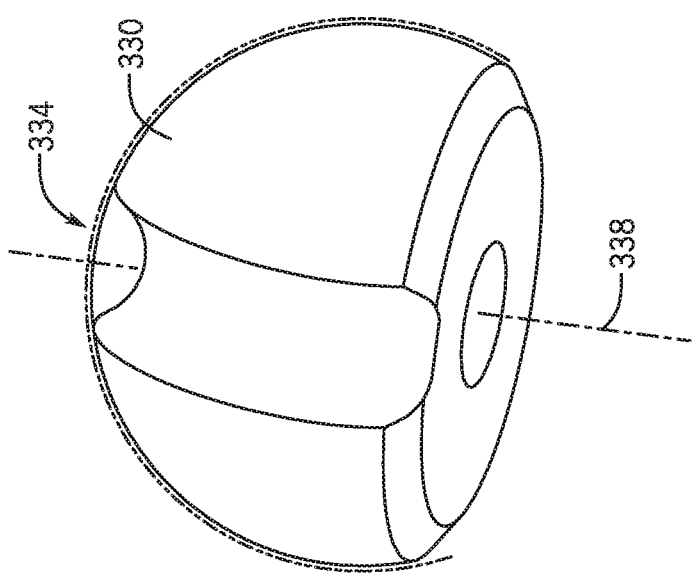
FIG. 42A is a perspective view of an embodiment of a femoral head articular surface carved along a longitudinal direction, such as around an axis perpendicular to a femoral head axis.
Figure 44:
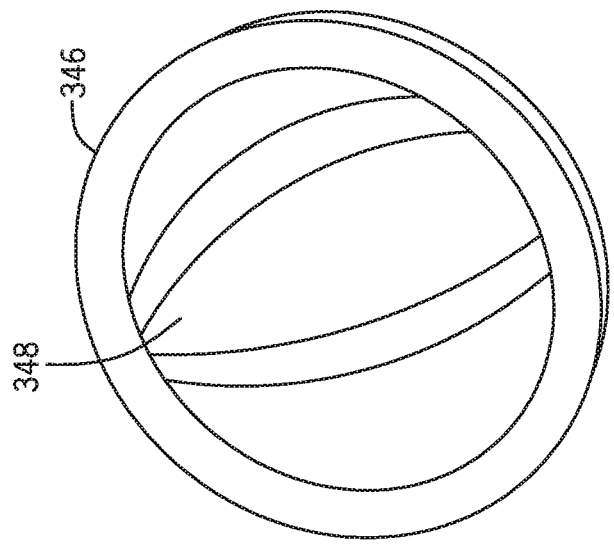
FIG. 44 is a perspective view of an embodiment of an acetabular liner having articular surfaces carved around multiple oblique axes.
Figure 43:
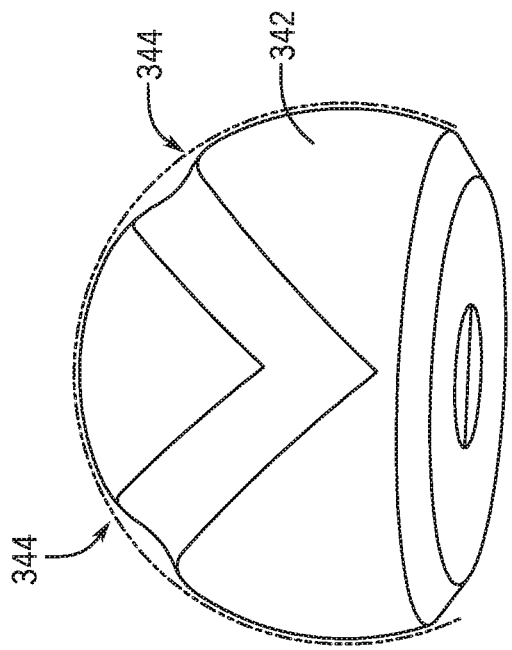
FIG. 43 is a perspective view of an embodiment of a femoral head articular surface carved around multiple oblique axes.
Figure 45B:
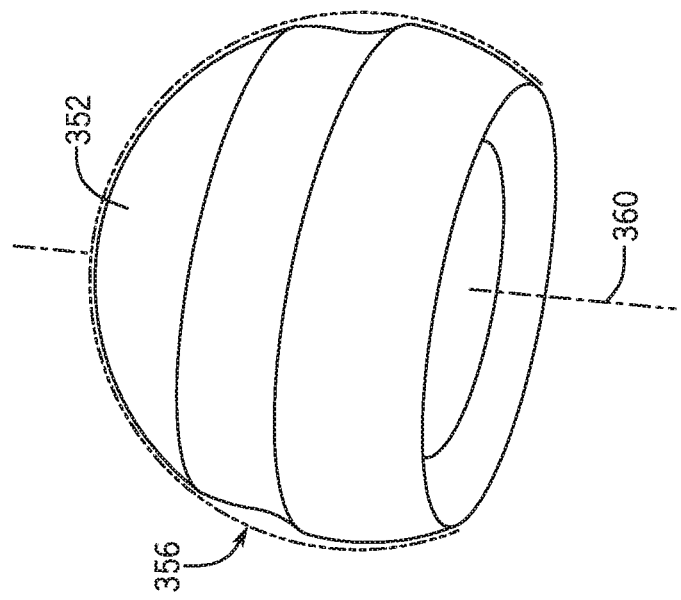
FIG. 45B is a perspective view of another embodiment of a mobile insert having a non-peripheral portion of the articular surface carved around a femoral neck/insert axis, the carved articular surface being less deep than the carved articular surface of FIG. 45A.
Figure 45A:
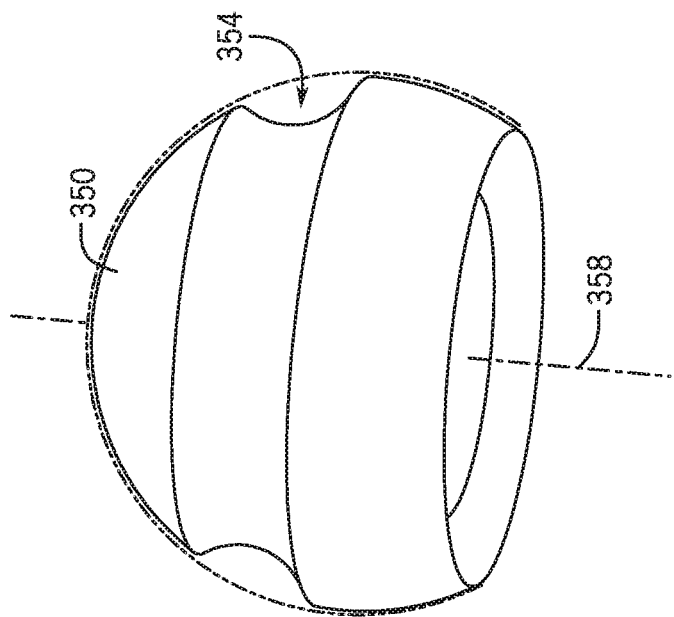
FIG. 45A is a perspective view of an embodiment of a mobile insert having a non-peripheral portion of the articular surface carved around a femoral neck/insert axis.
Figure 46B:
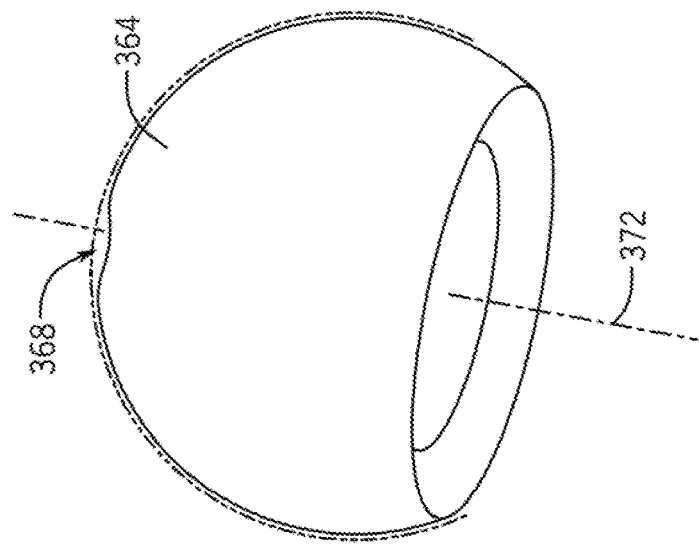
FIG. 46B is a perspective view of another embodiment of a mobile insert having an articular surface carved along a longitudinal direction, such as around an axis perpendicular to an insert axis; the carved articular surface being less deep than the carved articular surface of FIG. 46A.
Figure 46A:
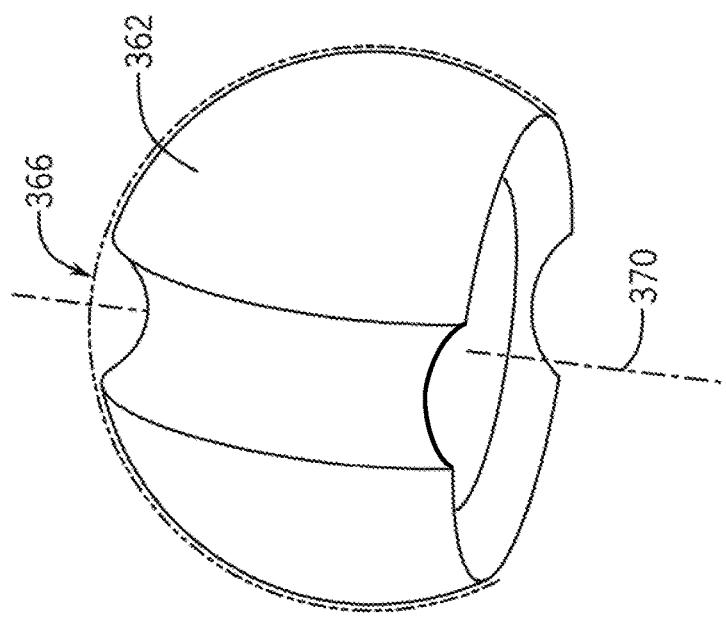
FIG. 46A is a perspective view of an embodiment of a mobile insert having an articular surface carved along a longitudinal direction, such as around an axis perpendicular to an insert axis.
Figure 48:
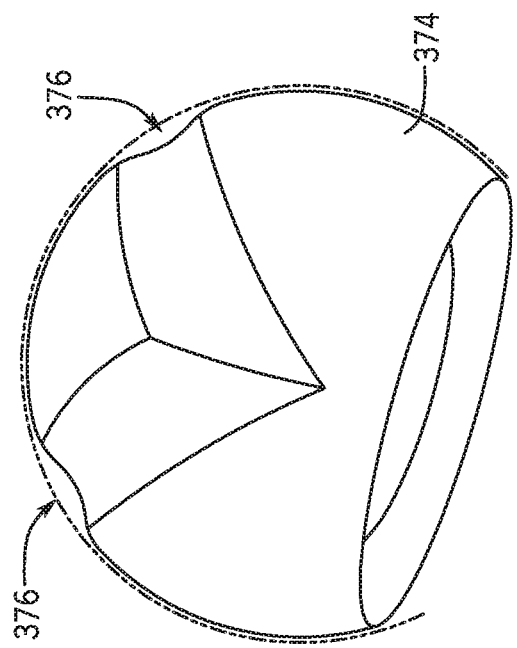
FIG. 48 is a perspective view of an embodiment of a dual mobility acetabular shell having articular surfaces carved around multiple oblique axes.
Figure 47:
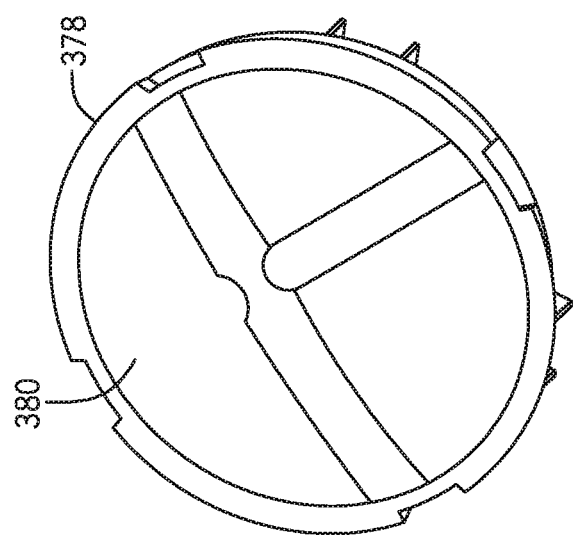
FIG. 47 is a perspective view of an embodiment of a mobile insert having articular surfaces carved around multiple oblique axes.
Figure 49C:
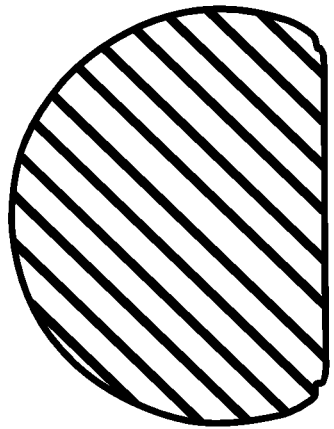
FIG. 49C is a schematic view of an embodiment of a femoral head/mobile insert articular surface having textured articular surfaces in a parallel-diagonal-line pattern.
Figure 49B:
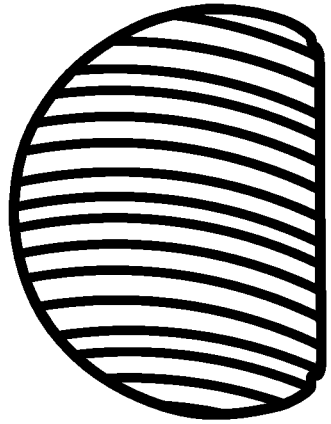
FIG. 49B is a schematic view of an embodiment of a femoral head/mobile insert articular surface having textured articular surfaces in a parallel-arc pattern.
Figure 49E:
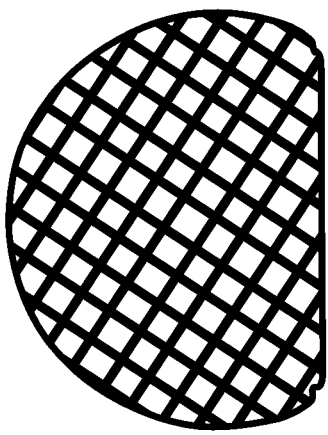
FIG. 49E is a schematic view of an embodiment of a femoral head/mobile insert articular surface having textured articular surfaces in a diagonal checkerboard pattern.
Figure 49A:
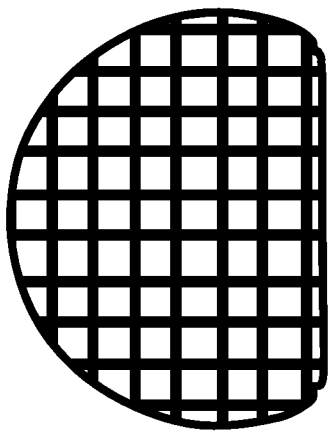
FIG. 49A is a schematic view of an embodiment of a femoral head/mobile insert articular surface having textured articular surfaces in a checkerboard pattern.
Figure 49D:
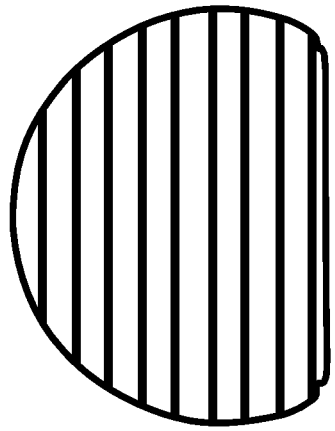
FIG. 49D is a schematic view of an embodiment of a femoral head/mobile insert articular surface having textured articular surfaces in a parallel-horizontal-line pattern.

Specific peripheral or non-peripheral regions of a femoral head or acetabular articular surface (acetabular shell, acetabular liner, or mobile insert) can be contoured, such as by removing or carving out portions of the articular surface to reduce an effective contact area. FIGS. 41A and 41B show embodiments of femoral heads 318, 320 with non-peripheral portions 322, 324 of a femoral head articular surface carved around a femoral head axis 326, 328. The head 318 of FIG. 41A has a deeper carved femoral head articular surface than the head 320 of FIG. 41B. FIGS. 42A and 42B show embodiments of femoral heads 330, 332 each having a femoral head articular surface 334, 336 carved along a longitudinal direction, such as around an axis perpendicular to a femoral head axis 338, 340. The head 330 of FIG. 42A has a deeper carved femoral head articular surface than the head 332 of FIG. 42. FIG. 43 shows an embodiment of a femoral head 342 with a femoral head articular surface 344 carved around multiple oblique axes. Similarly, FIG. 44 shows an embodiment of an acetabular liner 346 with an articular surface 348 carved around multiple oblique axes. FIGS. 45A and 45B show embodiments of mobile inserts 350, 352 each having a mobile insert articular surface 354, 356 carved around an insert axis 358, 360. The insert 350 of FIG. 45A has a deeper carved mobile insert articular surface than the insert 352 of FIG. 45B. FIGS. 46A and 46B show embodiments of mobile inserts 362, 364 each having a mobile insert articular surface 366, 368 carved along a longitudinal direction, such as around an axis perpendicular to an insert axis 370, 372. The insert 362 of FIG. 46A has a deeper carved mobile insert articular surface than the insert 364 of FIG. 46B. FIG. 47 shows an embodiment of a mobile insert 374 with a mobile insert articular surface 376 carved around multiple oblique axes. Similarly, FIG. 48 shows an embodiment of a dual mobility acetabular shell 378 with an articular surface 380 carved around multiple oblique axes.

In some embodiments, a femoral head, mobile insert, or acetabular articular surface can be textured, which can effectively reduce an articular contact area, e.g., reduce the articular surface area in contact with an acetabular articular surface. FIGS. 49A-49E show embodiments of textured femoral heads or mobile inserts, where thick dark lines indicate valleys or troughs on the femoral head's articular surface. The texturing can lead to effective reduction of the articular surface area in contact with an acetabular liner or acetabular shell surface.

Large Taper Junction

In an exemplary embodiment, a taper junction of an orthopedic implant can be a conical taper junction, as shown in an embodiment of a taper junction 382 shown in FIGS. 50A and 50B, with one or more of a small diameter circular profile d1, large diameter circular profile d2, and length L being significantly larger than in a conventional taper junction 50 (see FIGS. 7A-7B). The circular profiles of conventional taper junctions have a diameter d1 and d2 pairing of 8 mm and 10 mm, 12 mm and 14 mm, and 14 mm and 16 mm. A length L of the taper junction 50 measured along a taper axis of the taper junction 50 is about 10 mm to 12 mm. A resulting taper angle λ is in a range of about 5° to 6°. In the large taper junction 382, d1 is greater than about 14 mm, d2 is greater than about 16 mm, and/or the taper length L is greater than about 12 mm. When used in a femoral head-neck junction, the large taper junction 382 would occupy a significantly larger volume of a femoral head 384 than the conventional taper junction 50. In an embodiment with a large d2 diameter, the radial clearance $r_c$ between the edge of the taper surface and the end of the femoral articular surface would be significantly smaller than in the conventional design 50 ($r'_c$). In an embodiment with a large taper length L, the taper junction 352 would extend deeper into the femoral head 354 than in the conventional design 50.

The larger taper dimension can provide increased resistance to torsional and moment loads, which can help minimize loosening and micromotion. In the large taper junction 382, a center 386 of the femoral-head neck taper junction 382 would be located closer to a femoral articular surface than a center 388 of the conventional femoral-head neck taper junction 50, thereby reducing a moment arm 390 of a joint load 392 acting on the taper joint, as shown in FIG. 50.

Non-Circular Taper Junction

Figure 51:
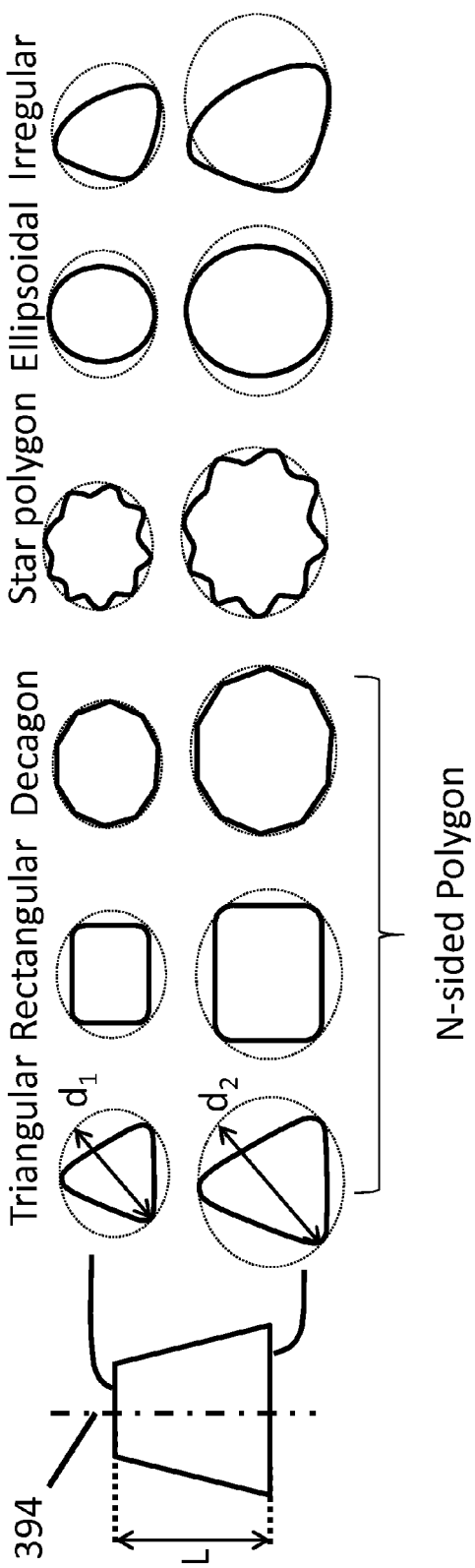
FIG. 51 is a schematic view of various embodiments of taper junctions having non-circular cross-sections.

A modular junction can be a taper junction having a non-circular cross-section perpendicular to a taper junction axis of the taper junction. The non-circular profile can provide increased resistance to torsional loads, which can help minimize loosening and micromotion. The non-circular cross-section can take various forms in different embodiments. FIG. 51 illustrates various exemplary embodiments of taper junctions having non-circular cross-sections perpendicular to a taper junction axis 394. In some embodiments, the non-circular cross-sectional profile can be an N-sided polygon with rounded corners, such as the three N-sided polygons illustrated in FIG. 51. Examples of such cross-sectional profiles include a triangular profile with N=3, a rectangular profile with N=4, and a decagonal profile with N=10. In some embodiments, the non-circular cross-sectional profile can be a star shaped polygon (FIG. 51), ellipsoidal (FIG. 51), pear shaped, or any other irregular geometry (one example of which is shown in FIG. 51). An overall dimension of the non-circular cross-sectional profile can be defined as a diameter of the largest bounding circle. The overall dimension of the non-circular cross-sectional profile can vary along a length L of the taper junction from a bounding circle diameter d1 of about 5 mm to 35 mm, about 10 mm to 30 mm, about 15 mm to 20 mm, etc. to a bounding circle diameter d2 of about 6 mm to 40 mm, about 12 mm to 32 mm, about 16 mm to 22 mm, etc. The length L of the taper junction can range from about 5 mm to 45 mm, about 15 mm to 30 mm, about 20 mm to 25 mm, etc. The resulting taper angle λ is about 6°, but can be in a range of about 1° to 75°, about 5° to 45°, about 10° to 25°, etc.

Shape Memory Alloy Taper Junction

In an exemplary embodiment, fixation of a modular junction can be enhanced by using shape memory material. For example, shape memory alloys such as Nitinol (Nickel-titanium alloy) exist in difference crystalline states at different temperatures, a martensitic state below a transition temperature (State 1) and an austenitic state above the transition temperature (State 2). The change in state is associated with a change in density, volume, and/or geometry. Additionally, this change can be either irreversible after crossing the transition temperature (1-way), or allow for repeated switching between states in response to cycling of the temperature (2-way). Such shape memory properties of any shape memory material can be utilized to enhance, e.g., tighten and/or strengthen, the fixation of the modular junction. A person skilled in the art will appreciate that an element being composed of a shape memory material can be composed of a single shape memory material or a combination of any two or more shape memory materials.

In one embodiment illustrated in FIGS. 52A and 52B, a shape memory material (SMM) sleeve 396 can be interposed between a cavity or female taper surface 398 of a first component (such as a femoral head) and an outer or male taper surface 400 of a second component (such as a femoral neck). In State 1 of the SMM sleeve 396, shown in FIG. 52A, the sleeve 396, the first component, and the second component can be assembled via impaction, as a conventional taper junction. A transition to State 2 of the SMM sleeve 396, shown in FIG. 52B, can then be imposed via an external stimulus (e.g., a change in temperature), leading to further tightening of the taper junction.

In another embodiment, a sleeve can be composed of at least one SMM, and a cavity or female taper surface in a first component (e.g., a femoral head) can be composed of two parts, a part with a positive taper angle and a part with a negative taper angle. FIGS. 53A-53C show an embodiment of a sleeve 402 composed of at least one SMM, and a cavity or female taper surface 404 in a first component (e.g., a femoral head) composed of two parts, a part with a positive taper angle 406 and a part with a negative taper angle 408 (FIGS. 53B and 53C). The portions with positive and negative taper angles 406, 408 are angled in an opposite directions relative to a taper junction axis 410. An inner surface of the cavity 404, and the inner and outer surface of the SMM sleeve after transition from State 1 (FIG. 53A) to State 2 (FIG. 53B), have portions with positive and negative taper angle. In State 1, the inner and outer surfaces of the SMM sleeve 402 have a positive taper angle that allows assembly via impaction. A transition to State 2 is then imposed via an external stimulus, causing the SMM sleeve geometry to change such that the inner and outer surfaces of the SMM sleeve 402 now have a part positive angle and a part negative taper angle, as shown in FIG. 53B. Additionally the SMM sleeve 402 undergoes a volumetric expansion. This tightens the taper junction and causes engagement of the outer surface of sleeve 402 with the inner surface of the femoral head cavity 404. Simultaneously, the portion of the inner surface of the sleeve 402 with positive taper angle engages with the outer surface of the prosthetic femoral neck 412.

FIGS. 54A and 54B illustrate an embodiment of a femoral head-neck taper junction where at least a portion of a femoral neck is made of a SMM. In the illustrated embodiment, an outer surface 414 of the femoral neck is made of the SMM. In other embodiments, the entire femoral head or femoral neck can be made of a SMM. In State 1 of the SMM (FIG. 54A), the components forming the taper junction can be assembled via impaction. A transition to State 2 (FIG. 54B) of the SMM can then be imposed, to further tighten the taper junction, e.g., by filling more of a femoral head cavity 416 with the femoral neck.

FIGS. 55A and 55B illustrate another embodiment of a femoral head-neck taper junction where at least a portion of a femoral neck is made of a SMM. In the illustrated embodiment, an outer surface 418 of the femoral neck is made of the SMM. In this illustrated embodiment, a femoral head cavity 420 has a surface with part positive taper angle 422 and a part negative taper angle 424, while the femoral neck is composed of a SMM and has an outer surface with a positive taper angle. In State 1 (FIG. 55A) of the SMM, the femoral head and femoral neck can be assembled via impaction. A transition to State 2 (FIG. 55B) of the SMM can then be imposed, causing the geometry of the outer surface 418 of the femoral neck to change to a surface with part positive and part negative taper angle. Additionally, the SMM sleeve undergoes a volumetric expansion from State 1 to State 2. This tightens the taper junction and causes engagement of the portions of the femoral neck and femoral head with the negative taper angles.

The devices disclosed herein can be designed to be disposed of after a single use, or they can be designed to be used multiple times. In either case, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to or during a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An orthopedic implant comprising:
    a femoral head implant that includes a portion of an outer surface thereof having a peripheral portion that is contoured so as to achieve an inward shift of the outer surface relative to an overall spherical geometry of the femoral head implant;
    wherein the femoral head implant has a femoral head rim comprising an edge or surface marking an end of a femoral head articular surface of the femoral head implant;
    wherein the femoral head implant has a femoral head axis defined by a reference line passing through a center of the overall spherical geometry of the femoral head implant to a geometric center of the femoral head rim of the femoral head implant;
    wherein the inward shift occurs at an angle greater than about 80° measured from an intersection of the femoral head axis with the outer surface of the femoral head implant; and
    wherein the portion that is contoured extends to the femoral head rim, and the inward shift of the outer surface is achieved using at least one convex radius having a value no less than 15% of the overall spherical radius of the femoral head implant.

2. The implant of claim 1, wherein the inward shift of the outer surface relative to an overall spherical geometry of the femoral head implant is asymmetric around a femoral head axis of the femoral head implant, and may be restricted to limited range of azimuth angle measured around the femoral head axis.

3. The implant of claim 1, wherein the inward shift of the outer surface relative to an overall spherical geometry of the femoral head implant is achieved through a change in radius of curvature.

4. The implant of claim 1, wherein the inward shift of the outer surface relative to an overall spherical geometry of the femoral head implant is achieved through a change in center of curvature.

5. The implant of claim 1, wherein the inward shift of the outer surface relative to an overall spherical geometry of the femoral head implant is at least about 0.5 mm at a location of maximum inward shift.

6. An orthopedic implant comprising:
    a femoral head implant that includes a portion of an outer surface thereof having a peripheral portion that is contoured so as to achieve an inward shift of the outer surface relative to an overall spherical geometry of the femoral head implant;
    wherein the femoral head implant has a femoral head rim comprising an edge or surface marking an end of a femoral head articular surface of the femoral head implant;
    wherein the femoral head implant has a femoral head axis defined by a reference line passing through a center of the overall spherical geometry of the femoral head implant to a geometric center of the femoral head rim of the femoral head implant; and
    wherein the portion that is contoured extends to the femoral head rim, and the inward shift is asymmetric around the femoral head axis of the femoral head implant, and may be restricted to limited range of azimuth angle measured around the femoral head axis.

7. An orthopedic implant, comprising:
    a mobile insert having an inner surface and an outer surface, the outer surface having a peripheral portion that is contoured so as to achieve an inward shift of the outer surface relative to an overall spherical geometry of the mobile insert;
    wherein the mobile insert has a mobile insert rim comprising an edge or surface marking an end of an articular surface of the mobile insert; and
    wherein the peripheral portion that is contoured extends to the mobile insert rim.

8. The implant of claim 7, wherein the inward shift of the outer surface relative to the overall spherical geometry of the mobile insert is achieved through a change in radius of curvature.

9. The implant of claim 7, wherein the inward shift of the outer surface relative to the overall spherical geometry of the mobile insert is achieved through a change in center of curvature.

10. The implant of claim 7, wherein the inward shift of the outer surface relative to an overall spherical geometry of the mobile insert is at least about 0.5 mm at a location of maximum inward shift.

11. The implant of claim 7,
    wherein the mobile insert has a mobile insert axis defined by a reference line passing through a center of the overall spherical geometry of the mobile insert to a geometric center of the mobile insert rim;
    wherein the inward shift of the outer surface relative to an overall spherical geometry of the mobile insert is asymmetric around a mobile insert axis and may be restricted to limited range of azimuth angle measured around the femoral head axis.

12. The implant of claim 7,
    wherein the center of the overall spherical geometry of the inner surface is non-coincident with the center of the overall spherical geometry of the outer surface.

* * * * *